US011253374B2

(12) United States Patent
Krause et al.

(10) Patent No.: US 11,253,374 B2
(45) Date of Patent: Feb. 22, 2022

(54) PERCUTANEOUS BONE GRAFT DELIVERY SYSTEM AND METHOD

(71) Applicant: Stryker European Operations Holdings LLC, Kalamazoo, MI (US)

(72) Inventors: Steven F. Krause, Oakland, NJ (US); Abram Reitblat, Monroe, NY (US); Paul R. Rochette, Stanhope, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 258 days.

(21) Appl. No.: 16/170,153

(22) Filed: Oct. 25, 2018

(65) Prior Publication Data

US 2019/0060086 A1 Feb. 28, 2019

Related U.S. Application Data

(63) Continuation of application No. 14/520,607, filed on Oct. 22, 2014, now abandoned.
(Continued)

(51) Int. Cl.
*A61F 2/46* (2006.01)
*A61B 17/34* (2006.01)
(Continued)

(52) U.S. Cl.
CPC .......... *A61F 2/4601* (2013.01); *A61B 17/025* (2013.01); *A61B 17/3421* (2013.01); *A61B 17/3472* (2013.01); *A61B 17/7094* (2013.01); *A61B 17/3417* (2013.01); *A61B 2017/0046* (2013.01); *A61B 2017/00261* (2013.01); *A61B 2017/3454* (2013.01); *A61F 2002/2835* (2013.01); *A61F 2002/4635* (2013.01)

(58) Field of Classification Search
CPC . A61F 2/4601; A61B 17/025; A61B 17/3421; A61B 17/3472; A61B 17/7094
USPC ...................................................... 606/92–94
See application file for complete search history.

(56) References Cited

U.S. PATENT DOCUMENTS 6,383,519 B1  5/2002  Sapieszko et al.
6,521,246 B2  2/2003  Sapieszko et al.
(Continued)

OTHER PUBLICATIONS

Extended European Search Report for EP 17 19 2912 dated Jan. 18, 2018.
(Continued)

*Primary Examiner* — Si Ming Ku
(74) *Attorney, Agent, or Firm* — Lerner, David, Littenberg, Krumholz & Mentlik, LLP

(57) ABSTRACT

A bone graft delivery system includes a bone graft injector and an access portal. The access portal may include a handle having a first arm pivotably connected to, and biased away from, a second arm. A ratchet including a pawl may extend from the second arm. A delivery tube may be configured to mate with the first arm and be configured to store a bone graft material therein. A plunger including a shaft and a plunger tip at the distal end thereof may be configured to move through the delivery tube. At least a portion of the shaft may include teeth, the pawl of the ratchet being configured to iteratively contact the teeth. A user may hold the access portal with a first hand and the bone graft injector with a second hand, iteratively squeezing the handle to iteratively eject amounts of bone graft material into a patient.

12 Claims, 38 Drawing Sheets

Related U.S. Application Data

(60) Provisional application No. 61/894,549, filed on Oct. 23, 2013.

(51) Int. Cl.
  A61B 17/02 (2006.01)
  A61B 17/70 (2006.01)
  *A61F 2/28* (2006.01)
  *A61B 17/00* (2006.01)

(56) References Cited

U.S. PATENT DOCUMENTS

| | | | |
|---|---|---|---|
| 7,534,451 B2 | 5/2009 | Erbe et al. | |
| 8,162,967 B1 | 4/2012 | Kaiser et al. | |
| 8,672,193 B2 | 3/2014 | Vukic et al. | |
| 2002/0049449 A1 | 4/2002 | Bhatnagar et al. | |
| 2003/0083688 A1* | 5/2003 | Simonson | A61B 1/32 606/191 |
| 2004/0092946 A1* | 5/2004 | Bagga | A61B 17/1671 606/93 |
| 2004/0215201 A1 | 10/2004 | Lieberman | |
| 2005/0096507 A1* | 5/2005 | Prosek | A61B 17/34 600/204 |
| 2005/0113762 A1* | 5/2005 | Kay | A61F 2/4601 604/181 |
| 2005/0288795 A1 | 12/2005 | Bagga et al. | |
| 2007/0213655 A1 | 9/2007 | Prusmack | |
| 2007/0270896 A1* | 11/2007 | Perez-Cruet | A61B 17/1796 606/181 |
| 2008/0065083 A1 | 3/2008 | Truckai et al. | |
| 2009/0131986 A1* | 5/2009 | Lee | A61B 17/1671 606/247 |
| 2009/0318925 A1* | 12/2009 | Campion | A61B 17/8816 606/93 |
| 2010/0228085 A1* | 9/2010 | Mirza | A61B 1/00087 600/106 |
| 2010/0282774 A1 | 11/2010 | Greter et al. | |
| 2010/0288790 A1 | 11/2010 | Keller | |
| 2011/0077495 A1* | 3/2011 | Gilbert | A61B 5/6852 600/367 |
| 2011/0218513 A1* | 9/2011 | Walker | A61B 17/8816 604/500 |
| 2011/0238184 A1 | 9/2011 | Zdeblick et al. | |
| 2012/0053642 A1 | 3/2012 | Lozier et al. | |
| 2012/0111897 A1 | 5/2012 | Vukic et al. | |
| 2012/0245426 A1* | 9/2012 | Salvas | A61B 17/3423 600/208 |
| 2012/0289816 A1* | 11/2012 | Mark | A61B 5/4064 600/411 |
| 2013/0087578 A1 | 4/2013 | Brem et al. | |
| 2013/0131683 A1 | 5/2013 | Shah et al. | |
| 2014/0257232 A1 | 9/2014 | Mathur et al. | |

OTHER PUBLICATIONS

Extended European Search Report for Application No. EP16165836 dated Jun. 16, 2016.
European Search Report for Application No. EP14189839 dated Jan. 26, 2015.

* cited by examiner

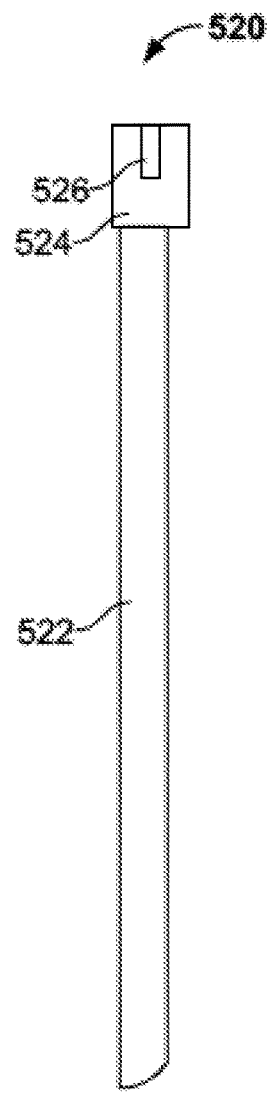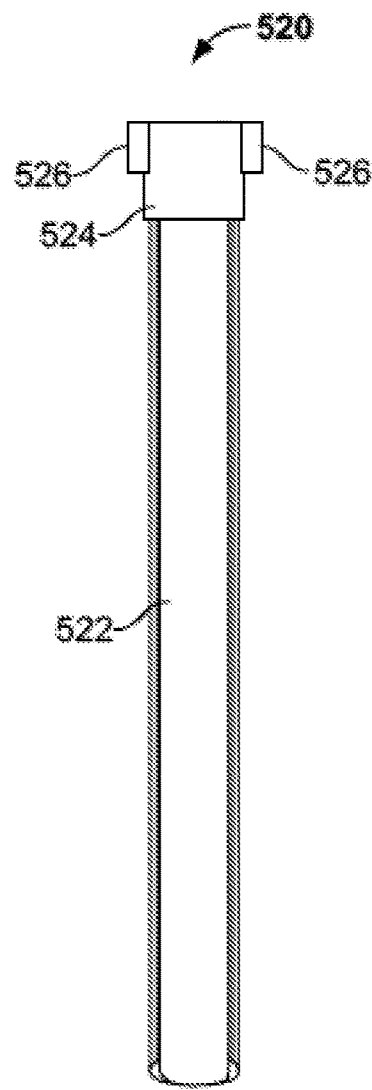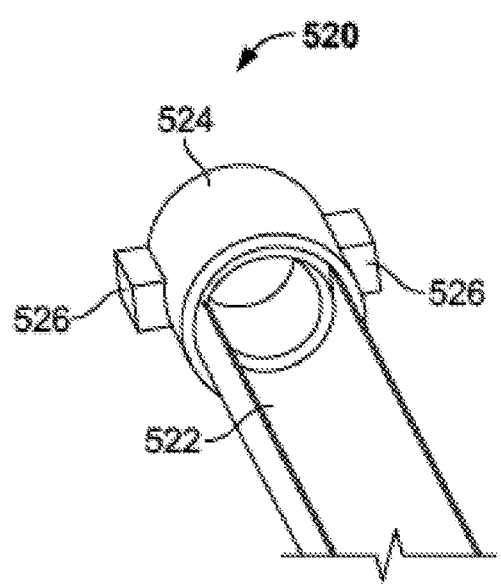
FIG. 6D     FIG. 6E     FIG. 6F

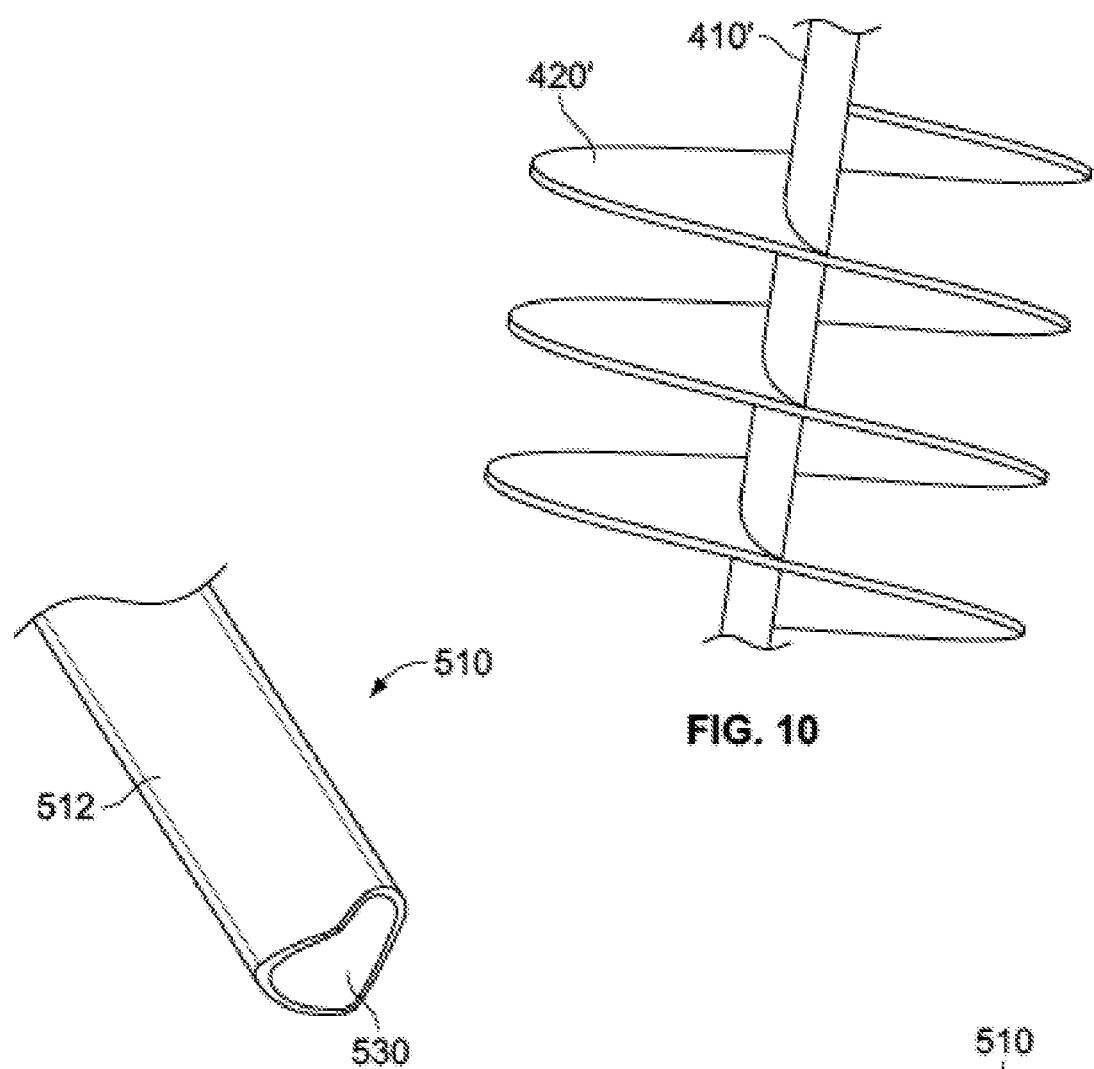
FIG. 10
FIG. 11A
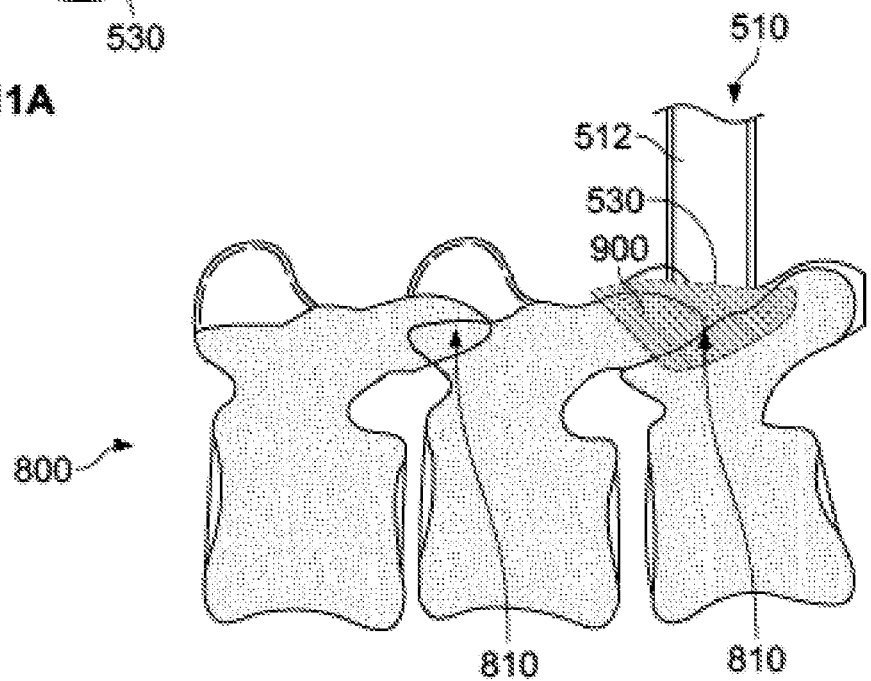
FIG. 11B

PERCUTANEOUS BONE GRAFT DELIVERY SYSTEM AND METHOD

CROSS-REFERENCE TO RELATED APPLICATIONS

The present application is a continuation of U.S. patent application Ser. No. 14/520,607, filed Oct. 22, 2014, which claims the benefit of the filing date of U.S. Provisional Patent Application No. 61/894,549 filed Oct. 23, 2013, the disclosures of which are hereby incorporated by reference herein.

FIELD OF THE INVENTION

The present invention relates to apparatus and methods for delivering materials to bone during a surgical procedure, and more particularly to injectors and access portals for percutaneously delivering bone graft or bone graft substitute material during spinal procedures.

BACKGROUND

There is an increasing prevalence in spinal procedures being performed percutaneously in a minimally invasive way. Often, spinal fixation procedures include delivery of bone graft or bone graft substitute to aid implants or screws in fixing and/or fusing portions of the spinal column. However, there are challenges to delivering such bone graft materials percutaneously during minimally invasive surgical procedures. As used herein, the term "bone graft" refers generally to bone graft, bone graft alternative, bone graft substitute, bone marrow aspirate, or mixtures thereof, whether occurring naturally or artificially, unless specified otherwise.

Currently, in certain surgical procedures, facet joints of the spine may be fused, at least in part, by attaining access to the joints through a portal (such as a tube or a retractable blade) and placing or injecting bone graft into the joint area. For example, in one current procedure, a surgeon places bone graft through a tube which is fixed to the operating room table ("OR table") via a flexible fixation arm. The graft is placed onto and around the joint little by little through the use of forceps repeatedly placed into the surgical site and taken away to load more bone graft.

One current system for bone graft delivery is the PerX360° System, sold by Interventional Spine. This system generally includes a funnel into which bone graft is packed, and a hand-held plunger that forces the bone graft through the funnel to the site of interest. Another system, the T-System by MEDMIX, is a one handed dispenser system for demineralized bone matrix ("DBM"), putty, or bone graft. Other systems, such as Medtronic's Quadrant device, include a portal affixed to a fixation arm docked to an OR table through which a syringe is inserted to inject bone graft.

The current approaches and systems generally utilize approaches involving several steps, which may involve re-aligning the access portal in order to achieve sufficient placement of bone graft and/or loading a delivery tube multiple times with bone graft. In a number of the current systems, two hands are required to operate the portion of the system that delivers or injects the bone graft. This results in a cumbersome procedure in which an access portal fixed to the OR table may need to be positioned as desired, and then the surgeon uses both hands to operate the graft delivery system. The portal may then have to be repositioned, the bone graft delivery system re-loaded with bone graft and delivered to the desired site, and so on and so forth. It would be desirable to have a bone graft delivery system optimized to reduce the time required for the procedure, including a one-handed bone graft delivery portion and a one-handed access portal to achieve rapid and optimal placement of bone graft at the desired site.

BRIEF SUMMARY OF THE INVENTION

A bone graft delivery system may include a bone graft injector configured to be held in a first hand of a surgeon and an access portal configured to be simultaneously held in a second hand of the surgeon. Generally, the bone graft injector may include a handle that may be iteratively squeezed, with each squeeze of the handle causing a plunger to move through a delivery tube packed with bone graft substitute. Each squeeze of the handle expels an amount of bone graft material from the bone graft injector into the patient guided by the access portal, and the surgeon may iteratively expel the bone graft material by iteratively squeezing the handle, all the while manipulating and or maneuvering the access portal and the bone graft injector with separate hands.

In one embodiment of the disclosure a bone graft delivery system, comprises a bone graft injector assembly and an access portal assembly. The bone graft injector assembly may include a handle having a first arm pivotably connected to a second arm, the first arm being biased away from the second arm. It may also include a ratchet assembly extending from the second arm, the ratchet assembly including a pawl extending therefrom. It may further include a delivery tube assembly configured to mate with the first arm and configured to store a bone graft material therein. It may additionally include a plunger assembly configured to move through the delivery tube assembly, the plunger assembly including a shaft and a plunger tip at the distal end of the shaft. At least a portion of the shaft may include a plurality of teeth. The pawl of the ratchet assembly may be configured to contact one of the plurality of teeth and to drive the plunger assembly in a first direction when the ratchet assembly moves in the first direction, the pawl remaining in contact with the one tooth. The pawl may further be configured to contact another one of the plurality of teeth after the ratchet assembly is moved in a second direction opposite the first direction.

The delivery tube assembly may include an outer cannula and an inner cannula. The outer cannula may have the general shape of a hollow cylinder and a distal end through which the bone graft material is configured to exit. The distal end of the outer cannula may include an off-axis cutout formed in a portion of a circumference of the outer cannula. The off-axis cutout may be generally "U"-shaped. At least a portion of the inner cannula may be elongated and hollow and have a generally partially cylindrical shape. At least a portion of the inner cannula may be generally trough shaped.

The access portal assembly may include a handle, a first arm connected to the handle, a second arm connected to the first arm, and a tube connected to and extending generally perpendicular from the second arm. A distal end of the tube may be beveled. The beveled distal end of the tube may be angled with respect to a wall of the tube between approximately 20 degrees and approximately 40 degrees, for example approximately 30 degrees. The second arm may be angled with respect to the handle between approximately 10 degrees and approximately 30 degrees, for example approximately 20 degrees.

In another embodiment of the invention, a method of delivering a bone graft material to a patient includes providing an access tube assembly and a bone graft injector assembly. The bone graft injector assembly may include a handle with a first arm pivotably connected to a second arm and a ratchet assembly extending from the second arm. It may also include a delivery tube assembly configured to mate with the first arm and configured to store a bone graft material therein. It may further include a plunger assembly configured to move through the delivery tube assembly, the plunger assembly including a shaft configured to couple to a portion of the ratchet assembly and a plunger tip at the distal end of the shaft. The method may also include creating an incision in the patient to access the bone and inserting the access tube assembly into the patient through the incision. The method may further include loading the delivery tube assembly with the bone graft material, and expelling a first amount of bone graft material from the delivery tube assembly by moving the first arm toward the second arm to drive the ratchet assembly and the plunger assembly distally, the plunger tip forcing the first amount of bone graft material through the delivery tube assembly as the plunger tip moves through the delivery tube assembly.

The method may further include simultaneously manipulating that access tube assembly with a first hand and the bone graft injector assembly with a second hand. The method may also include moving the first arm away from the second arm to move the ratchet assembly proximally with respect to the plunger assembly. A biasing member may bias the first arm away from the second arm, and the step of moving the first arm away from the second arm may be accomplished, at least in part, by the biasing member. The biasing member may be a spring. The method may also include expelling a second amount of bone graft material from the delivery tube assembly by moving the first arm toward the second arm to drive the ratchet assembly and the plunger assembly distally, the plunger tip forcing the second amount of bone graft material through the delivery tube assembly as the plunger tip moves through the delivery tube assembly. The method may still further include simultaneously manipulating the access tube assembly with a first hand and the bone graft injector assembly with a second hand. The method may also include removing the bone graft injector assembly from the access tube assembly and inserting a tamping device into the access tube assembly.

According to still another embodiment of the invention, a bone graft injection system includes a body and a handle assembly operatively coupled to the body. A cannula may be coupled to and extend from the body. A tube may be configured to be positioned at least partially within the body and at least partially within the cannula. A plunger may be configured to be positioned at least partially within the tube and be operably coupled to the handle assembly so that actuation of the handle assembly advances the plunger within the tube.

According to another embodiment of the invention, a method for delivering a bone graft material to a surgical site in a patient includes providing access through skin of a patient with an access portal. A trocar may be inserted into a cannula extending from a bone graft injection device so that a distal tip of the trocar extends beyond a distal end of the cannula, the distal tip of the trocar having at least one cutting surface. The bone graft injection device may be advanced through the access portal to the surgical site, and the trocar may be removed from the bone graft injection device. A delivery tube assembly loaded with the bone graft material may be inserted into the cannula of the bone graft injection device. The bone graft material may be expelled from the delivery tube assembly to the surgical site.

According to a further embodiment of the invention, a method for delivering a bone graft material to a space between adjacent vertebrae in a patient includes providing access through skin of a patient with an access portal. A distractor may be inserted into a cannula extending from a bone graft injection device so that a distal tip of the distractor extends beyond a distal end of the cannula. A space holder may be positioned over the cannula so that a distal end of the space holder is positioned proximally of the distal tip of the distractor. The bone graft injection device may be advanced through the access portal until the distal tip of the distractor is positioned within the intervertebral space. The distractor may be rotated to distract the adjacent vertebrae. The space holder may be advanced so that the distal end of the space holder is positioned within the intervertebral space. The distractor may be removed from the bone graft injection device. A delivery tube assembly loaded with the bone graft material may be inserted into the cannula of the bone graft injection device. The bone graft material may be expelled from the delivery tube assembly to the surgical site.

BRIEF DESCRIPTION OF THE DRAWINGS

FIGS. 6D-F are side, front, and perspective views, respectively, of an inner trough insert of the delivery subassembly of FIG. 6A.

FIG. 10 is a perspective view of a shaft and auger tip for expelling bone graft material according to an alternate embodiment of the invention.

FIG. 11A shows the distal end of an alternate embodiment of a delivery tube subassembly.

FIG. 11B is a schematic view of the delivery tube subassembly of FIG. 11A delivering bone graft to a facet joint.

DETAILED DESCRIPTION

As used herein, the term "proximal" refers to a location closer to a surgeon or other personnel using the device as described herein, while the term "distal" refers to a location farther away from the surgeon using the device.

Figure 1:
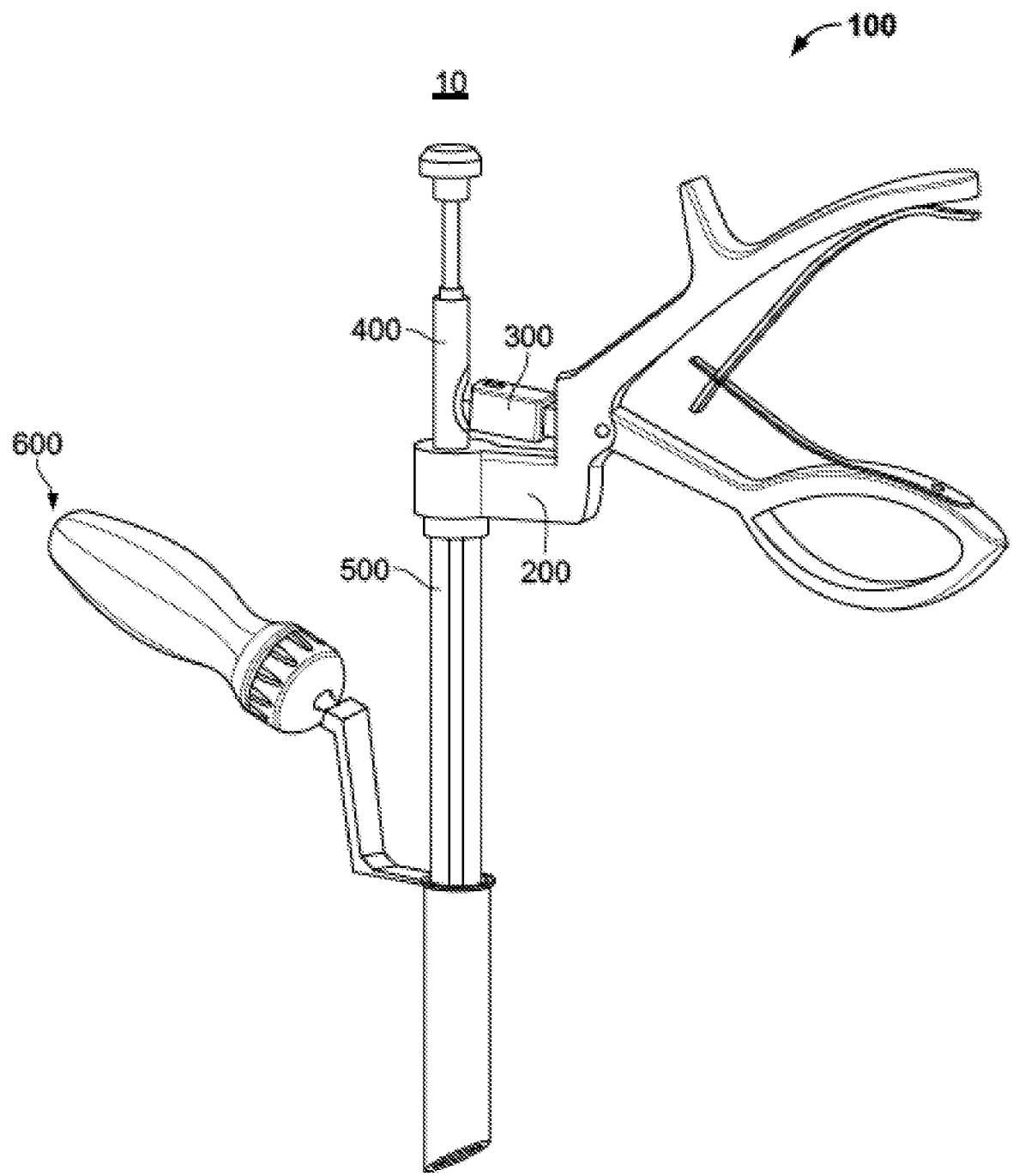
FIG. 1 is a perspective view of a bone graft delivery system according to the present invention.

A bone graft delivery system 10 is illustrated in FIG. 1 according to an embodiment of the disclosure. Generally, system 10 comprises an injector assembly 100 and an access portal assembly 600.

Figure 2:
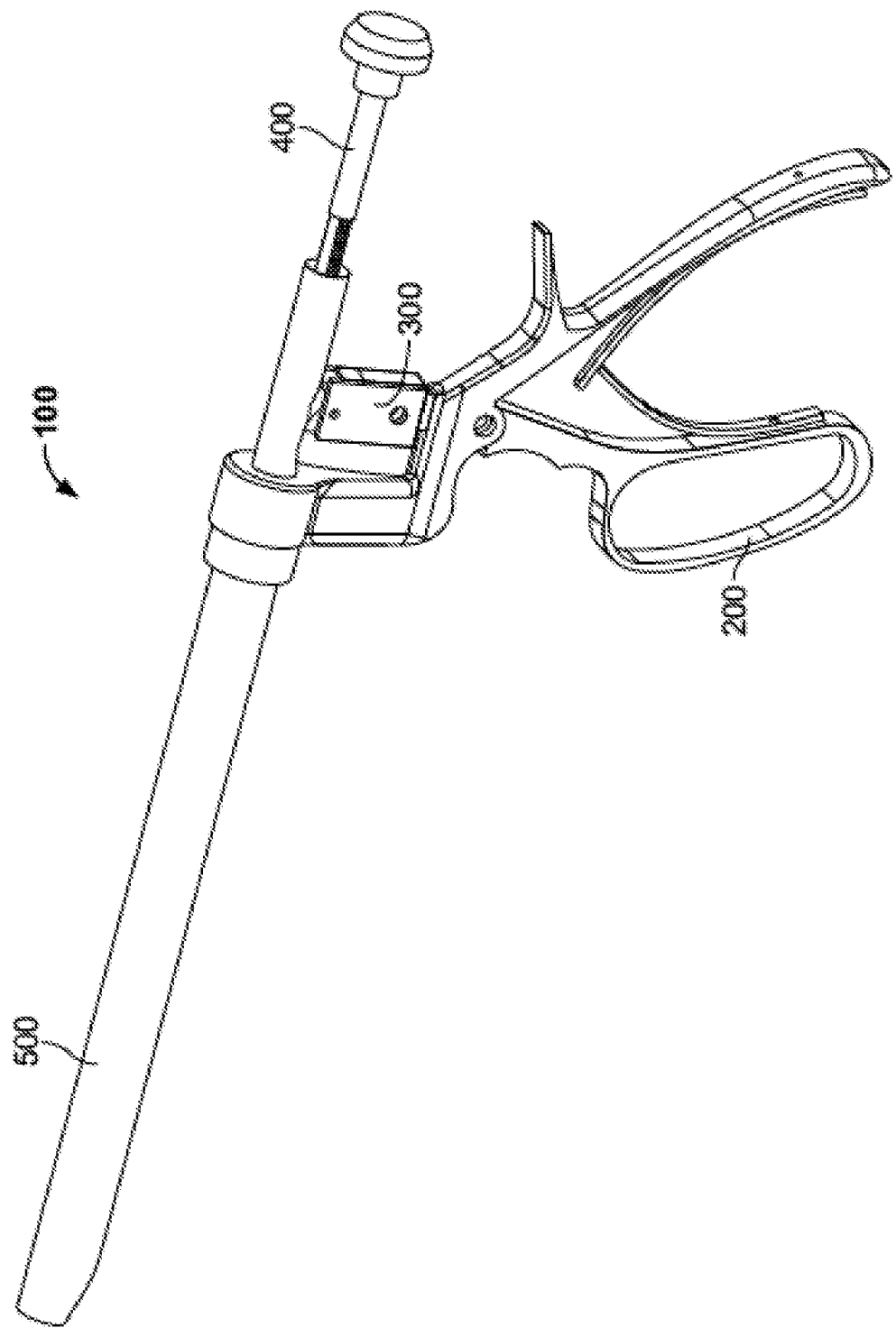
FIG. 2 is a perspective view of an injector assembly of the bone graft delivery system of FIG. 1.

Injector assembly 100, illustrated alone in FIG. 2, may include a number of subassemblies including, for example, a handle subassembly 200, a ratchet subassembly 300, a plunger subassembly 400, and a delivery tube subassembly 500. Handle subassembly 200 may be used to advance plunger subassembly 400 in an incremental or continuous fashion through delivery tube subassembly 500 to force a material out of a distal end thereof. For embodiments with incremental advancement of plunger subassembly 400, handle subassembly 200 and the plunger subassembly may work in conjunction with ratchet subassembly 300 to facilitate the incremental advancement.

Figure 3A:
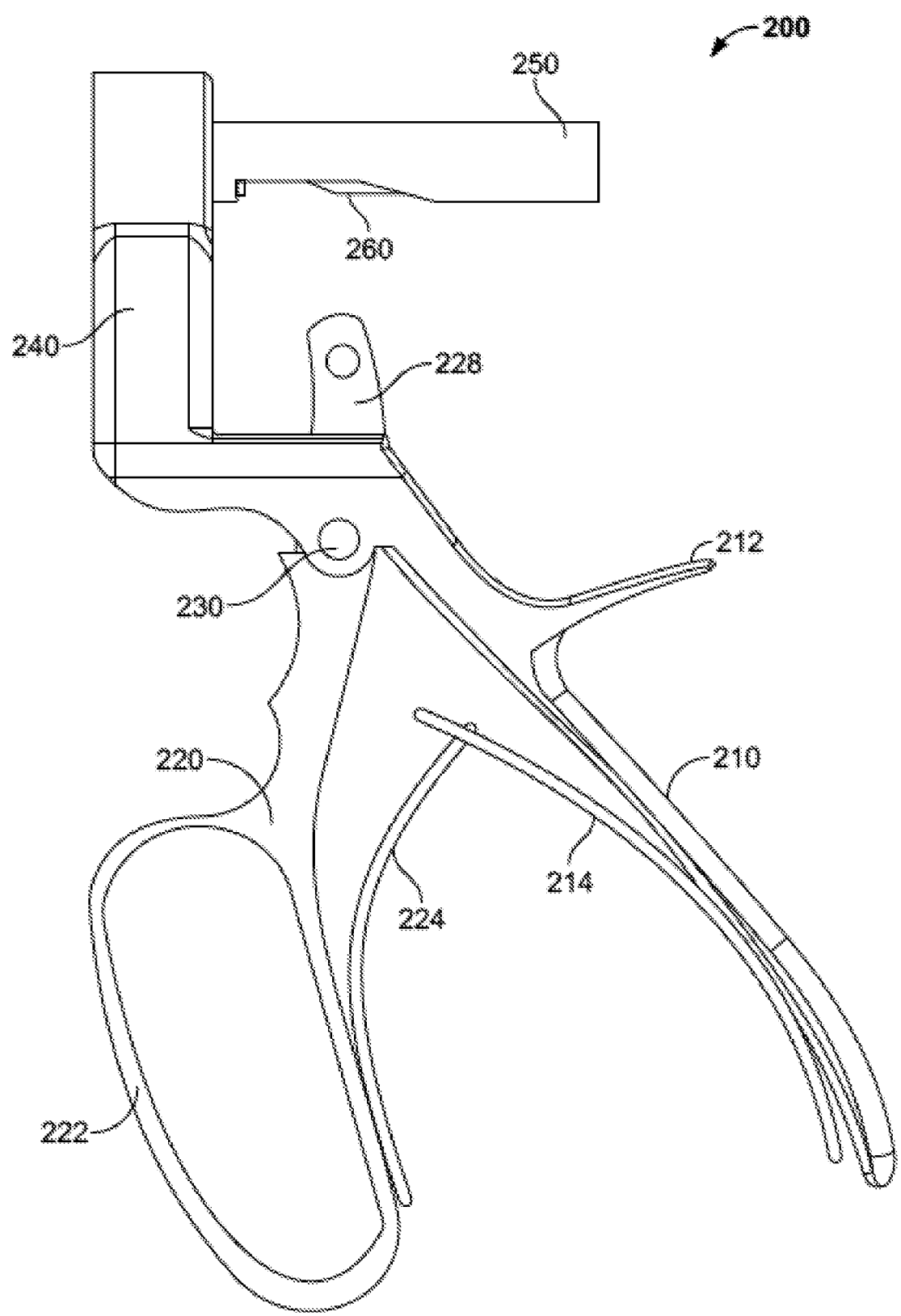
FIG. 3A is a side view of a handle subassembly of the injector assembly of FIG. 2.
Figure 3B:
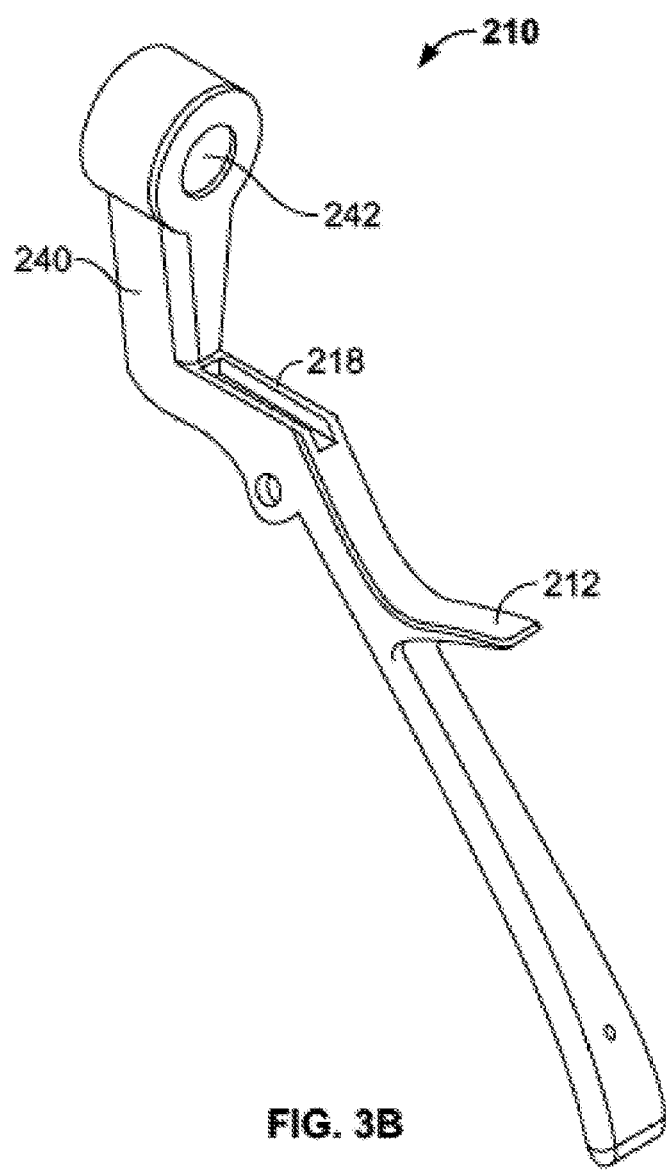
FIG. 3B is a perspective view of a fixed handle of the handle subassembly of FIG. 3A.
Figure 3C:
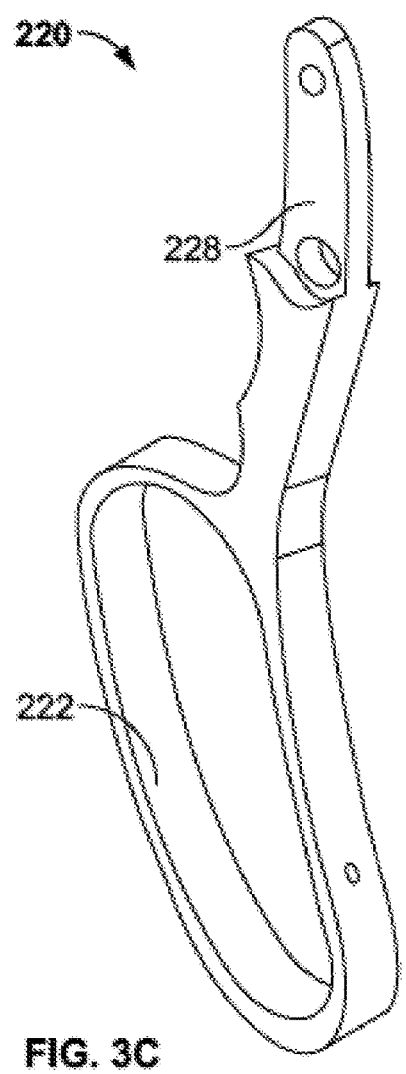
FIG. 3C is a perspective view of a moving handle of the handle subassembly of FIG. 3A.

Handle subassembly 200, illustrated in a constructed state in FIG. 3A, may include a fixed arm 210 (FIG. 3B) coupled to a moving arm 220 (FIG. 3C) by a fastener, for example a pivot pin 230. Fixed arm 210 may include a proximally projecting member 212 intended to be positioned between the thumb and forefinger of a user. Moving arm 220 may include a loop 222 to aid a user in squeezing the moving arm toward fixed arm 210. Moving arm 220 may also include a number of grooves and/or ridges (illustrated but not labeled) intended to facilitate positioning and comfort of a user's fingers.

Moving arm 220 may also include an upwardly extending member 228 configured to extend through a corresponding slot 218 in fixed arm 210. Slot 218 is preferably longer than the length of extension member 228 to provide clearance as moving arm 220 is moved toward or away from fixed arm 210 about pivot pin 230. Extension member 228 may include an aperture or other feature for connecting to ratchet subassembly 300, the structure and function of which is described in greater detail below.

Figure 3D:
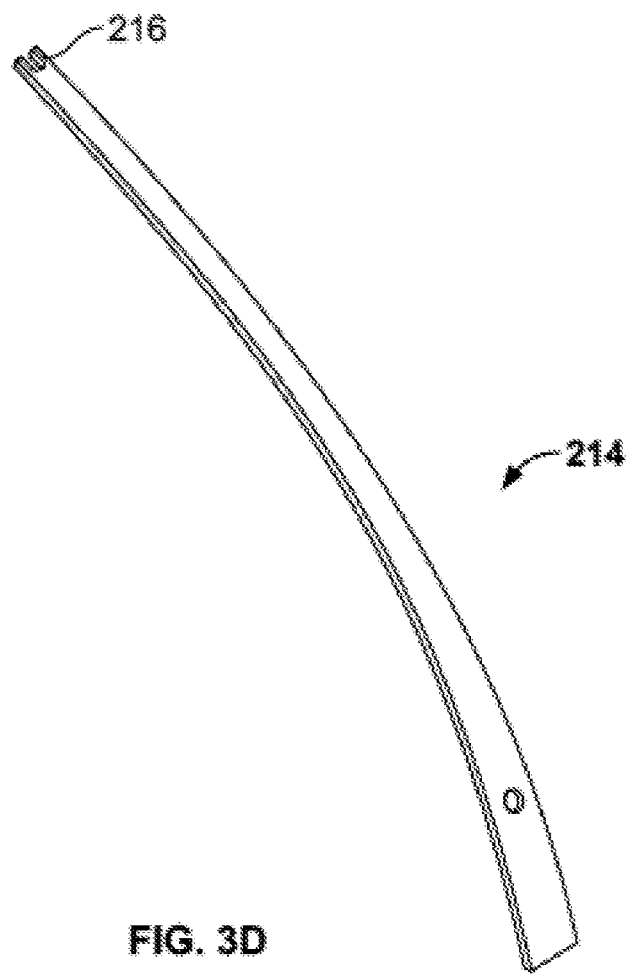
FIG. 3D is a perspective view of a fixed spring of the handle subassembly of FIG. 3A.
Figure 3E:
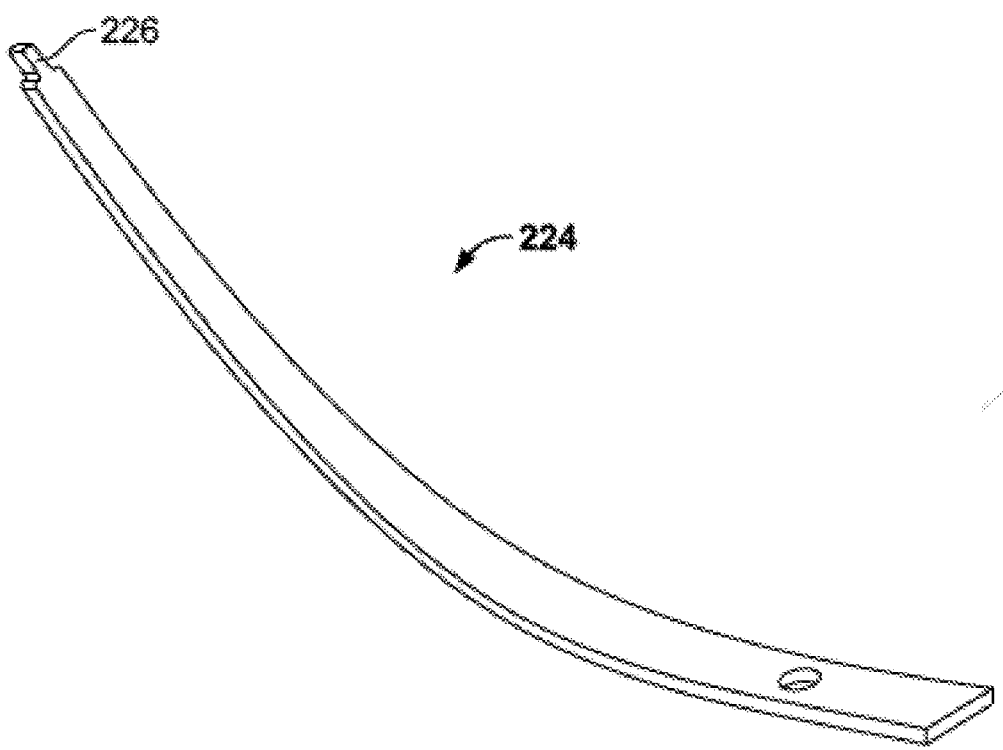
FIG. 3E is a perspective view of a moving spring of the handle subassembly of FIG. 3A.

Fixed handle 210 is preferably biased away from moving handle 220, about pivot pin 230, with one or more biasing members. For example, fixed handle 210 may include a fixed spring 214 (FIG. 3D) and moving handle 220 may include a moving spring 224 (FIG. 3E). Although the biasing members may take many suitable forms, as illustrated, fixed spring 214 is a generally curved member with a groove 216 formed at one end thereof. Similarly, moving spring 224, as illustrated, is a generally curved member with a tongue 226 formed at one end thereof. Tongue 226 may be configured to fit within groove 216 to couple fixed spring 214 to moving spring 224. The other ends of fixed and moving springs 214, 224 may be coupled to fixed and moving handles 210, 220 respectively, for example, by welding, fasteners, or any other suitable means.

Figure 3F:
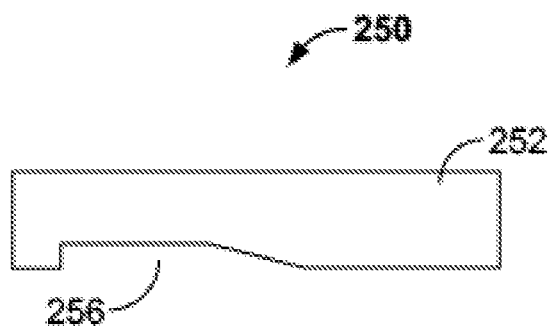
FIGS. 3F-G are side and perspective views, respectively, of an outer advancement member of the handle subassembly of FIG. 3A.
Figure 3G:
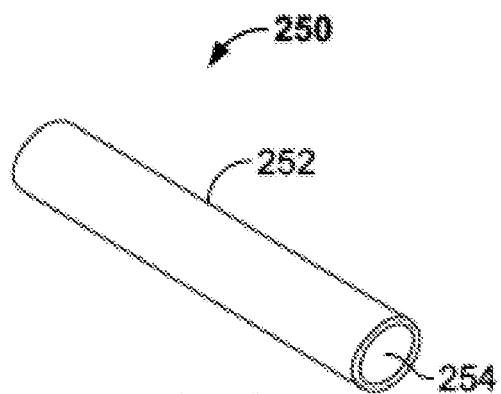
Figure 3H:
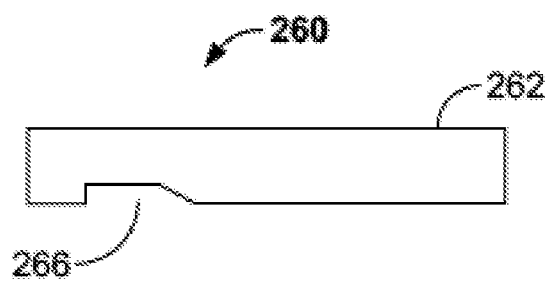
FIGS. 3H-I are side and perspective views, respectively, of an inner advancement members of the handle subassembly of FIG. 3A.
Figure 3I:
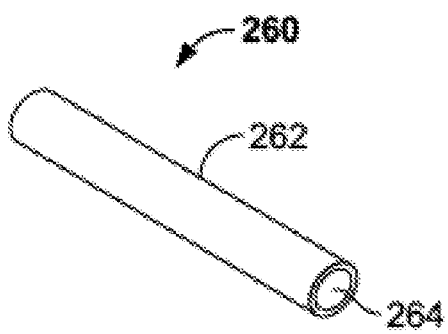

Fixed arm 210 may also include an upward extending member 240. Extension member 240 may include a central bore 242 sized and shaped to coupled with an outer advancement member 250 (FIGS. 3F-G) which houses an inner advancement member 260 (FIGS. 3H-I). Outer advancement member 250 may generally take the form of a cylindrical body 252 with a cylindrical channel 254 extending therethrough. A distal end of cylindrical body 252 may include a slot 256 on a bottom side thereof. Inner advancement member 260 may have a similar structure to outer advancement member 250. Namely, inner advancement member may have a cylindrical body 262 with a cylindrical channel 264 extending therethrough, with the cylindrical body sized to fit inside outer advancement member 250. A distal end of the cylindrical body 262 may include a slot 266 on a bottom side thereof. Slot 266 may have a similar shape and may be relatively shorter than slot 256. As is described below, slots 256, 266 function in conjunction with ratchet subassembly 300 for incremental advancement of plunger subassembly 400.

Figure 4A:
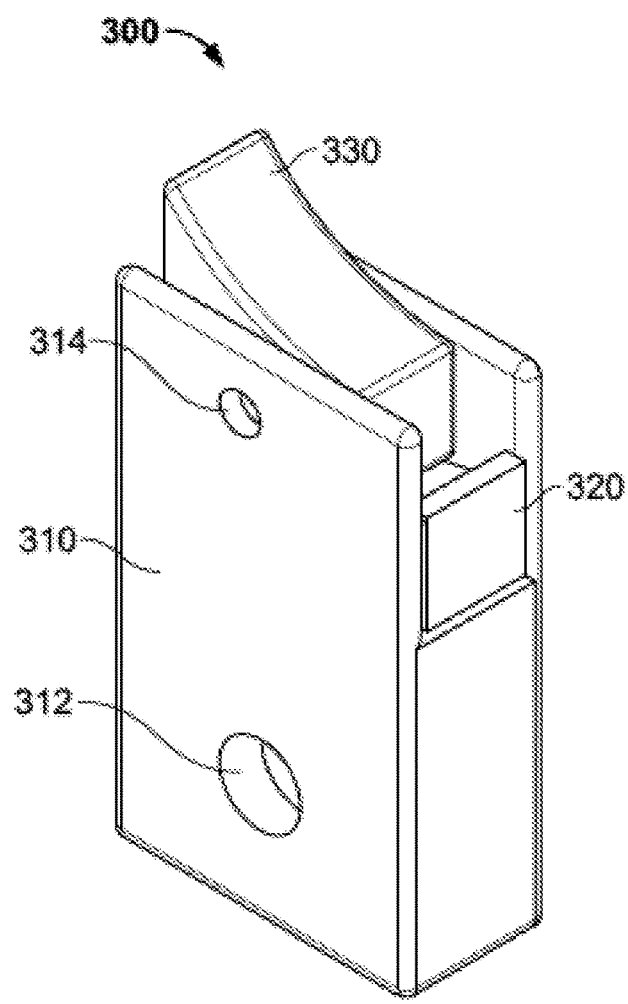
FIG. 4A is a perspective view of a ratchet subassembly of the injector assembly of FIG. 2.
Figure 4B:
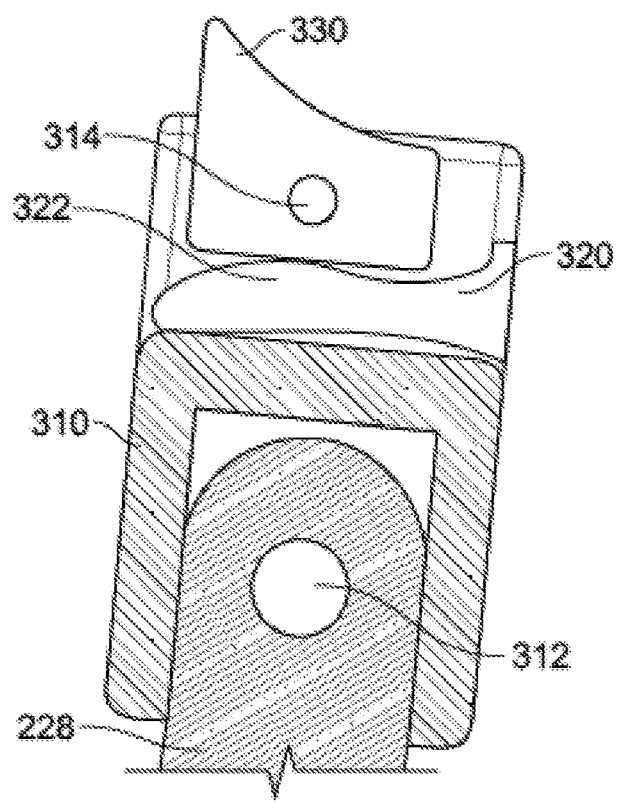
FIG. 4B is a cross-sectional view of the ratchet subassembly of FIG. 4A connected to the moving handle of FIG. 3C.

Ratchet subassembly 300 is illustrated in FIG. 4A. Generally, ratchet subassembly 300 includes a body 310, an articulation insert 320, and a pawl 330. Body 310 may be generally rectangular with first and second holes 312, 314 respectively. As illustrated in FIG. 4B, first hole 312 may be configured to align with a hole in the upwardly extending member 228 of moving arm 220. A fastener, such as a pin or a screw, may be used to couple the body 310 of ratchet subassembly 300 to moving arm 220. Second hole 314 may be configured to align with a hole in pawl 330. A fastener, such as a pin, may connected pawl 330 to body 310 through second hole 314 such that the pawl may rotate about the pin. As best illustrated in FIG. 4B, articulation insert 320 may include a rounded articulation surface 322. Articulation surface 322 may provide a limited range of rotation for pawl 330 in relation to articulation insert 320. As is described in more detail below, this limited articulation or rotation of pawl 330, in combination with structures in plunger subassembly 400, allows for incremental ratcheted advancement of the plunger subassembly.

All portions of handle subassembly 200 and ratchet subassembly 300 may be formed of materials suitable for use in surgery, including metals. Preferably, the materials are capable of being sterilized such that handle subassembly 200 and ratchet subassembly 300 may be reused.

Figures 5A, 5B:
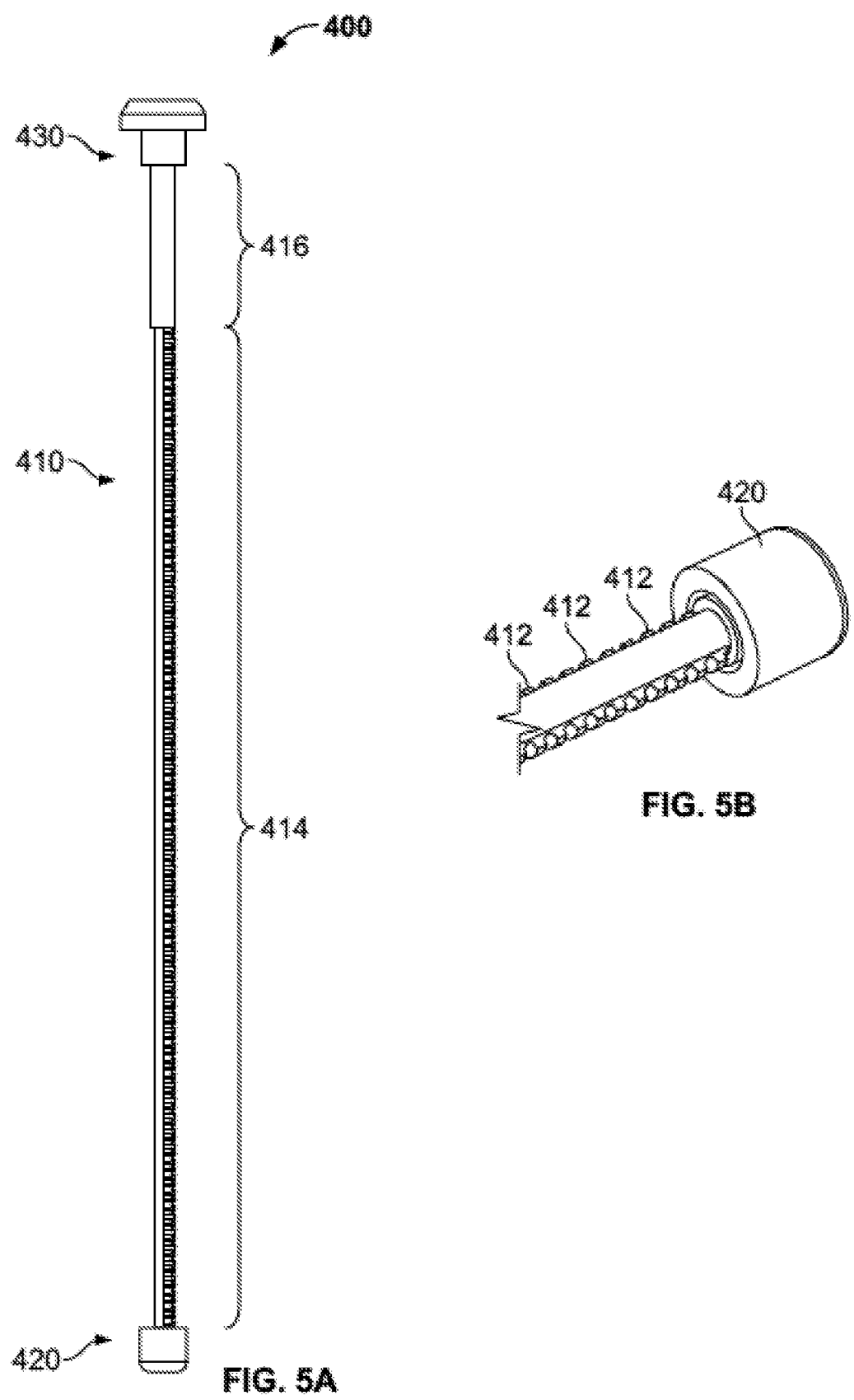
FIG. 5A is a side view of a plunger subassembly of the injector assembly of FIG. 2.
FIG. 5B is a perspective view of a shaft and plunger tip of the plunger subassembly of FIG. 5A.

Plunger subassembly 400 is illustrated in FIG. 5A. Generally, plunger subassembly includes a shaft 410, a plunger tip 420 at a distal end of the shaft, and a stopper 430 at a proximal end of the shaft. Shaft 410 may be generally cylindrical and may include structures, such as threading or teeth 412, on a portion of the shaft or on the entire shaft. As illustrated, shaft 410 includes a threaded or toothed distal portion 414 and an unthreaded or untoothed proximal portion 416. Teeth 412 near the distal end of shaft 410 are illustrated in greater detail in FIG. 5B. Shaft 410 may be formed of a suitable material, including metals, and preferably is capable of being sterilized and reused. Plunger tip 420 may be generally cylindrical and may be sized to fit snugly within a portion of delivery tube subassembly 500, which is described in greater detail below. Plunger tip 420 may be formed of a disposable plastic and may be removable from the distal end of shaft 410. The remaining portions of plunger subassembly 400 may be formed of a metal suitable for use in surgery, including metals that may be sterilized and reused, or may alternately be formed from a disposable material, including plastics suitable for use in surgery. Briefly, as handle subassembly 200 and ratchet subassembly 300 are used to incrementally advance plunger subassembly 400, and particularly plunger tip 420, the advancement of the plunger tip causes material within delivery tube subassembly 500 to be forced out from injector assembly 100 into the patient's body at a desired location. Stopper 430 may be generally cylindrical and sized such that it is too large to pass through the outer advancement member 250 of handle assembly 200, providing a limit to how far plunger subassembly 400 may be advanced with respect to delivery tube subassembly 500.

Figure 6A:
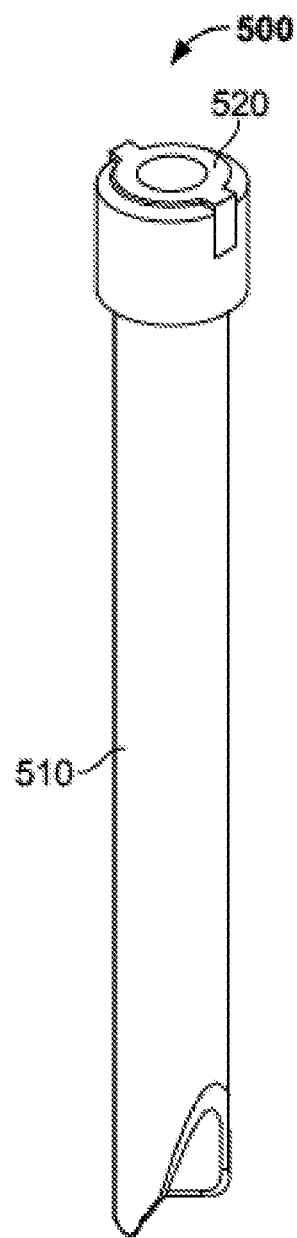
FIG. 6A is a perspective view of a delivery tube subassembly of the injector assembly of FIG. 2.
Figure 6B:
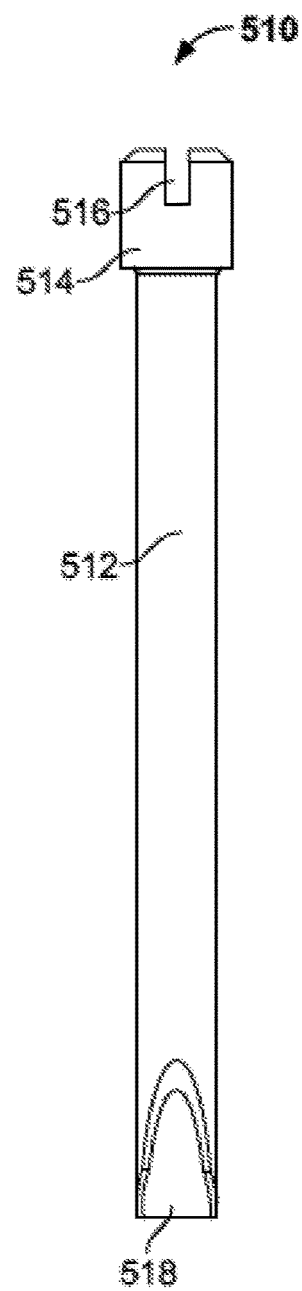
FIGS. 6B-C are front and perspective views, respectively, of an outer graft tube of the delivery tube subassembly of FIG. 6A.
Figure 6C:
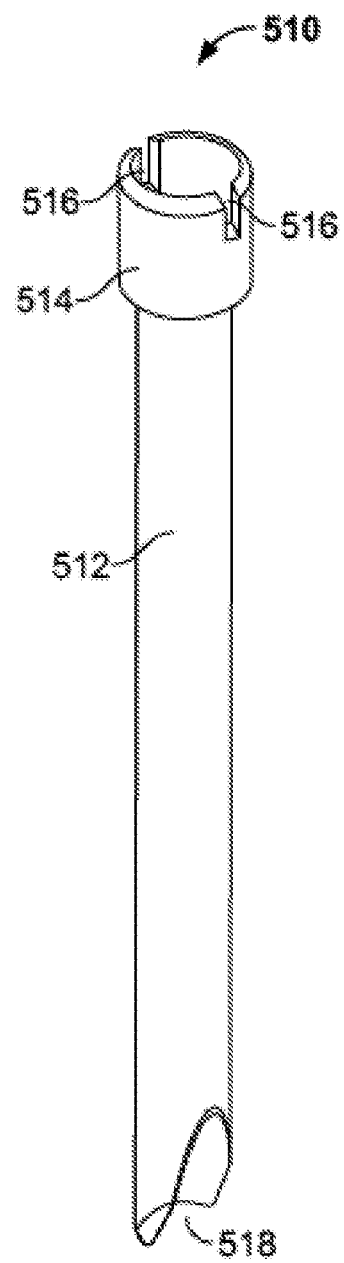

Delivery tube subassembly 500 is illustrated in FIG. 6A. Generally, delivery tube subassembly 500 includes an outer cannula or graft tube 510 and an inner cannula or trough insert 520. Graft tube 510 is illustrated in greater detail in FIGS. 6B-C. Graft tube 510 may include a generally hollow cylindrical body 512, a cap 514 with slots 516, and a delivery portion 518 at a distal end of the body. Cap 514 may be generally cylindrical with a larger diameter than body 512, and may include two generally rectangular slots 516 extending distally from a proximal end of the cap. Rectangular slots 516 may be positioned in a diametrically opposed relationship and be configured to lock with a portion of the trough insert 520. Delivery portion 518 at the distal end of body 512 may take the form or an uninterrupted hollow cylinder, or, as illustrated, may take the form of an interrupted hollow cylinder. For example, delivery portion 518 may take the form of a hollow cylinder with an off-axis exit portion in the general shape of a "U" cut around a portion of the circumference of the body. This configuration may be useful in facilitating off-axis expulsion of material through graft tube 510. Graft tube 510 may be formed from a disposable biocompatible plastic and may be color coded such that the graft tube is easily discernible from trough insert 520, described in greater detail below. Also, graft tube 510, and particularly the body 512 of the graft tube, may be translucent or transparent to allow a user to at least partially see components passing through the graft tube. Alternately, graft tube 510 may be formed of a metal suitable for surgery.

Trough insert 520 is illustrated in greater detail in FIGS. 6D-F. Trough insert 520 may include a generally hollow body 522 and a cap 524 with tabs 526. Body 522 may take the form, for example, of a trough, a clamshell, or an elongated partially cylindrical body. In other words, body 522 may take the form of a cylinder that has a planar cut extending longitudinally across the body. As illustrated, a section of body 522 forms more than half a circle, although a section of the body could form exactly half a circle, or less. Other variations may also be provided. Cap 524 may take the general form of an entire hollow cylinder, and may include two diametrically opposed generally rectangular tabs 526 extending radially outward from the cap and configured to be inserted into slots 516 of the cap 514 of graft tube 510. When trough insert 520 is inserted into graft tube 510, as illustrated in FIG. 6A, tabs 526 mate with slots 516 such that the trough insert is rotatably locked with respect to the graft tube, and the trough insert is restricted from moving distally with respect to the graft tube. The trough insert 520 may also be formed from a disposable biocompatible plastic and may be color coded with a different color than graft tube 510 such that the trough insert is easily discernible from graft tube. Also, trough insert 520, and particularly the body 522 of the trough insert, may be translucent or transparent to allow a user to at least partially see components passing through the trough insert. Alternately, trough insert 520 may be formed of a metal suitable for surgery. The body 522 of trough insert 520 may also include indicia, such as laser markings, denoting volume of a material, such as bone graft material within the trough insert.

The inner surface of trough insert 520 may be highly polished, buffed, or otherwise smoothed. This may be particularly effective if trough insert 520 is formed of a metal. When bone graft is packed into a delivery device such as trough insert 520, it may have a tendency to expand, particularly at the leading edge of the material, as it is being expelled from the delivery device. If the bone graft is advanced through a highly polished, buffed, or otherwise smoothed surface, however, friction may be reduced, facilitating the ease and evenness with which the bone graft advances through the delivery device.

Figure 7A:
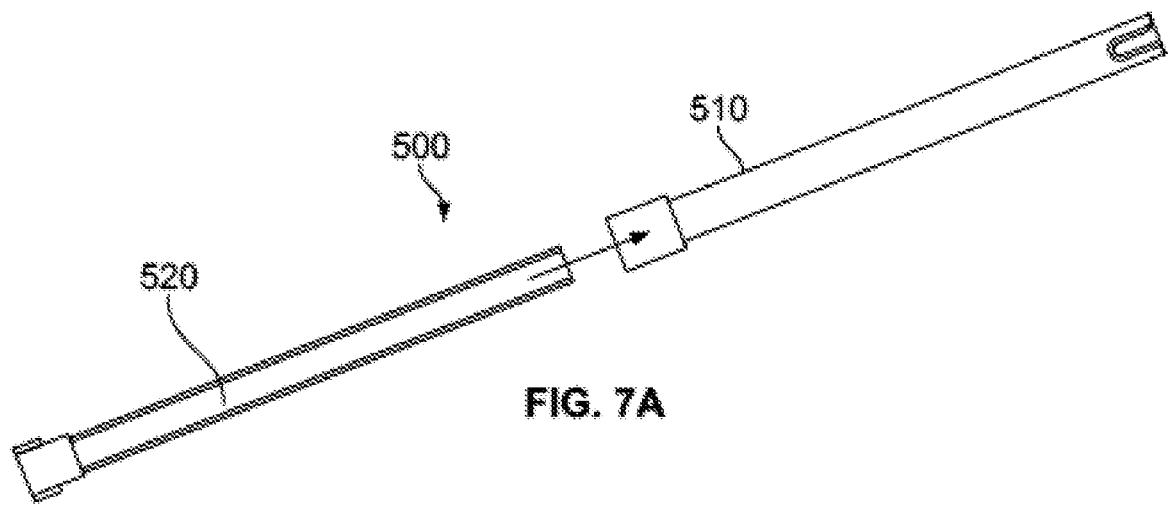
FIGS. 7A-C illustrate the inner trough insert of FIGS. 6D-F being inserted into the outer graft tube of FIGS. 6B-C at different stages of insertion.
Figure 7B:
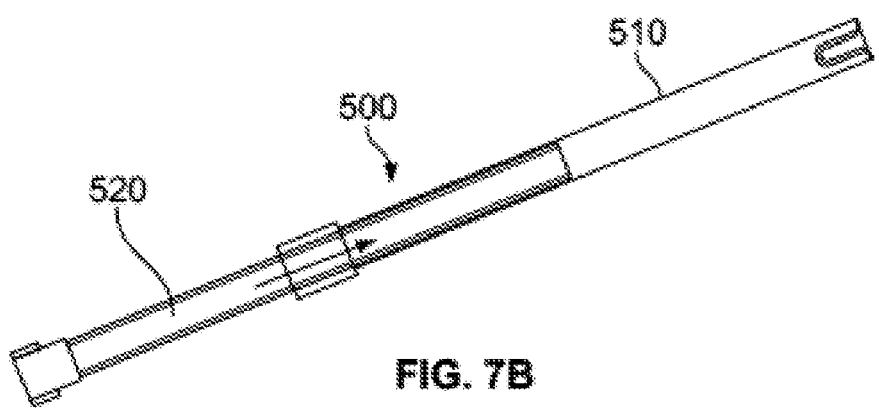
Figure 7C:
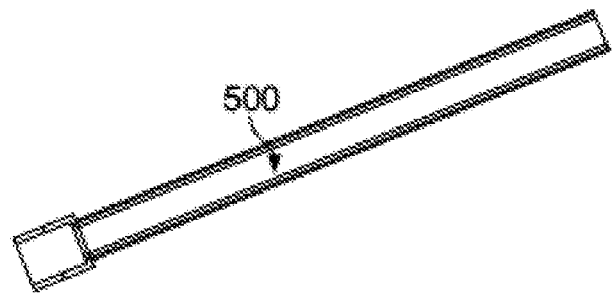

To prepare the injector prior to use, the handle subassembly 200 and ratchet subassembly 300 are assembled together. Of course, both handle subassembly 200 and ratchet subassembly 300 may be provided to a user pre-assembled. Trough insert 520 is packed with a material, such as a bone graft material. As noted above, the term "bone graft" as used herein refers to bone graft, bone graft substitute, or a mixture thereof. One example of a suitable bone graft substitute material may be Vitoss® Bone Graft Substitute, Vitoss® Bioactive Foam Back Bone Graft Substitute, or other products in the Vitoss® line sold by Stryker Corp. Examples of suitable bone graft materials are described in greater detail in U.S. Pat. Nos. 7,534,451, 6,383,519 and 6,521,246 and in U.S. Patent Publication No. 2005/0288795, the disclosures of which are both hereby incorporated by reference herein. The bone graft material may be hand-packed into trough insert 520 and preferably does not exceed the walls of body 522. If packed such that the material does not exceed the walls of body 522, a volume of space remains between the packed material and the inner diameter of graft tube 510. If the material expands during expulsion, as described above, the additional empty volume provides space into which the material may expand. Once loaded with material, trough insert 520 may be inserted into graft tube 510 until the trough insert locks into the graft tube. Delivery subassembly 500 is illustrated in FIGS. 7A-C at progressive stages of insertion of trough insert 520 into graft tube 510.

Figure 7D:
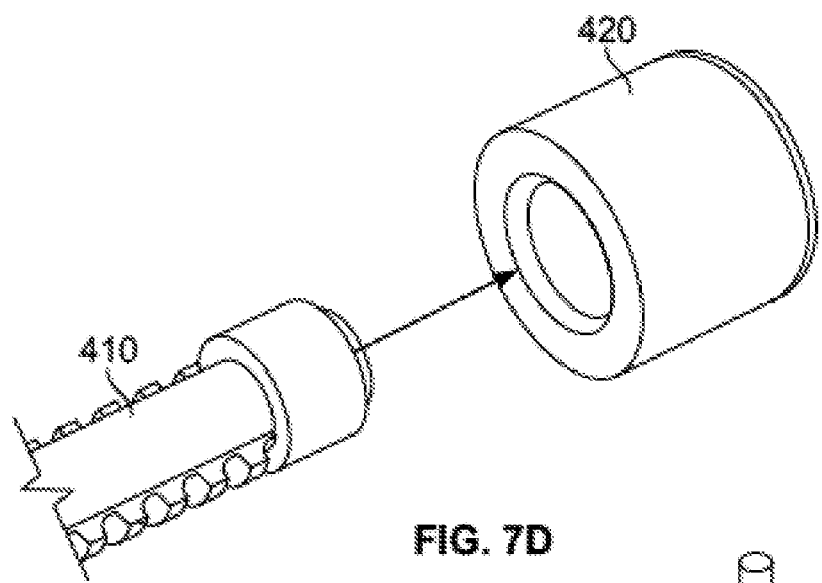
FIGS. 7D is a perspective view of the shaft of FIG. 5B being inserted into the plunger tip of FIG. 5B.
Figure 7E:
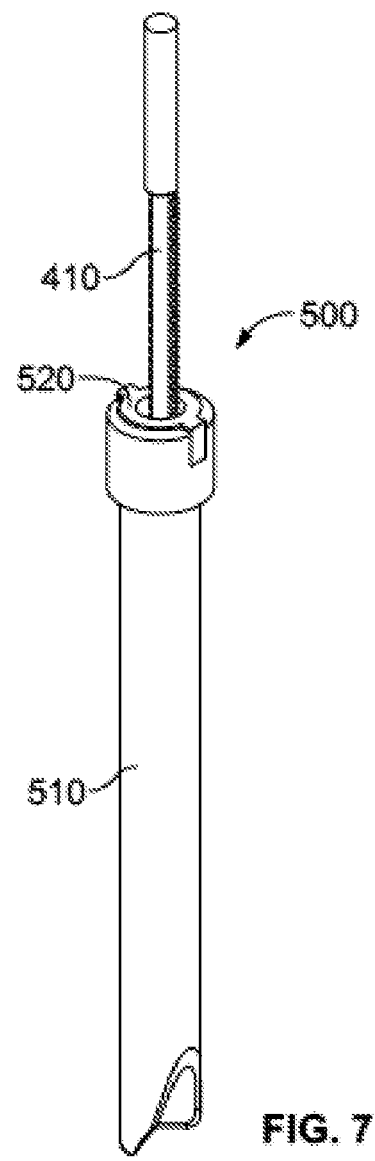
FIG. 7E is a perspective view of the plunger subassembly of FIG. 5A being inserted into the delivery tube subassembly of FIG. 6A.
Figure 7F:
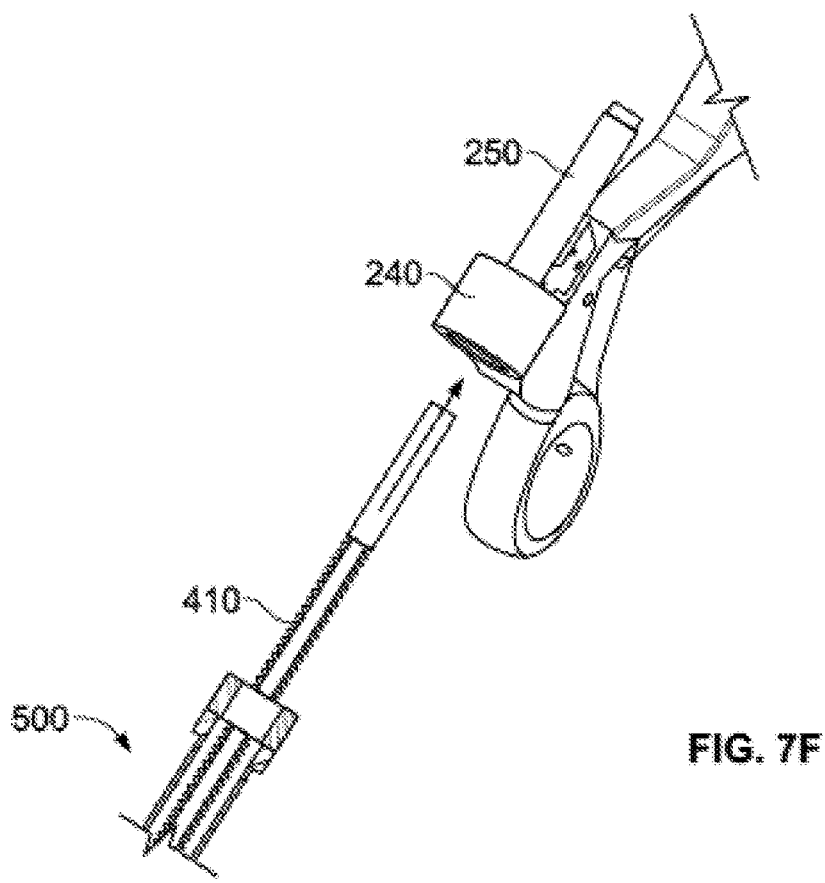
FIG. 7F is a perspective view of the plunger subassembly and delivery tube subassembly of FIG. 7E being inserted into the handle subassembly of FIG. 3A.
Figure 7G:
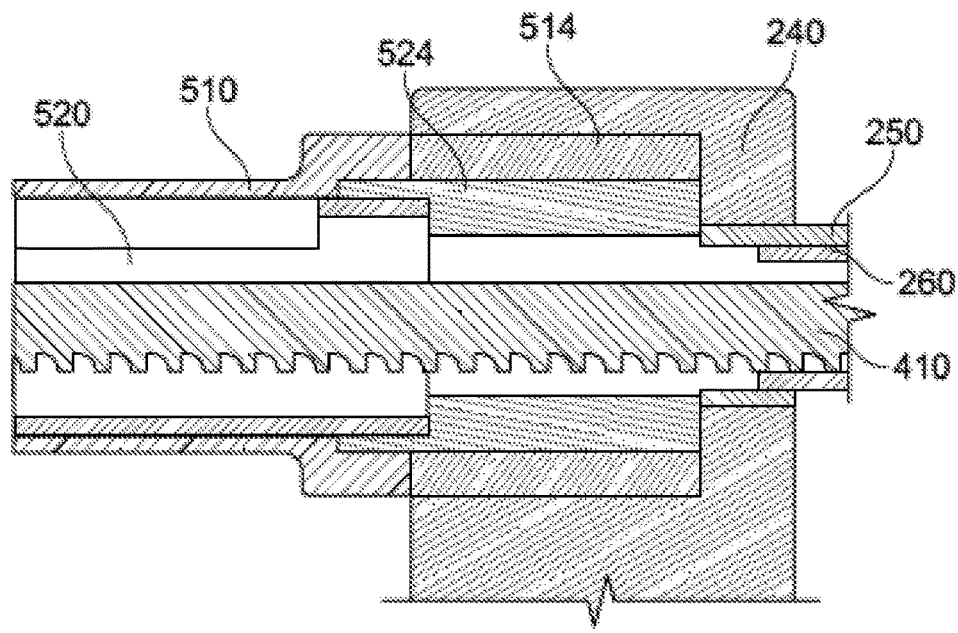
FIG. 7G is a cross-sectional view of the plunger subassembly and delivery tube subassembly of FIG. 7F fully inserted into the handle subassembly of FIG. 3A.
Figure 7H:
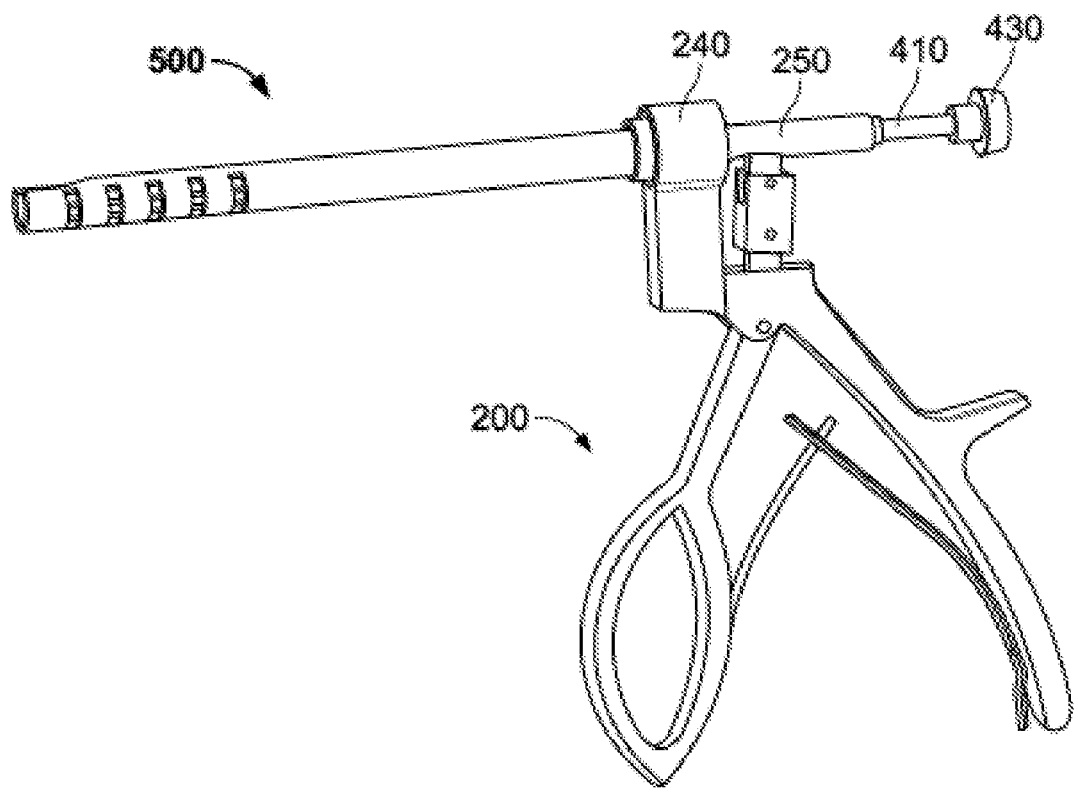
FIG. 7H is a perspective view of the injector plunger subassembly and delivery tube subassembly inserted in the handle subassembly with a stopper connected to the shaft of the plunger subassembly.

Once delivery tube subassembly 500 is assembled and filled with the desired material, plunger tip 420 may be connected to the distal end of the shaft 410 of plunger subassembly 400, as illustrated in FIG. 7D. Once connected, the plunger tip 420 and shaft 410 of plunger subassembly 400 are inserted through the proximal end of trough insert 520, which is located inside graft tube 510, as illustrated in FIG. 7E. The proximal end of shaft 410 is then moved proximally through the outer and inner advancement members 250, 260, which are mated to the upward extending member 240 of fixed arm 210, as shown in FIG. 7F. As illustrated in FIG. 7G., the shaft 410 and delivery tube subassembly 500 are moved proximally until the caps 514, 524 of the graft tube 510 and trough insert 520, respectively, are each flush with an inside surface of the upward extending member 240 of fixed handle 220. In this position, the proximal end of shaft 410 extends through outer and inner advancement members 250, 260. Also in this position, one or more teeth 412 of shaft 410 are exposed through slots 256, 266 of the outer and inner advancement members 250, 260, the slots aligning with one another. Preferably, the shaft 410 of plunger subassembly 400 fits snugly within inner advancement member 260. Once in this position, stopper 430 may then be coupled to the proximal end of shaft 410, as illustrated in FIG. 7H.

Figure 7I:
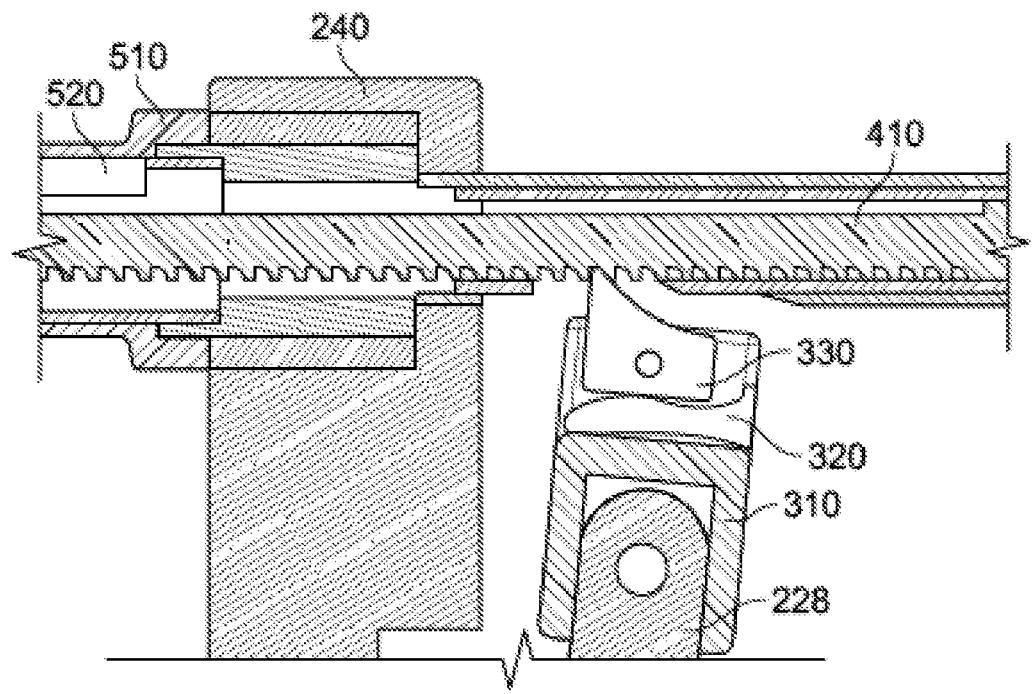
FIG. 7I is a cross sectional view of the injector assembly of FIG. 2 during ratcheting movement of the plunger subassembly.

With all components of injector assembly 100 in place and with the desired material loaded into trough insert 520, the material may be expelled from graft tube 510 by incremental advancement of the shaft 410 and plunger tip 420 of plunger subassembly 400. By squeezing the moving arm 220 of handle subassembly 200 toward fixed arm 210, the upward extending member 228 of the moving arm is moved distally by virtue of the pivot connection between the fixed and moving arms. This, in turn, moves ratchet subassembly distally or forward. As the body 310 of ratchet subassembly 300 moves forward, articulation insert 320 and pawl 330 also move forward. As illustrated in FIG. 7I, a tip of pawl 330 is located between two teeth 412 or between successive threads of shaft 410. Preferably, the proximal side of each tooth 412 is relatively flat and the distal side of each tooth is relatively curved. Similarly, preferably the tip of pawl 330 has a relatively flat distal side and a relatively curved proximal side. As the pawl 330 of ratchet assembly 300 moves forward, the flat distal side of the tip of the pawl presses against the flat proximal side of a tooth 412. Pawl 330 may articulate slightly during this forward motion with respect to articulation insert 320, but not so much that the tip of the pawl clears the teeth 412. As such, the forward motion of pawl 330 forces the shaft 410 of plunger subassembly 400 forward. As the shaft 410 of plunger subassembly 400 moves forward, plunger tip 420 also moves forward, pushing an amount of material loaded in trough insert 520 out of the distal end of graft tube 510.

As the user releases his grip on moving arm 220, springs 214, 224 force the moving arm away from fixed arm 210. As fixed and moving arm 210, 220 move away, ratchet subassembly 300 is moved proximally or backward. Because of the configuration of the articulation surface 322 of articulation insert 320, and also because of the rounded configuration of the proximal side of the tip of pawl 330 and the rounded configuration of the distal side of teeth 412, as the pawl moves backward, it articulates enough with respect to the articulation insert to clear the teeth. As the moving handle 220 is fully released, pawl 330 moves proximally with respect to one or more teeth 412. In this position, the moving handle 220 may again be squeezed, causing another incremental forward movement of shaft 410 and plunger tip 420, causing an incremental expulsion of the material loaded in the trough insert 510. The teeth 412, ratchet subassembly 300, and handle subassembly 200 may be configured such that one full squeeze and full release of moving handle 220 causes pawl 330 to advance shaft 410 by a given number of teeth. This process may be repeated until the desired amount of material has been expelled from the delivery tube subassembly 500, or until the stopper 430 of plunger subassembly 400 abuts the proximal end of the outer and inner advancement members 250, 260. Among other benefits, this configuration allows a user to expel a small, known quantity of material from injector assembly 100, which process may be repeated using only one hand at least in part because the moving arm 220 resets itself with respect to the fixed arm 210 once the user's squeezing force is released.

Figure 8A:
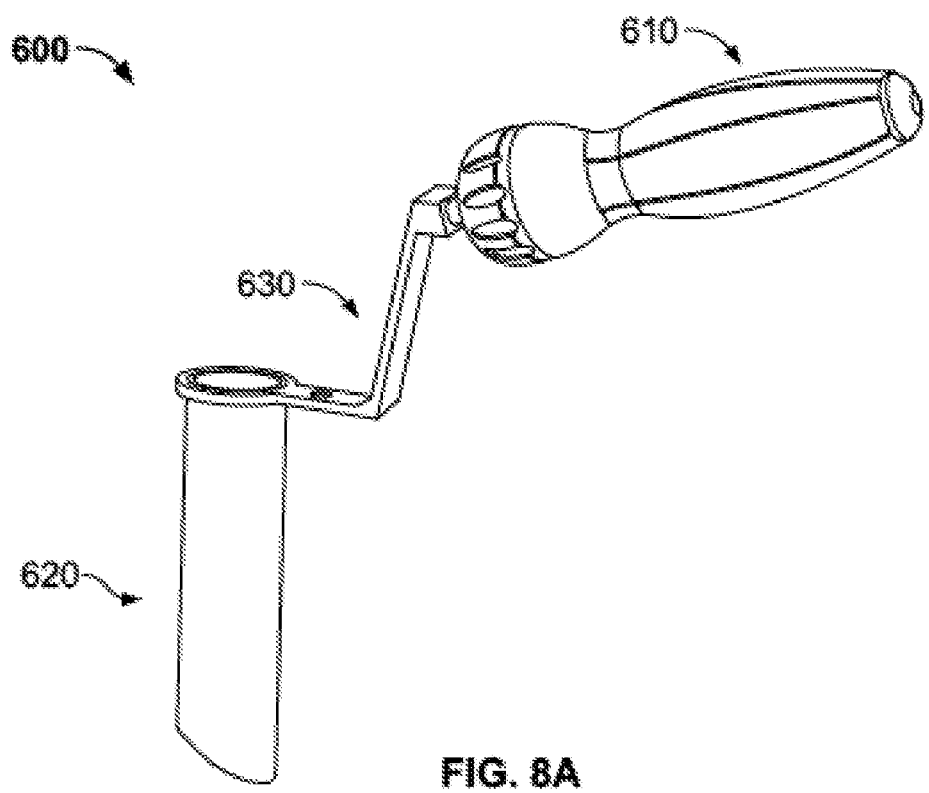
FIGS. 8A-C are perspective and side views of an access portal assembly of the bone graft delivery system of FIG. 1.
Figure 8B:
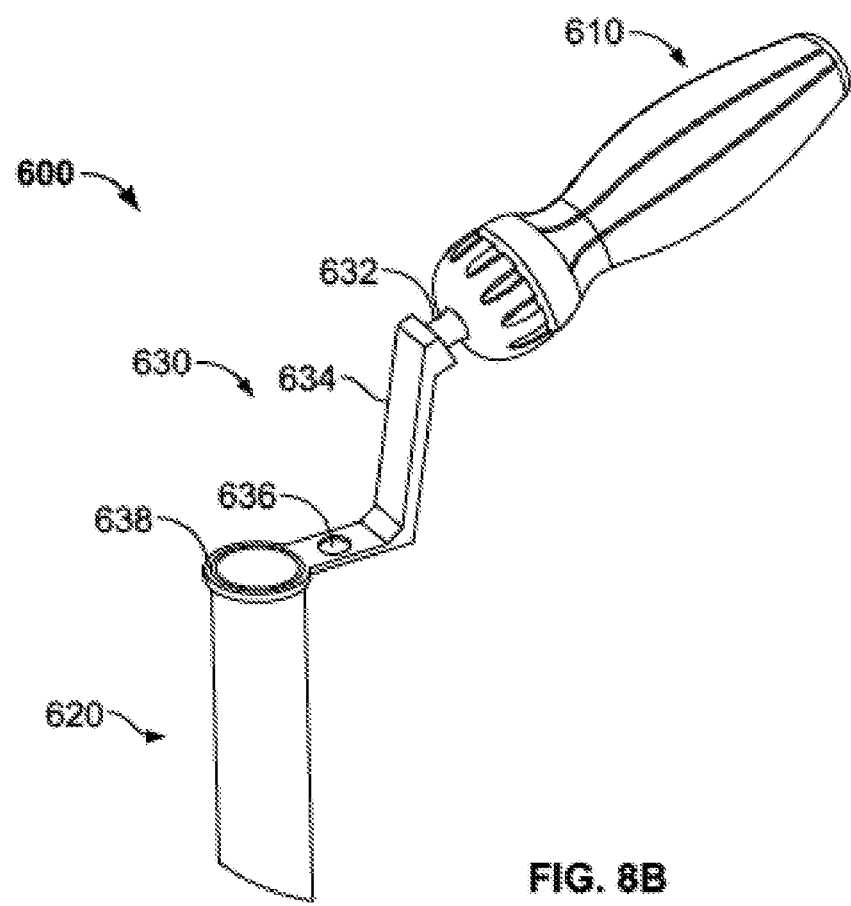

Bone graft delivery system 10 may also include an access portal assembly 600, as illustrated in FIGS. 8A-B, to provide access to the desired site of use of injector assembly 100. Access portal assembly 600 may generally include a device handle 610, an access tube 620, and an access tube handle 630. Device handle 610 preferably has an ergonomic design and is configured for use with a single hand, allowing a user to freely manipulate access portal assembly 600 in space, including when inserted into a surgical site.

Figure 8C:
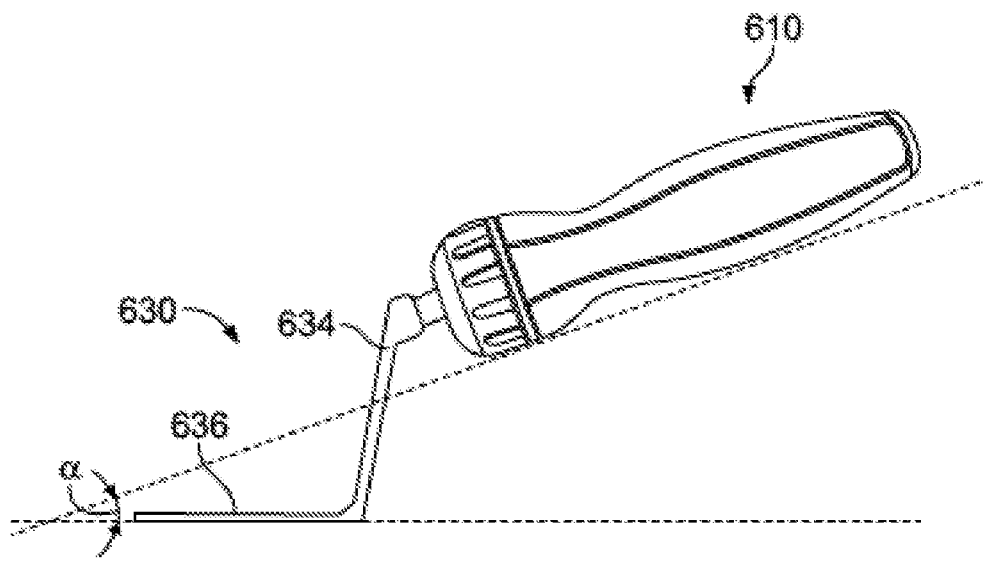
Figure 8D:
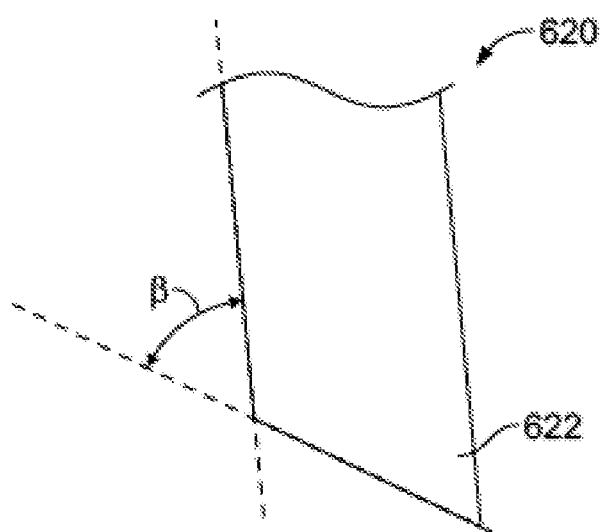
FIG. 8D is a side view of a distal end of the access portal assembly of FIGS. 8A-C.

Access tube handle 630 generally includes a handle connecting end 632, a proximal arm 634, a distal arm 636, and a tube connecting end 638. Handle connecting end 632 provides for a connection between access tube handle 630 and device handle 610. Tube connecting end 638 provides a connection between access tube handle 630 and access tube 620. Access tube 620 may extend generally perpendicular to tube connecting end 638. In one example, tube connecting end 638 take the general shape of a circle that has a compression fit, snap fit, or other fit with a proximal end of access tube 620. Proximal and distal arms 634, 636 may each be relatively straight, but angled with respect to one another. For example, proximal arm 634 may be angled at approximately 90 degrees, or slightly greater than 90 degrees, for example between approximately 90 degrees and approximately 110 degrees, with respect to distal arm 636. As illustrated in FIG. 8C, an axis parallel to distal arm 636 may form an angle α with respect to an axis parallel to a longitudinal axis of device handle 610, the angle α preferably being between approximately 10 degrees and approximately 30 degrees, more preferably being approximately 20 degrees. An angle α of approximately 20 degrees may be particularly useful for allowing sufficient articulation of access tube 620 by manipulating device handle 610, and access tube handle 630 by extension, while the device handle and the access tube handle extend above the surface of a patient's skin. As should be apparent, access tube 620, which is configured to allow passage of devices therethrough, including delivery tube subassembly 500, should have an inner diameter that is larger than an outer diameter of the delivery tube subassembly. Further, as illustrated in FIG. 8D, a distal end of access tube 620 may include a beveled edge 622. As illustrated, beveled edge 622 may form an angle 13 with an outer wall of access tube 620, the angle being between approximately 20 degrees and approximately 40 degrees, preferably approximately 30 degrees. An angle 13 of approximately 30 degrees may help facilitate sufficient engagement to a facet of the spine during a surgical procedure.

Figure 9A:
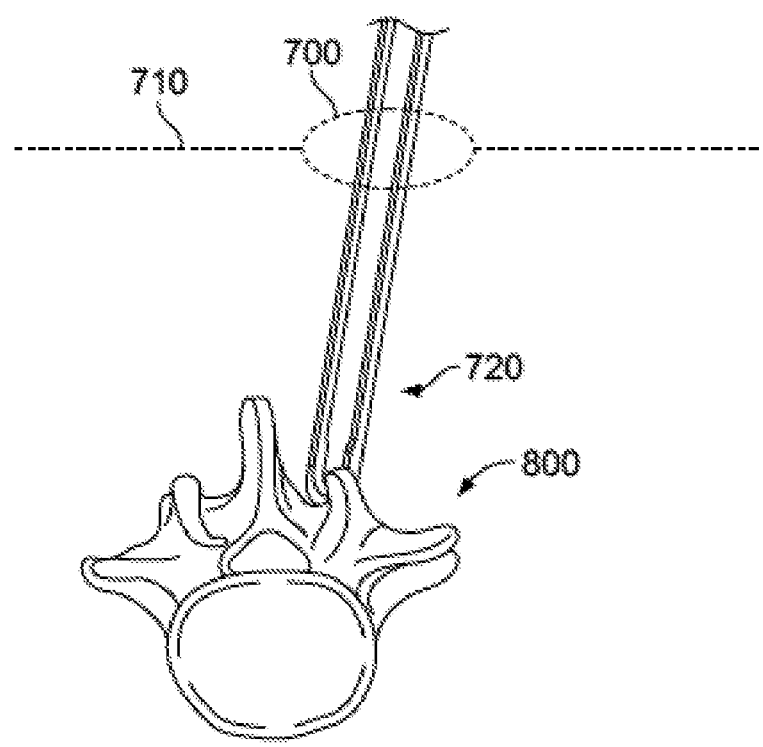
FIGS. 9A-B represent an incision being made in a patient to access the spine.
Figure 9B:
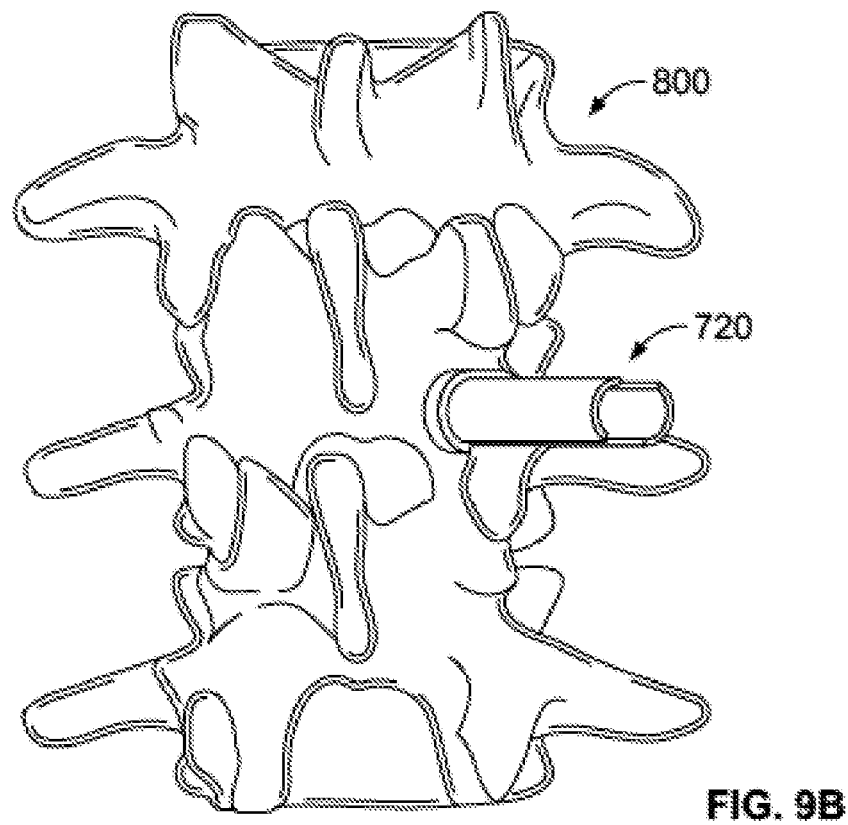
Figure 9C:
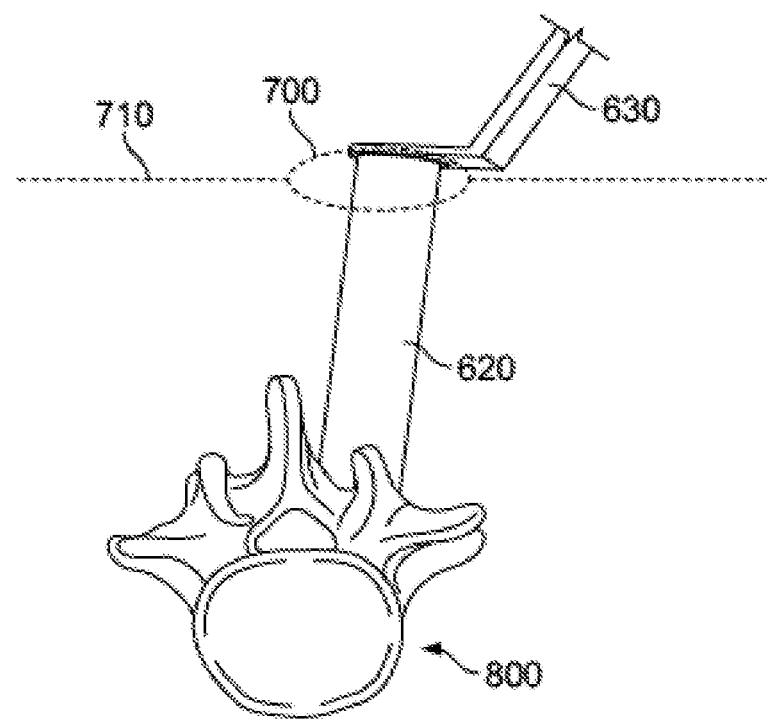
FIGS. 9C-D show the access portal assembly inserted through the incision toward the spine.
Figure 9D:
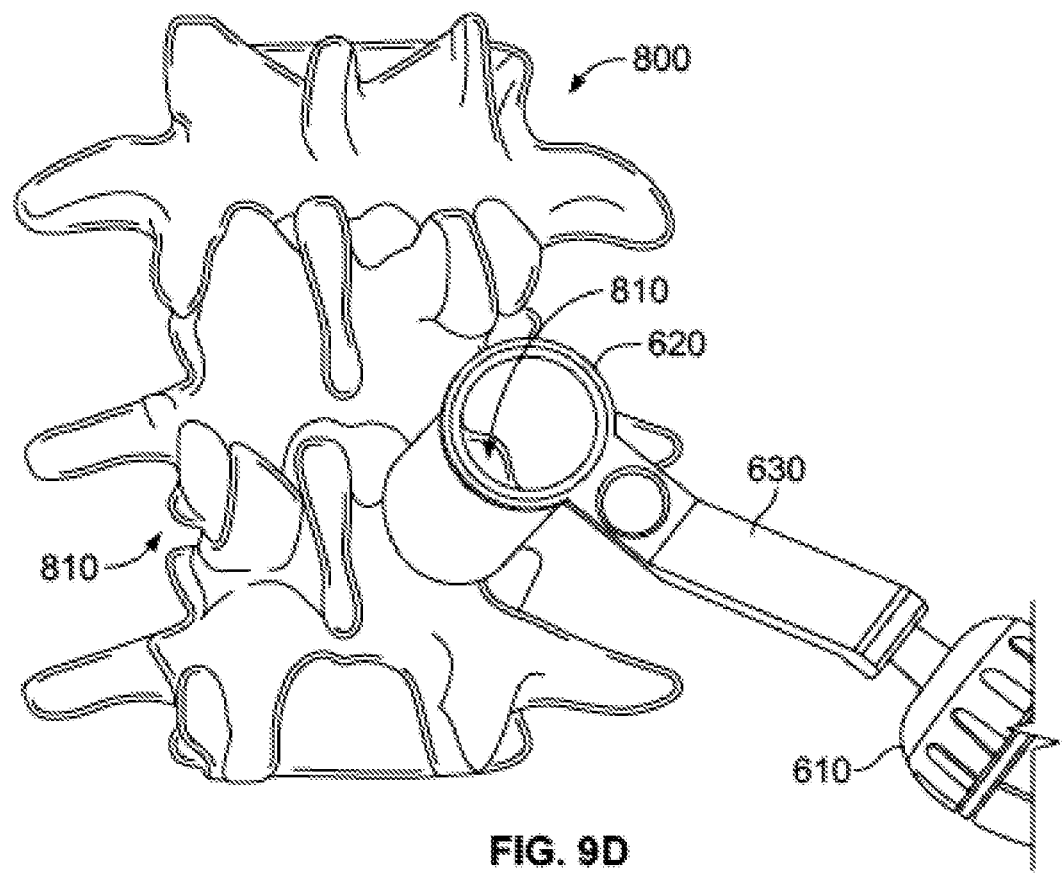

In one exemplary procedure, bone graft delivery system 10 may be used to facilitate spinal fusion along with pedicle screw implantation. In a first step of the spinal fusion procedure, as illustrated in FIG. 9A-B, an incision 700 is made in the skin 710 of a patient for eventual access to the spine 800. A pedicle screw 720 is illustrated connected to spine 800 through incision 700, but it should be noted that this is only to illustrate that a single incision may be made for both bone graft delivery system 10 and the pedicle screw, and the pedicle screw preferably would not be implanted until later in the procedure, as described below. Once incision 700 has been made in skin 710, the incision is dilated and the access tube 620 of access portal assembly 600 is placed into the incision, as shown in FIGS. 9C-D. As described above, the configuration of components of access portal assembly 600, including the ergonomic device handle 610 and angled access tube handle 630 facilitates a user handling, manipulating, and/or positioning the access tube assembly with a single hand. After expanding incision 700 through the use of, for instance, sequential dilators, access tube assembly 600 is advanced until it reaches the desired facet joint 810, and articulated, rotated, or otherwise repositioned into a desired position with relation to the facet joint. At this point, a cutting tool, such as a rasp, may be inserted through the access tube 620 of access portal assembly 600 and the facet joint 810 may be cut or otherwise prepared as desired.

Figure 9E:
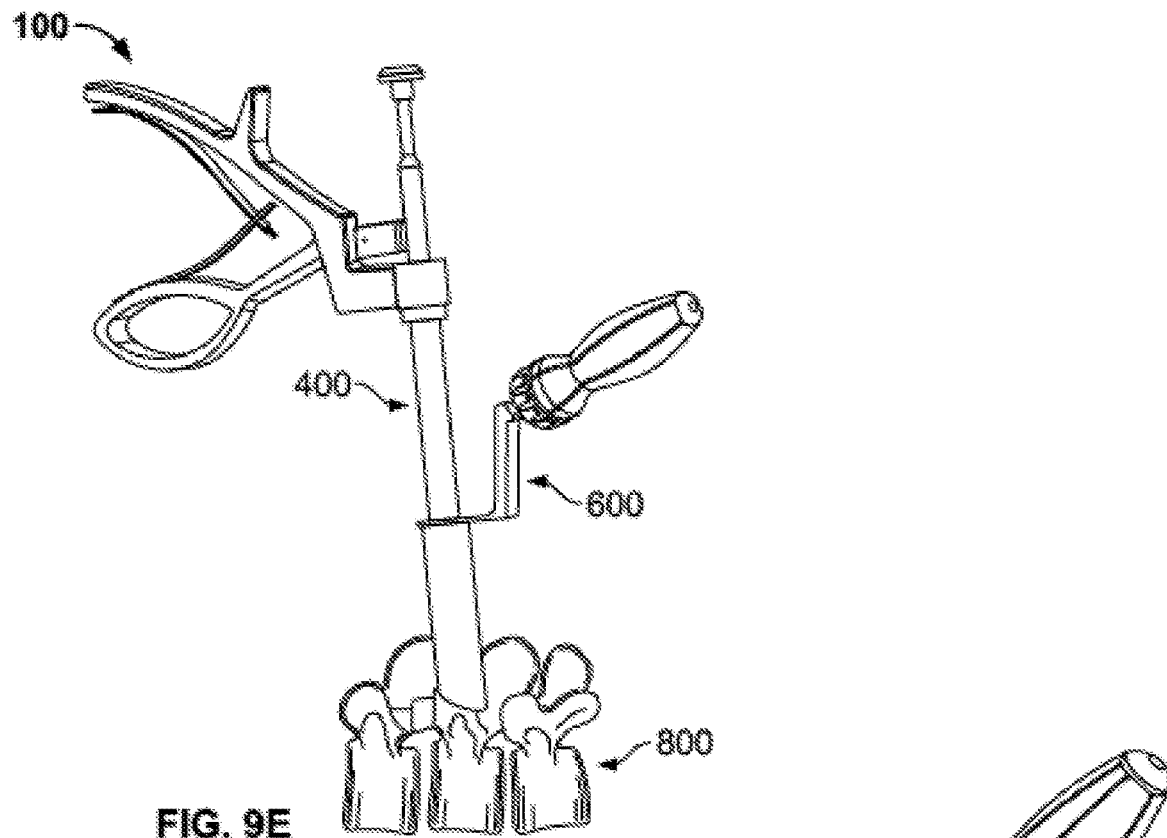
FIGS. 9E-F show the injector assembly inserted through the access portal assembly toward the spine.
Figure 9F:
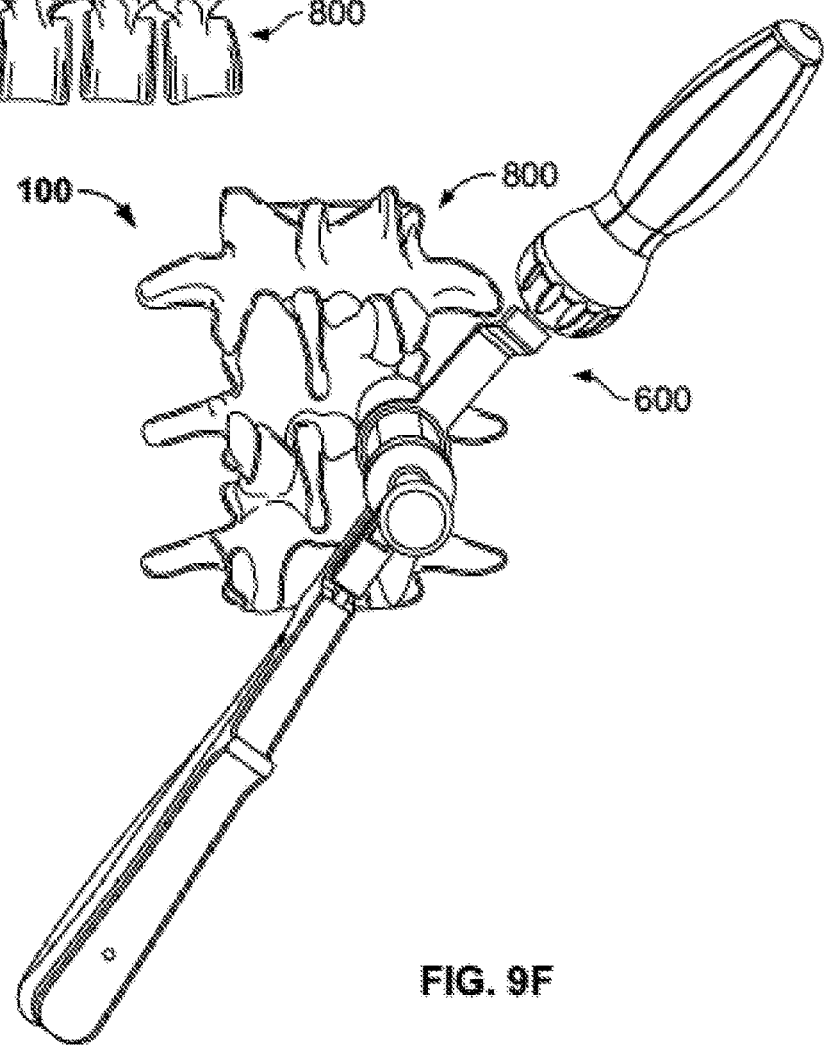
Figure 9G:
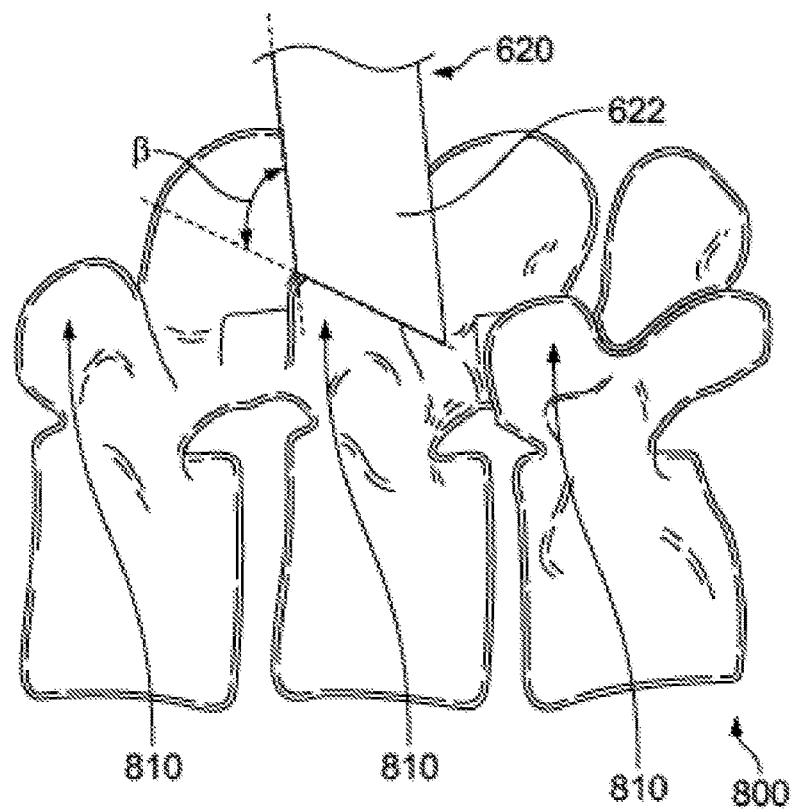
FIGS. 9G-H show the distal end of the access portal assembly contacting the spine.
Figure 9H:
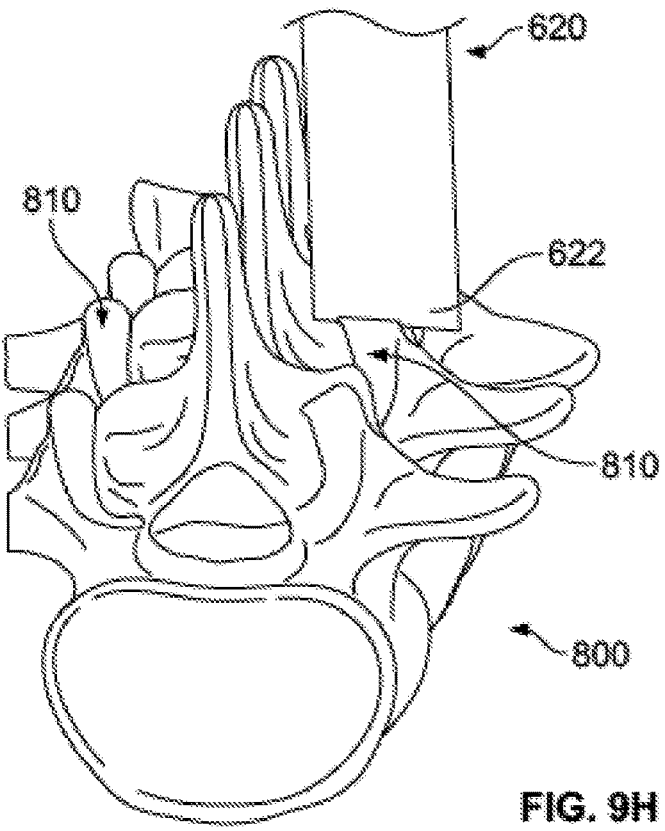

After facet joint 810 is prepared, the cutting tool may be removed from access portal assembly and, if not already prepared, delivery tube subassembly 500 may be filled with a bone graft or other desired material, as described above in relation to FIGS. 6A-F. As described in relation to FIGS. 7A-I, if not already done, injector assembly 100 may also be assembled. Once loaded and assembled, the surgeon inserts injector assembly 100 into access portal assembly 600 until the distal end of delivery tube subassembly 500 meets facet joint 810, as illustrated in FIGS. 9E-F. As described above, the configuration of injector assembly 100 allows the surgeon to entirely operate it using a single hand. As such, the surgeon may operate injector assembly 100 with a first hand while simultaneously operating access portal assembly 600 with a second hand to achieve the desired position of each assembly in relation to one another and also in relation to the patient's anatomy. As described above in relation to FIG. 8D and as illustrated in FIGS. 9G-H, the distal end of access tube 620 may include beveled edge 622 forming an angle 13 of approximately 30 degrees. This angle 13 may facilitate sufficient engagement to facet joint 810, while access tube 620 may be large enough in diameter to provide access to the entire joint.

Figure 9I:
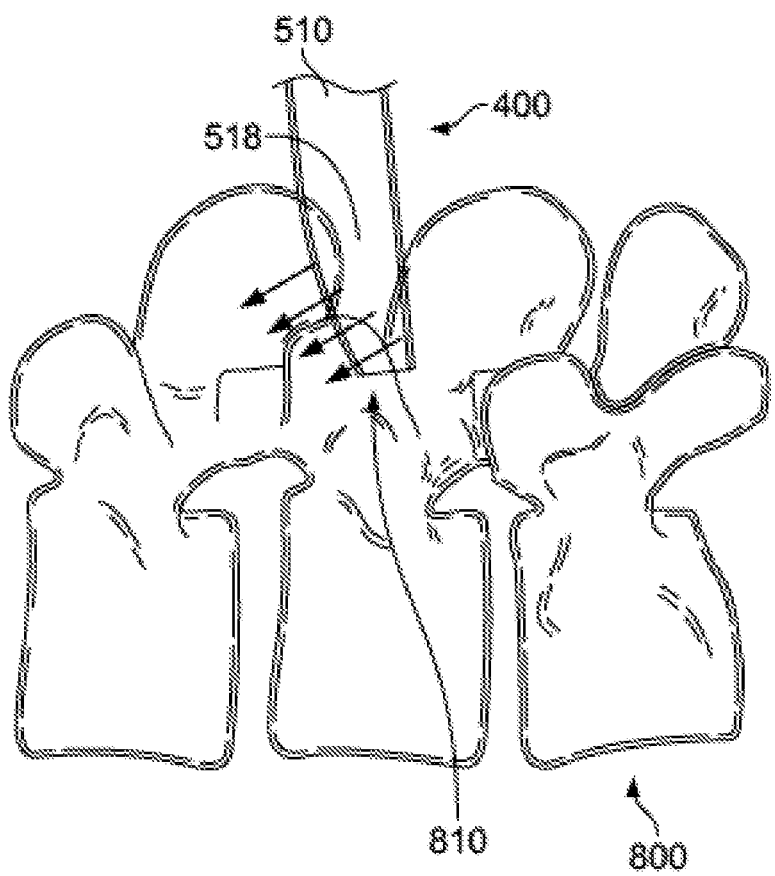
FIGS. 9I-J show the distal end of the delivery tube subassembly contacting the spine.
Figure 9J:
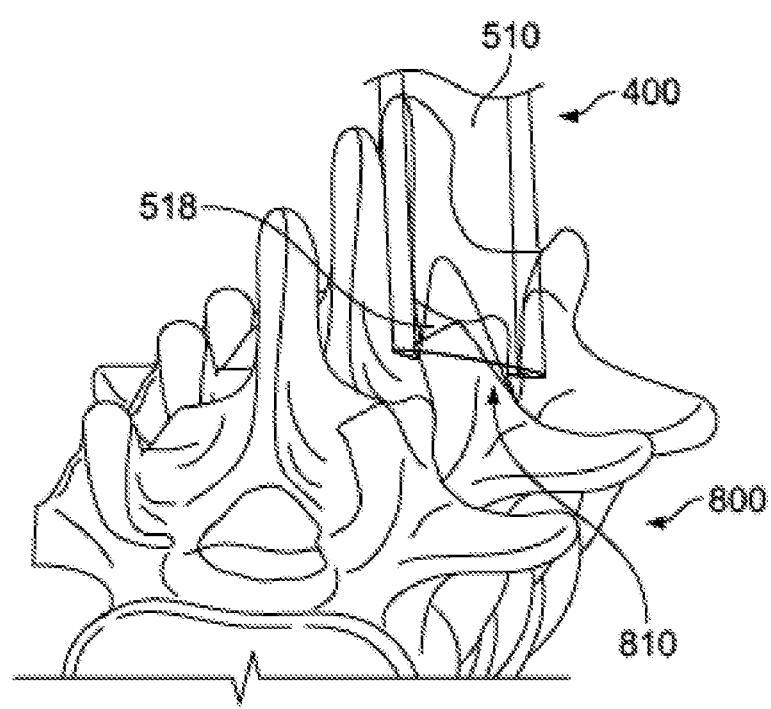
Figure 9K:
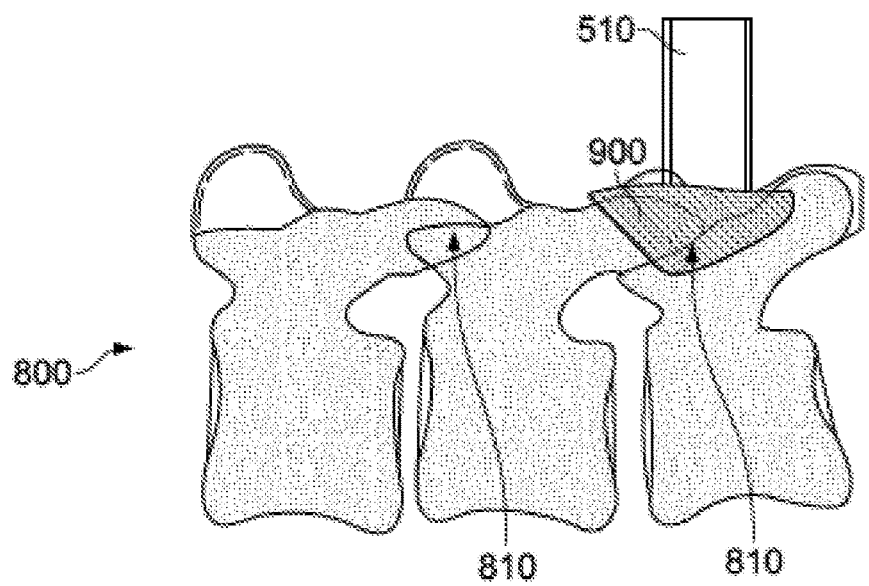
FIG. 9K shows bone graft material being delivered from the delivery tube subassembly to the spine.
Figure 9L:
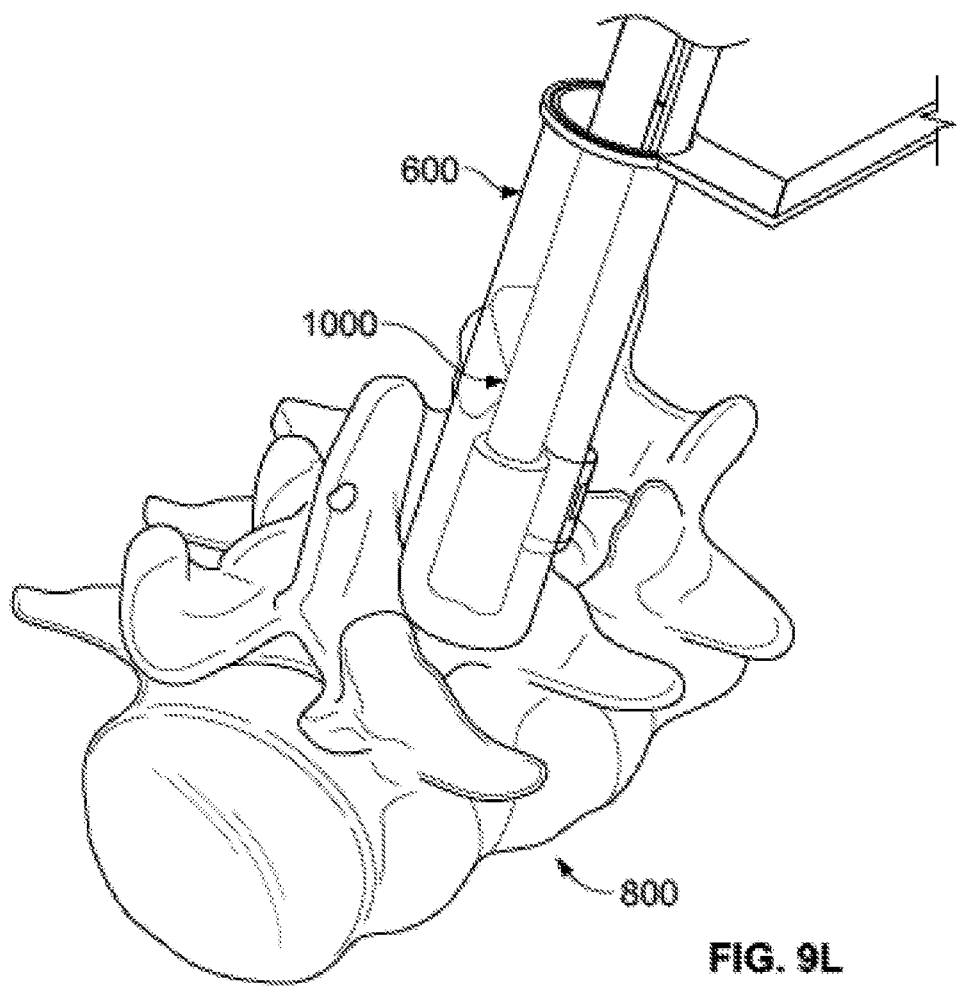
FIG. 9L shows a tamping device inserted through the access portal assembly.

FIGS. 9I-J illustrate delivery tube subassembly 500 in position with access portal assembly 600 invisible for purposes of illustration. As described in relation to FIGS. 6B-C, delivery portion 518 at the distal end of the body 512 of graft tube 510 takes the form of interrupted hollow cylinder. This "cut" or "U"-shaped portion facilitates off-axis expulsion of the bone graft, as indicated by the arrows in FIG. 9I, to position the bone graft on facet joint 810 as desired by the surgeon. The desired amount of bone graft 900 may be expelled from injector assembly 100 in an iterative expulsion as described above, until the desired amount of bone graft is on the particular facet joint 810, as illustrated in FIG. 9K. Injector assembly 100 may then be removed from access portal assembly 600, and, if desired, bone graft 900 may be compacted and/or tamped down using a tamping device 1000 inserted through the access portal assembly, as illustrated in FIG. 9L. Once the surgeon is satisfied of the placement of the bone graft 900, he or she may remove access portal assembly 600 and implant one or more pedicle screws 720 and other related components, as is known in the art.

Although injector assembly 100 has been described as using a ratcheting mechanism to incrementally advance plunger shaft 410 and plunger tip 420 through delivery tube subassembly 500, and thus to incrementally expel bone graft 900 contained therein, other mechanisms may be equally suitable. For example, FIG. 10 illustrates an auger shaft 410' with an auger tip 420' on at least a portion of a distal end thereof. Auger shaft 410' and tip 420' may work with a system substantially similar to injector assembly 100, except actuation of a handle rotates the shaft 410', rather than incrementally advancing a shaft in a longitudinal direction. For example, squeezing a handle of an alternate injector assembly could cause an incremental rotation of shaft 410' and thus an incremental rotation of auger tip 420'. Alternatively, squeezing a handle could cause continuous rotation of shaft 410', depending on the amount of force applied, rather than having incremental rotation. In either case, bone graft may be packed around auger tip 420' such that, upon rotation, bone graft is forced distally out of the alternate injector assembly. The remaining portions of injector assembly 100 and access portal assembly 600 may be substantially identical to those described above.

FIG. 11A illustrates a graft tube 510 with a delivery portion 530 taking a different shape than previously described embodiments. Graft tube 510 may be identical in all respects to the previously described embodiment, except that the delivery portion 530 at the distal end of body 512. In this embodiment, delivery portion 530 takes the form of an interrupted hollow cylinder. More particularly, delivery portion 530 includes a bilateral off-axis exit portion in the general shape of two "U" cuts around the circumference of body 512, each "U" shape being generally a mirror image of the other. As illustrated in FIG. 11B, this configuration may be useful in facilitating bilateral off-axis expulsion. This geometry of delivery portion 530 may provide for more optimal delivery when, for example, delivering bone graft 900 to a facet joint 810 of the spine 800 during via a posterior approach.

Figure 12A:
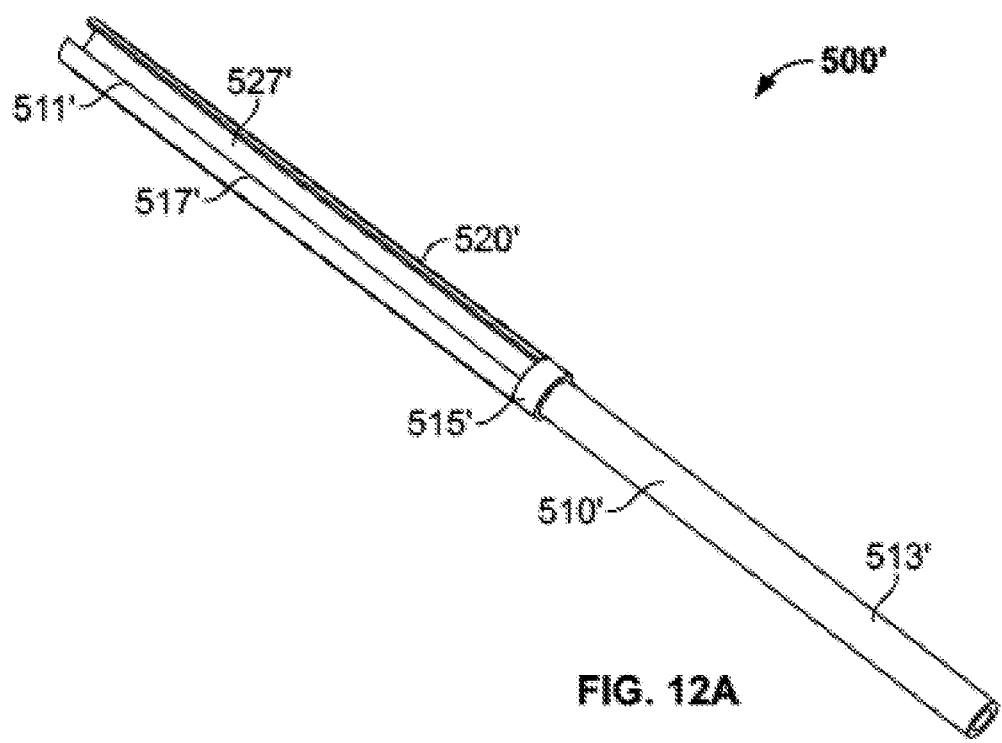
FIG. 12A shows another embodiment of a delivery tube subassembly in an open, loading configuration.

FIG. 12A illustrates an alternate embodiment of delivery tube subassembly 500'. Generally, delivery tube subassembly 500' includes a graft tube 510' and a rotatable sheath 520'. Graft tube 510' is generally in the form of an elongate hollow cylinder with a proximal portion 511' and a distal portion 513'. Graft tube 510' may also include a cylindrical stop 515', although other shapes may be suitable. While distal portion 513' of graft tube 510' generally takes the form of an uninterrupted hollow cylinder, proximal portion 511' may take the form of an interrupted hollow cylinder. More particularly, an elongate slot 517' may extend a partial length or the entire length of proximal portion 511'. Sheath 520' may take the general form of an interrupted hollow cylinder 520' with a slot 527' extending a partial or entire length of the sheath. Sheath 520' and stop 515' may be designed such that the sheath cannot easily slide over the stop.

Figure 12B:
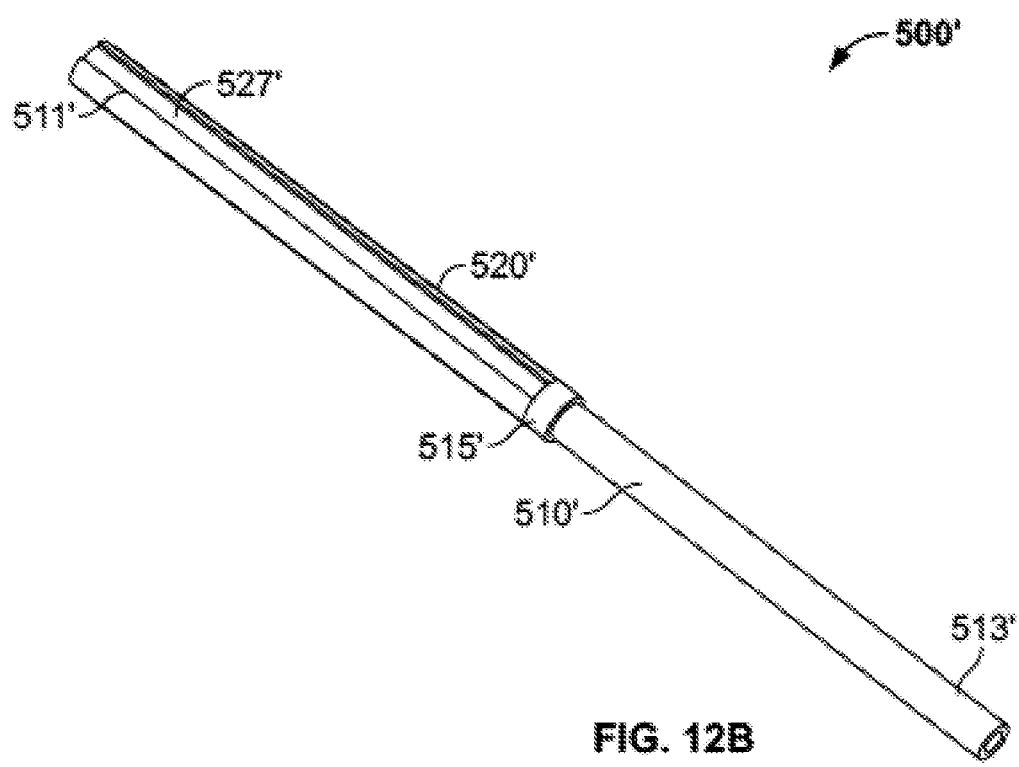
FIG. 12B shows the delivery tube subassembly of FIG. 12A in a closed, loaded configuration.

In order to load delivery tube subassembly 500' with bone graft, sheath 520' may be rotated about proximal portion 511' of graft tube 510' until the slot 527' of the sheath aligns with slot 517' of the graft tube. This open, loading configuration leads to a window in the delivery tube subassembly 500' that a user can load with bone graft, for example by pushing bone graft through the window to the inner diameter of the delivery tube subassembly. Once the desired amount of bone graft is loaded to the inner diameter, sheath 520' may be rotated with respect to graft tube 510' until slot 527' no longer aligns with 517', as illustrated in FIG. 12B. In other words, in this closed position, the inner diameter of graft tube 510' is no longer exposed via sheath slot 527', as graft tube slot 517' is fully covered by the sheath 520'. In this closed, loaded configuration, the bone graft is secure and the delivery tube subassembly 500' may be connected to the remainder of the injector assembly 100 as used as described in other embodiments above.

Figure 13A:
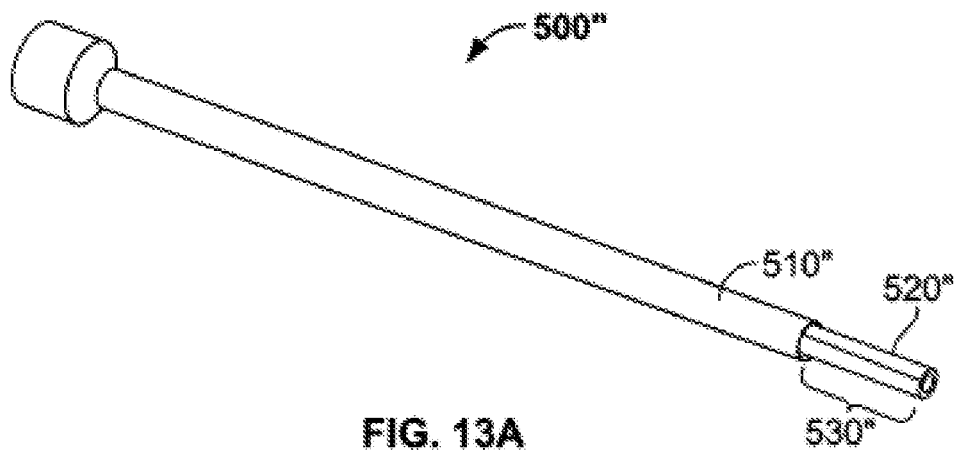
FIG. 13A shows a further embodiment of a delivery tube subassembly in an assembled configuration.
Figure 13B:
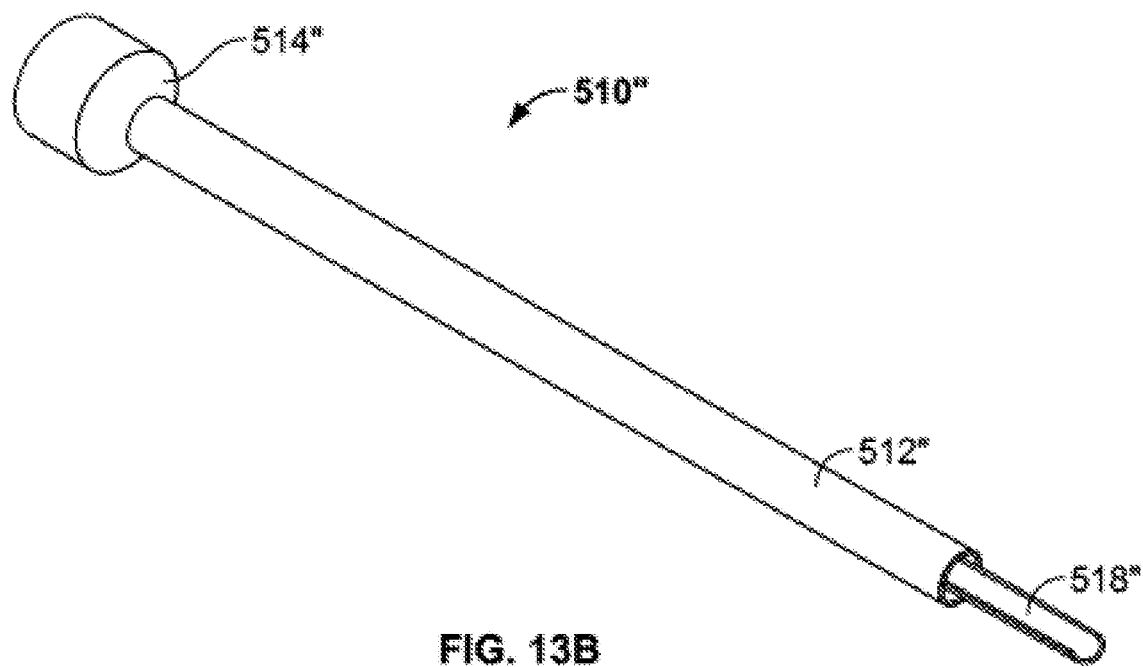
FIG. 13B shows an outer cannula of the delivery tube subassembly of FIG. 13A.
Figure 13C:
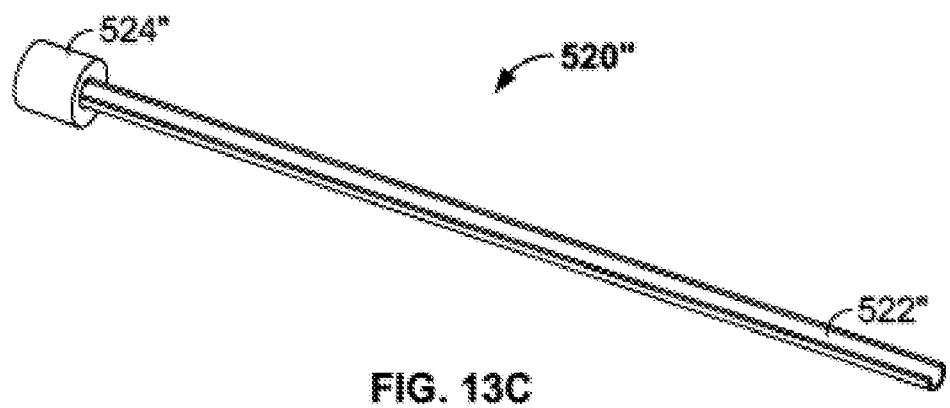
FIG. 13C shows an inner cannula of the delivery tube subassembly of FIG. 13A.
Figure 13D:
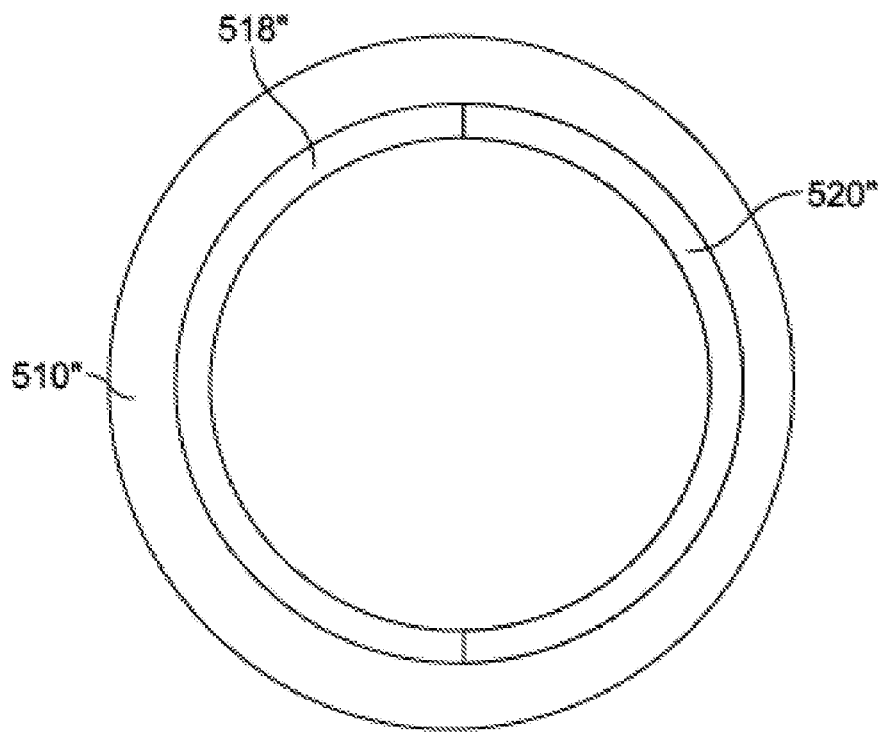
FIG. 13D is a cross-sectional view of the assembled delivery tube subassembly of FIG. 13A.

An additional embodiment of a delivery tube subassembly 500" is illustrated in FIG. 13A. Generally, delivery tube subassembly 500 includes an outer cannula 510" and an inner cannula 520". Outer cannula 510" is illustrated in greater detail in FIG. 13B. Outer cannula 510" may include a generally hollow cylindrical body 512", a cap 514", and a distal portion 518" at a distal end of the body. Cap 514" may be generally cylindrical with a larger diameter than body 512". Distal portion 518" may take the general form of partial cylinder, in this case a half-cylinder. Distal portion 518" may extend distally of a distal end of body 512", but may also extend proximally within part of or the entire length of body 512" up to cap 514". Inner cannula 520" is illustrated in greater detail in FIG. 13C. Inner cannula 520" may include a generally hollow body 522" and a cap 524". Body 522" may take the form, for example, of a trough, a clamshell, or an elongated partially cylindrical body. In the illustrated embodiment, body 522' takes the form of a half-cylinder. Cap 524" may take the general form of an entire hollow cylinder, and may be configured to fit within cap 514" of outer cannula 510". When inner cannula 520" is inserted into outer cannula 510", as illustrated in FIGS. 13A and 13D, the body 522" of the inner cannula aligns with the distal portion 518" of the outer cannula to create a cylindrical delivery portion 530". The cooperation of the distal portion 518" of the outer cannula 510" and the body 522" of the inner cannula 520" also prevents the inner cannula from rotating with respect to the outer cannula once assembled together.

In order to load delivery tube subassembly 500" with bone graft, inner cannula 520" may be filled with bone graft by the user before it is assembled with outer cannula 510". Once the desired amount of bone graft is loaded on the inner cannula 520", it may be inserted into the outer cannula 510" until the cap 524" of the inner cannula is fully inserted into the cap 514" of the outer cannula. In this assembled configuration, the delivery tube subassembly 500" may be connected to the remainder of the injector assembly 100 as used as described in other embodiments above. It should also be noted that, in the assembled configuration, the delivery portion 530" may be of a smaller diameter than the remainder of the body 512" of outer cannula 510", and also extend a distance beyond the distal of the body. In one example, the delivery portion 530" may have a length, for example, of between approximately 20 mm and approximately 40 mm, for example approximately 30 mm. The outer diameter of the delivery portion 530" may be, for example, of between approximately 4 mm and approximately 12 mm, for example approximately 8 mm A delivery portion 530" with a length of approximately 30 mm and an outer diameter of approximately 8 mm may be particularly suitable for delivery of bone graft into disc space.

Further, although bone graft delivery system 10 has been described for use with facet joints 810, other uses are contemplated. For example, a system nearly identical to bone graft delivery system 10 may be used for interverterbral bone graft delivery, although components of the system may be smaller and/or differently configured as appropriate to be capable of desirable positioning within different portions of the spinal anatomy. Similarly, the system described herein may be suitable for use in delivering bone graft to the posterolateral gutters of the spine. Further, the system described herein may be useful for delivering bone graft to vertebral cages used in interbody fusion, particularly expandable cages. Expandable vertebral cages are generally inserted into the spine and expanded to provide desired spacing. Filling the expandable cage with bone graft after the cage is expanded may be significantly simplified by using the systems described herein. For any use of the system, it may be possible to use the system entirely percutaneously through a single point of entry or through multiple points of entry. Even in a non-percutaneous open surgical procedure, the system described herein may be used to deliver bone graft as necessary.

Because the system described herein may be used in multiple procedures, small modifications, such as to the diameter, length, or other sizes of the components described herein, may help optimize the delivery of bone graft to the desired site. In addition, or as an alternate, to resizing components of the system, one or more delivery tips may be provided with the system to fit on the distal end of delivery tube subassembly 500. For example, tips with reduced diameter may be provided with the system. The reduced diameter tip may be fit onto the distal end of delivery tube subassembly 500 prior to interverterbral bone graft delivery. Such tips may also be contoured, curved, or otherwise shaped to optimize bone graft delivery to the particular anatomy of interest in the particular procedure being performed. The tips may be formed of a metal for use in surgery, but preferably are formed from a disposable plastic for use in surgery. In one example, the system described herein may come prepackaged with a set of delivery tips for a number of procedures, allowing the surgeon to choose the particular tip he deems most suitable for a given procedure. Even further, the tips may customizable, such that prior to a procedure, a surgeon may request a tip designed for the specific patient undergoing the procedure.

Figure 14A:
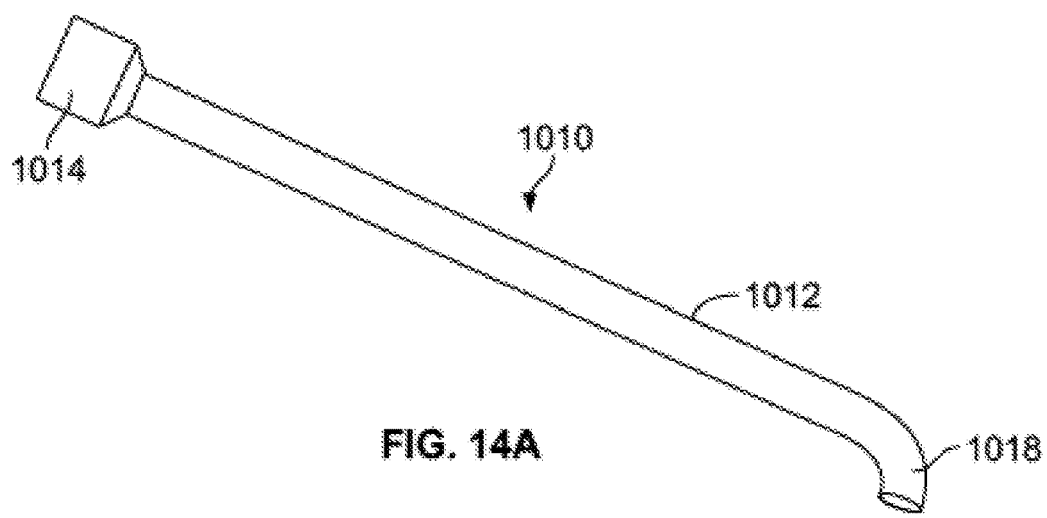
FIG. 14A illustrates an alternate embodiment of a graft tube with a curved delivery tip.
Figure 14B:
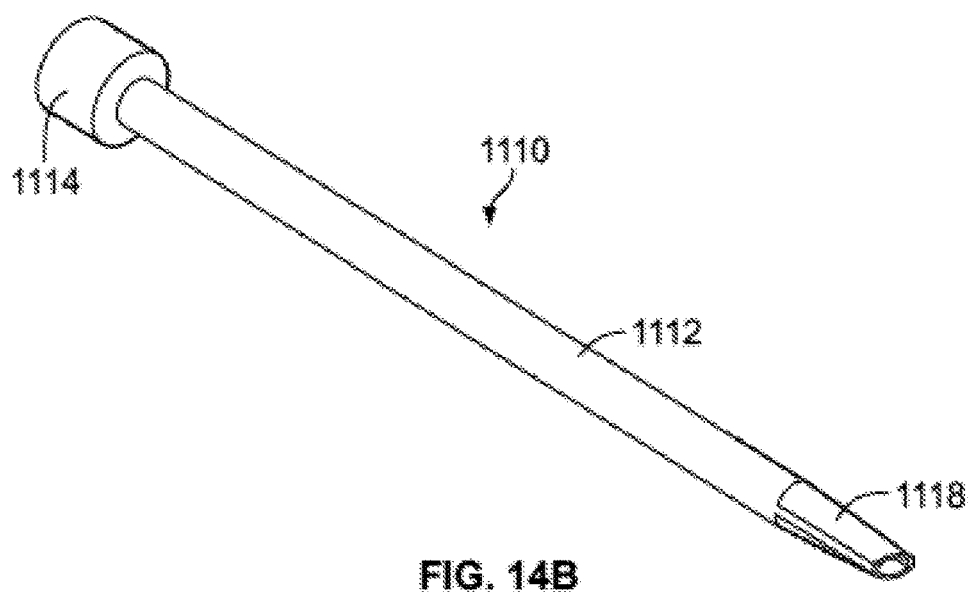
FIGS. 14B-C illustrate a further embodiment of a graft tube with a duckbill shaped delivery tip.
Figure 14C:
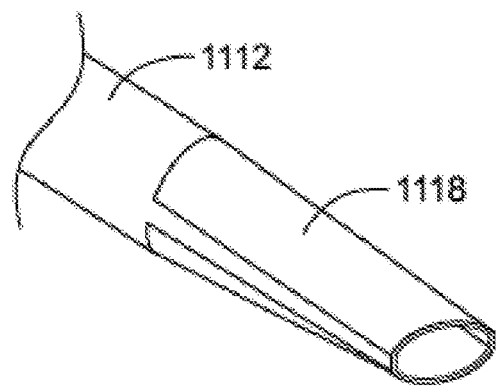

Delivery tips may alternately be formed as part of a larger graft tube, rather than being snap-on additions. For example, FIG. 14A illustrates a graft tube 1010 similar to graft tube 510 in many respects, but with a different delivery tip. In particular, graft tube 1010 includes a generally hollow cylindrical body 1012, a cap 1014, and a curved delivery portion 1018 at a distal end of the body. The curved delivery portion 1018 may provide the ability to deliver bone graft at angles and locations that would be difficult with other embodiments described herein. Another graft tube 1110 with an alternate delivery tip is illustrated in FIGS. 14B-C. Again, graft tube 1110 similar to graft tube 510 in many respects, but with a different delivery tip. In particular, graft tube 1110 includes a generally hollow cylindrical body 1112, a cap 1114, and a duckbill shaped delivery portion 1118 at a distal end of the body. The duckbill shaped delivery portion 1118 is illustrated in greater detail in FIG. 14C. The duckbill shaped delivery portion 1118 may provide the ability to deliver bone graft in smaller spaces that would be otherwise difficult with other embodiments described herein.

Figure 15:
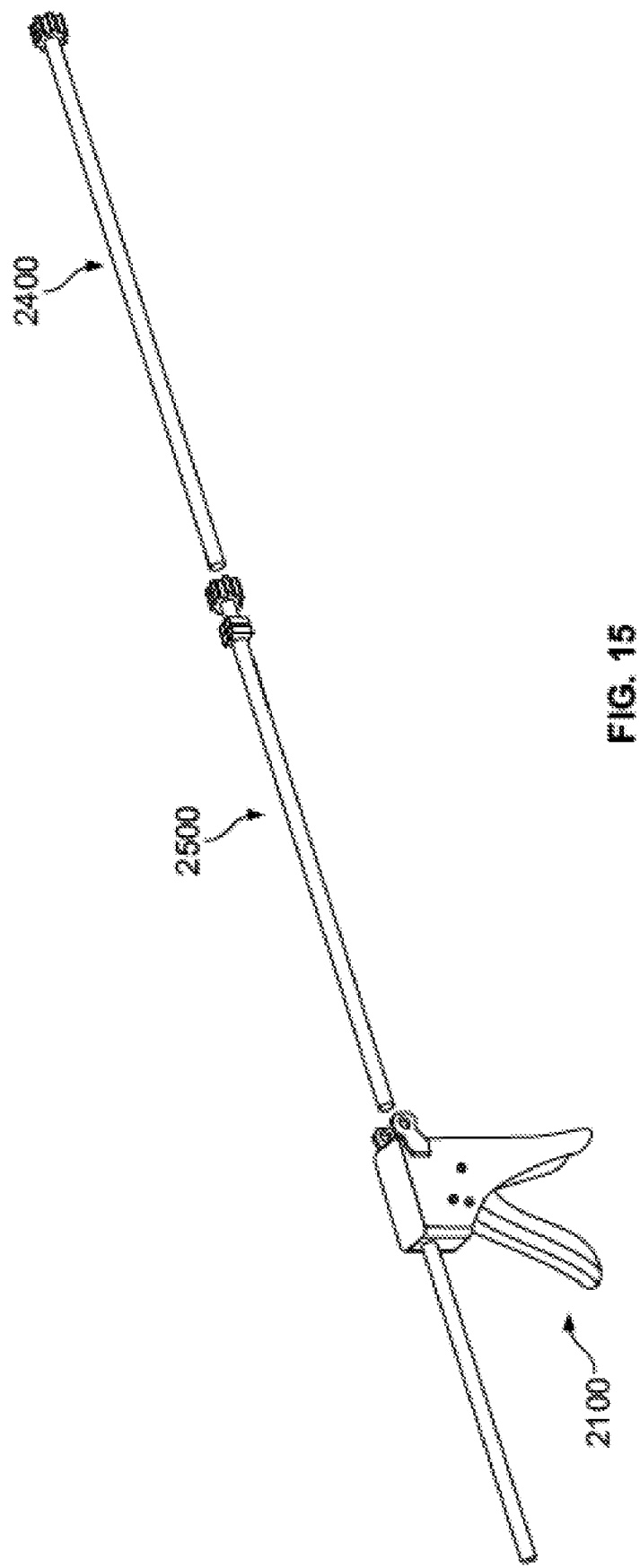
FIG. 15 is an exploded view of a bone graft injection assembly according to yet another embodiment of the disclosure.

Another injector assembly 2100 according to another embodiment of the disclosure is illustrated in FIG. 15. Injector assembly 2100 may include a number of subassemblies including, for example, a handle subassembly 2200, a ratchet subassembly 2300 (not labeled in FIG. 15), a plunger subassembly 2400, and a delivery tube subassembly 2500. It should be understood that the general mechanical principles described above with respect to injector assembly 100 may apply to injector assembly 2100. Injector assembly 2100 may include a cannula 2110 extending distally from the body 2210 of handle subassembly 2200 (described in greater detail below) to facilitate the passage of plunger subassembly 2400 and delivery tube subassembly 2500 through injector assembly 2100.

Figure 16A:
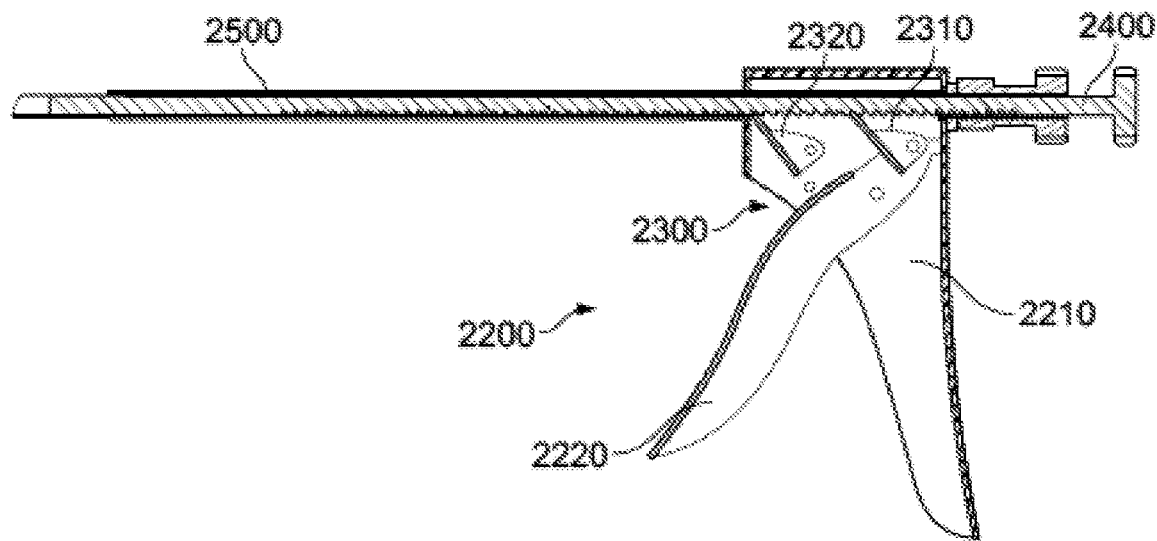
FIGS. 16A-B are cross-section views of the injection assembly of FIG. 15 in a relaxed and actuated state, respectively.
Figure 16B:
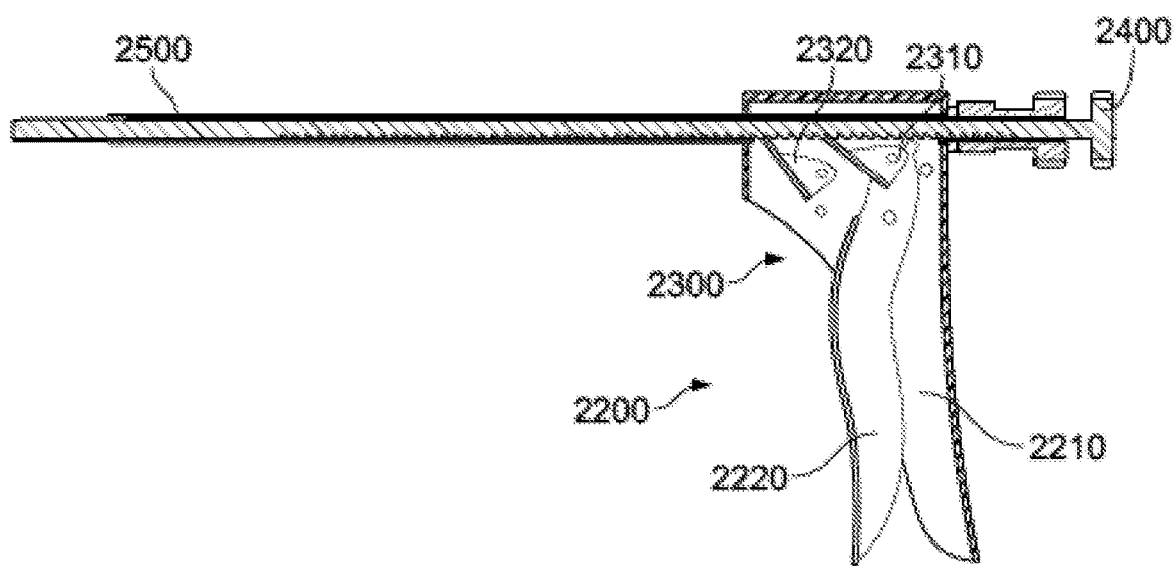

Handle subassembly 2200 may be used to advance plunger subassembly 2400 in an incremental or continuous fashion through delivery tube subassembly 2500 to force a material out of a distal end thereof. For example, as shown in FIGS. 16A-B, handle subassembly 2200 may include body 2210 that houses ratchet subassembly 2300 and portions of other components of the system. Body 2210 may be shaped to include a first or static handle portion. Handle subassembly 2200 may also include a second or moving handle 2200. A user may grip the static handle portion of body 2210 and squeeze moving handle 2220 to actuate the ratchet subassembly 2300 to advance plunger subassembly 2400.

As shown in FIGS. 16A-B, the ratchet subassembly 2300 may include a first pawl 2310 rotatably coupled to moving handle 2220 and a second pawl 2320 rotatably coupled to body 2210. As a user squeezes moving handle 2220 (FIG. 16B), first pawl 2310 is forced forward due to the movement of moving handle 2220. With plunger 2400 loaded into delivery tube subassembly 2500, the first pawl 2310 engages teeth or other corresponding structure of plunger subassembly 2400 and forces plunger subassembly 2400 forward. Moving handle 2220 may be biased, for example via a spring (not illustrated( ) connecting moving handle 2220 to body 2210, so that, in the absence of applied force, moving handle 2220 is biased away from body 2210 to a relaxed position shown in FIG. 16A. As a user releases his grip and moving handle 2220 moves toward the relaxed position, second pawl 2320 engages a tooth of plunger subassembly 2400 to restrict the plunger subassembly 2400 from moving backward as moving handle 2220 returns to the relaxed position. If, at any point, a user wishes to remove plunger subassembly 2400 from injector assembly 2100, he may grip the proximal end of plunger subassembly 2400 and rotate it so that the teeth no longer engage the first and second pawls 2310 and 2320 and pull the plunger subassembly 2400 out of the injector assembly 100. Otherwise, alternative or additional disengagement mechanisms may be provided for second pawl 2320 (and first pawl 2310 if desired) to allow easy removal of plunger subassembly 2400. The plunger subassembly 2400 may generally be similar to plunger subassembly 400 described above in connection with injector assembly 100. Similarly, delivery tube subassembly 2500, either alone or in combination with cannula 2110, may be structurally and/or functionally similar to embodiments of delivery tube subassemblies described above. Further, injector assembly 2100 may be used in combination with access portal subassembly 600 or similar systems.

Figure 17A:
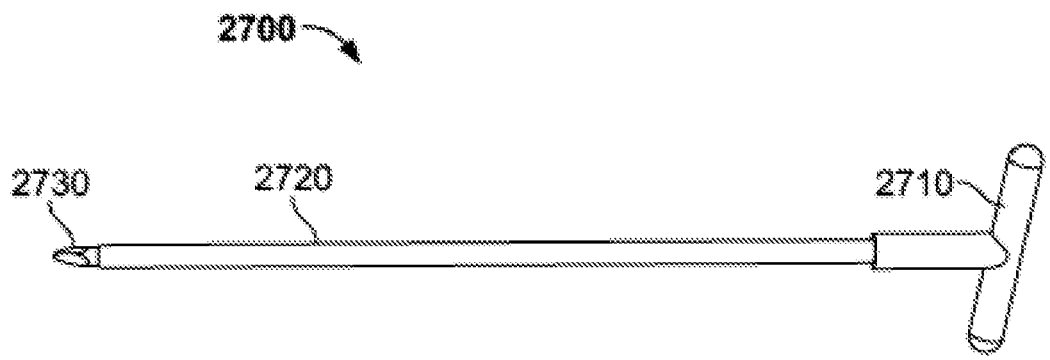
FIG. 17A is a perspective view of a trocar.
Figure 17B:
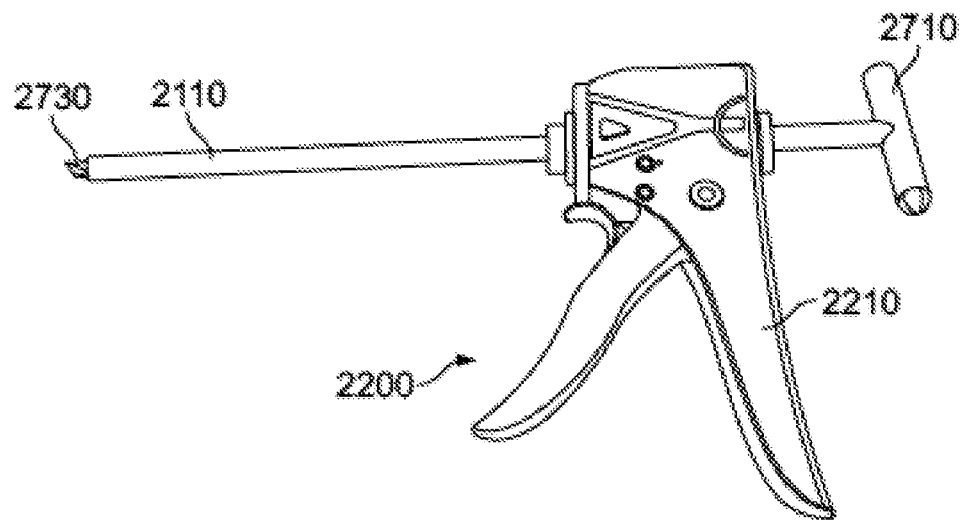
FIG. 17B is a perspective view of the trocar of FIG. 17A assembled with the injection assembly of FIG. 15.
Figure 17C:
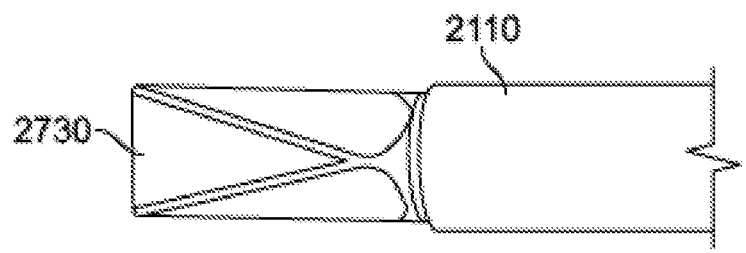
FIG. 17C is an enlarged view of the tip of the trocar assembled to the injection assembly.

Additional systems may be used with injector assembly 2100. For example, FIG. 17A illustrates a trocar 2700 that may be used with injector assembly 2100. Generally, trocar 2700 may include a handle 2710, a rigid shaft 2720, and a tip 2730 at a distal end of the shaft 2720. The use of trocar 2700 with injector assembly 2100 may be particularly useful prior to insertion of bone graft and insertion of an intervertebral spacer or cage. For example, prior to delivering bone graft, a user may insert trocar 2700 through body 2210 of handle subassembly 2200 and the cannula 2110 of injector assembly 2100. The user may grip the handle 2710 and insert until a lip of handle 2710 contacts body 2210 and the trocar 2700 is fully inserted, as shown in FIG. 17B. At this position, tip 2730 preferably projects beyond the distal end of cannula 2110, as shown in FIG. 17C. Injector assembly 2100 with trocar 2700 may be inserted into the body, for example through a portal subassembly 600, and advanced toward the intervertebral space. In this assembled condition, tip 2730 is the distalmost object on injector assembly 2100, and may provide initial contact with anatomy to provide a number of functions. For example, tip 2730 may have a ramped configuration, wherein the distalmost portion of tip 2730 has a relatively small height and a proximalmost portion of tip 2730 has a relatively large height. If the goal is to position a distal end of cannula 2110 in the intervertebral space, this ramped configuration may help guide the distal end of injector assembly 2100 toward that space, the tip 2730 of trocar 2700 acting to distract adjacent vertebral discs apart from one another. Additionally, distal tip 2730 may include one or more relatively sharp surfaces to facilitate preparation of bone or other tissue. For example, the user may desire to shave a portion of a vertebral disc or other anatomy prior to delivering the bone graft and/or implant, for example to change the surface characteristics of the anatomy or to clear a path for bone graft and/or the implant. The cutting surface(s) provided on tip 2730 may facilitate the surgeon in completing that task.

Once the injector assembly 2100 is in place with distal tip 2730 of trocar 2700 and a distal end of cannula 2110 positioned in the intervertebral space, and the bone or other anatomy has been prepared as desired, the user may grip the handle 2710 and remove trocar 2700 from injector assembly 2100, leaving the distal end of cannula 2110 positioned in the intervertebral space, effectively acting as a space holder or wedge keeping the adjacent vertebral discs separated. The user may then insert the plunger subassembly 2400 and delivery tube subassembly 2500 (or another suitable delivery tube subassembly described above) through the cannula 2110 to the intervertebral space, the delivery tube subassembly 2500 having already been packed with bone graft. Bone graft may be delivered by actuating handle subassembly 2200 the desired amount, at which point the plunger subassembly 2400 and delivery tube subassembly 2500 may be removed from the patient and injector assembly 2100. If desired, the intervertebral spacer or cage may be delivered through the cannula 2110, or otherwise the injector assembly 2100 may first be removed and the intervertebral spacer or cage inserted into the intervertebral space in a standard manner.

It should be understood that trocar 2700 may be used with different sizes and/or shapes to accommodate the structure and/or size of injector assembly 2100, the patient anatomy, and/or the particular procedure being performed. For example, trocar 2700 may be used for facet preparation prior to fusion. As there may not be a clear path through the tissue in this minimally invasive procedure, the cutting surface of the tip 2730 may cut through tissue such as muscle that is in the delivery path of injector assembly 2100. It may also be desirable to have one or a group of sharp or cutting surfaces on one portion of tip 2730 (such as the top illustrated in FIG. 17C) with a rounded or otherwise blunted surface on another portion of tip 2730 (such as the bottom). This may provide for enhanced control for the surgeon to cut or modify particular desired anatomical surfaces while maintaining other surfaces relatively undisturbed.

Figure 18A:
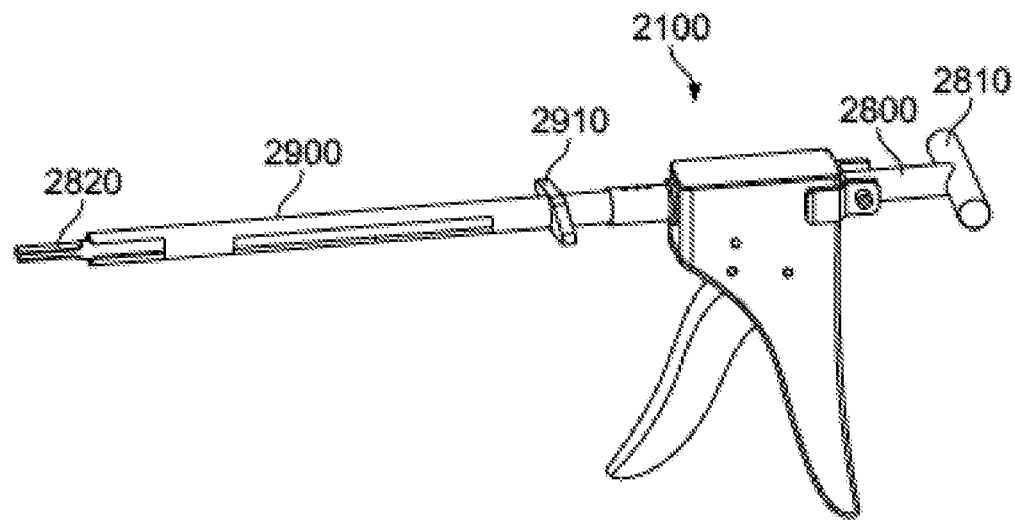
FIGS. 18A-B are perspective views of the injection assembly of FIG. 15 assembled to a distractor and a space holder in two different positions.
Figure 18B:
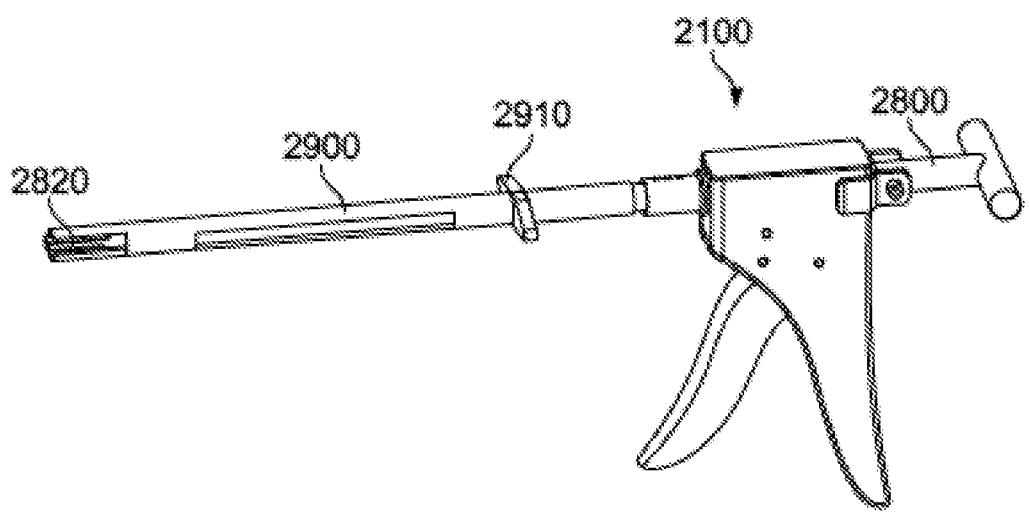

Still additional systems may be used with injector assembly 2100. For example, injector assembly 2100 is illustrated in FIGS. 18A-B with a distractor 2800 positioned within the cannula 2110 and a space holder 2900 positioned over the cannula 2110. Distractor 2800 and space holder 2900 may be particularly useful when working within the intervertebral space.

Distractor 2800 may include a handle 2810 and a rigid shaft extending distally from handle 2810 to a paddle-shaped tip 2820. The shaft may be generally cylindrical to fit within cannula 2110, and the tip 2820 may be flattened such that it has a height that is smaller than its width. In other words, the tip 2820 may have two opposing substantially flattened surfaces. The space holder 2900 may be generally cylindrical such that it fits over cannula 2110 of injector assembly 2100. The space holder 2900 may also include a handle 2910 or other grip so that it may be slid along, or rotated about, the axis of the cannula 2110. Preferably, the distal end of the space holder forms less than a full cylinder so that, in at least one rotational position (e.g. the distraction position), the distal end of space holder 2900 is the same or a similar width as the widest portion of the tip 2820 of distractor 2800. For example, diametrically opposed ends of the distal portion of space holder 2900 may be open, so that the distal tip of space holder 2900 includes two prongs extending from diametrically opposed portions of the space holder.

Figure 18C:
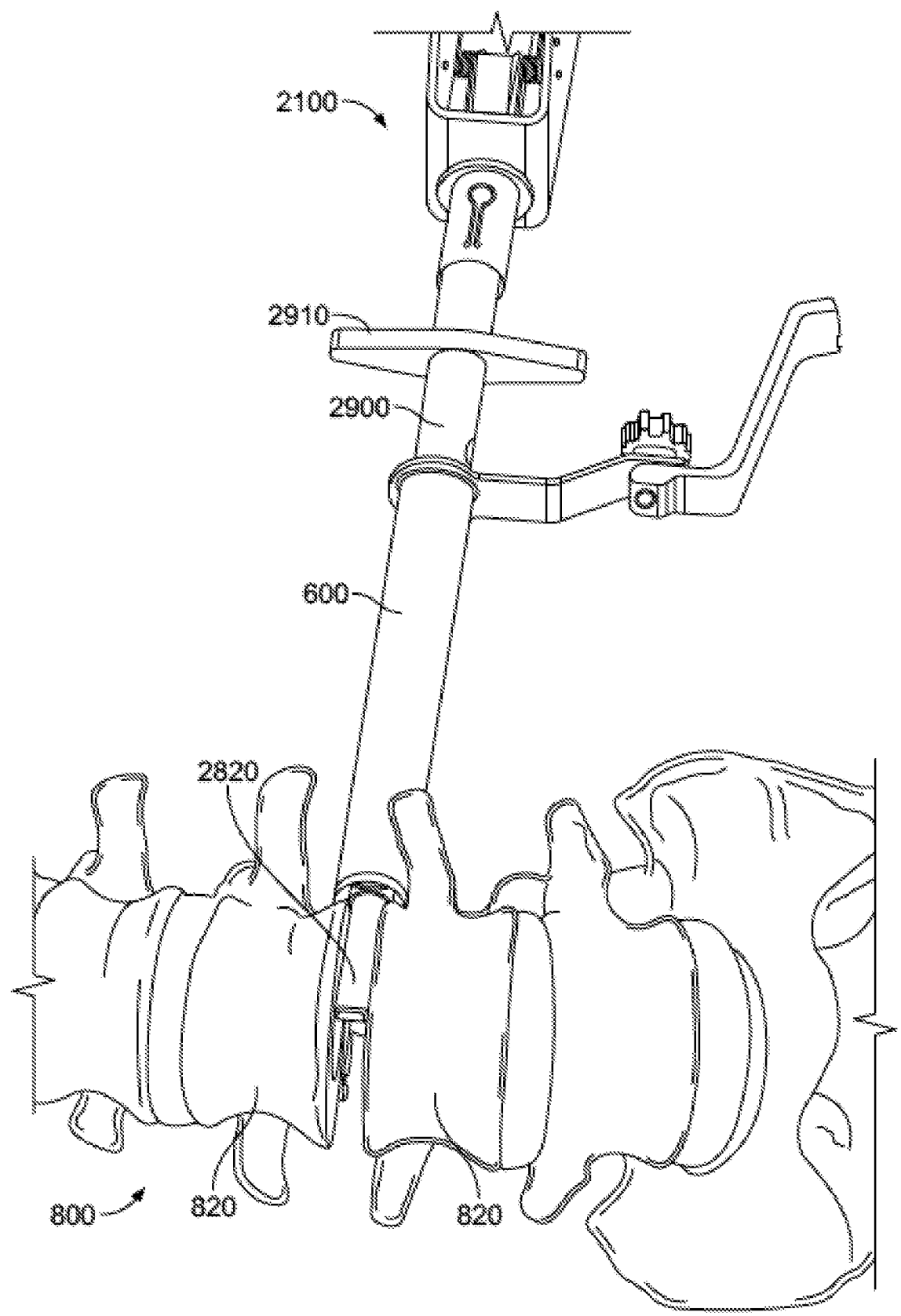
FIG. 18C is a schematic view of the injection assembly in use and the distractor of FIGS. 18A-B inserted into an intervertebral space.
Figure 18D:
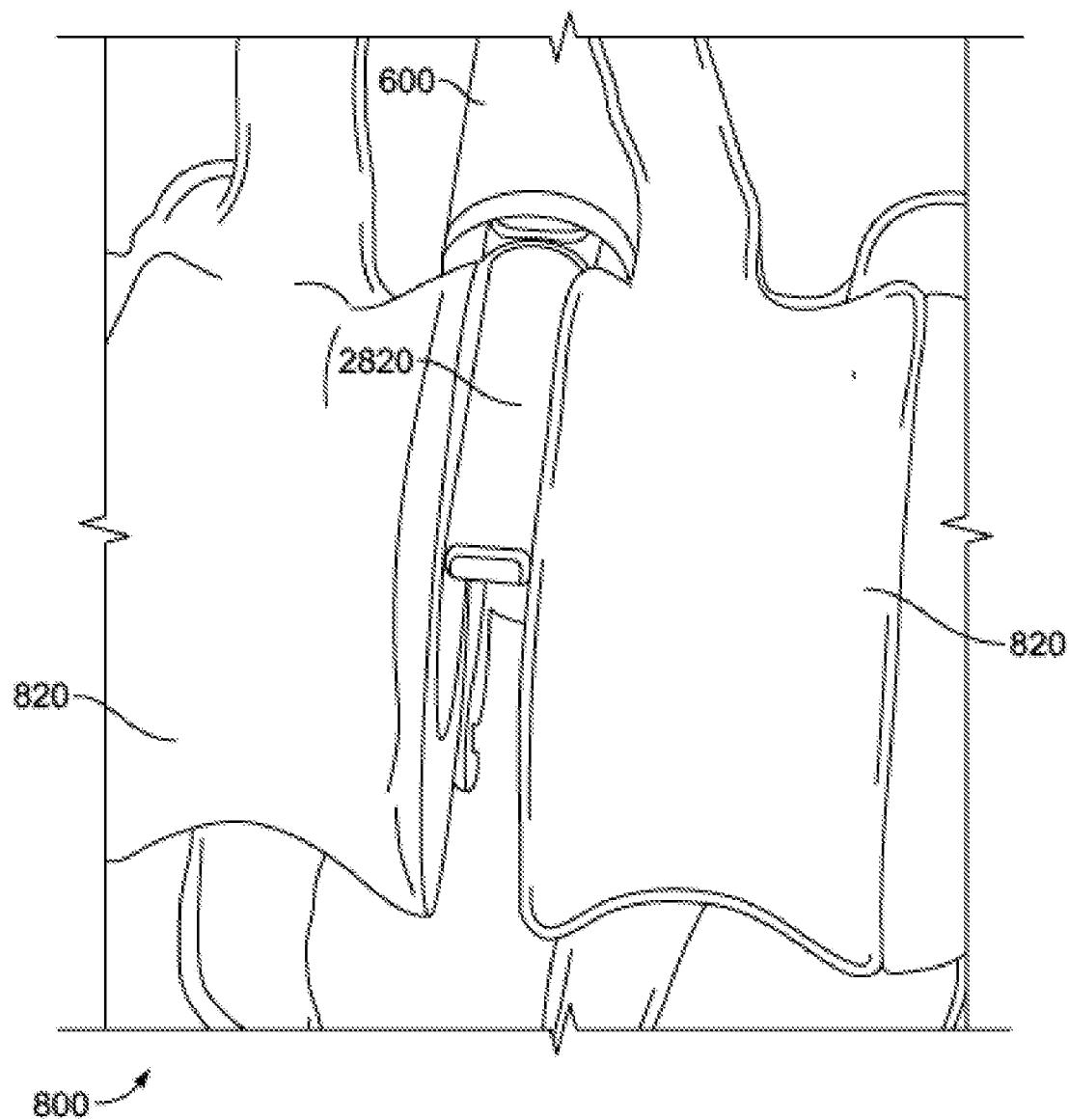
FIG. 18D is an enlarged schematic view of the distractor positioned within the intervertebral space.
Figure 18E:
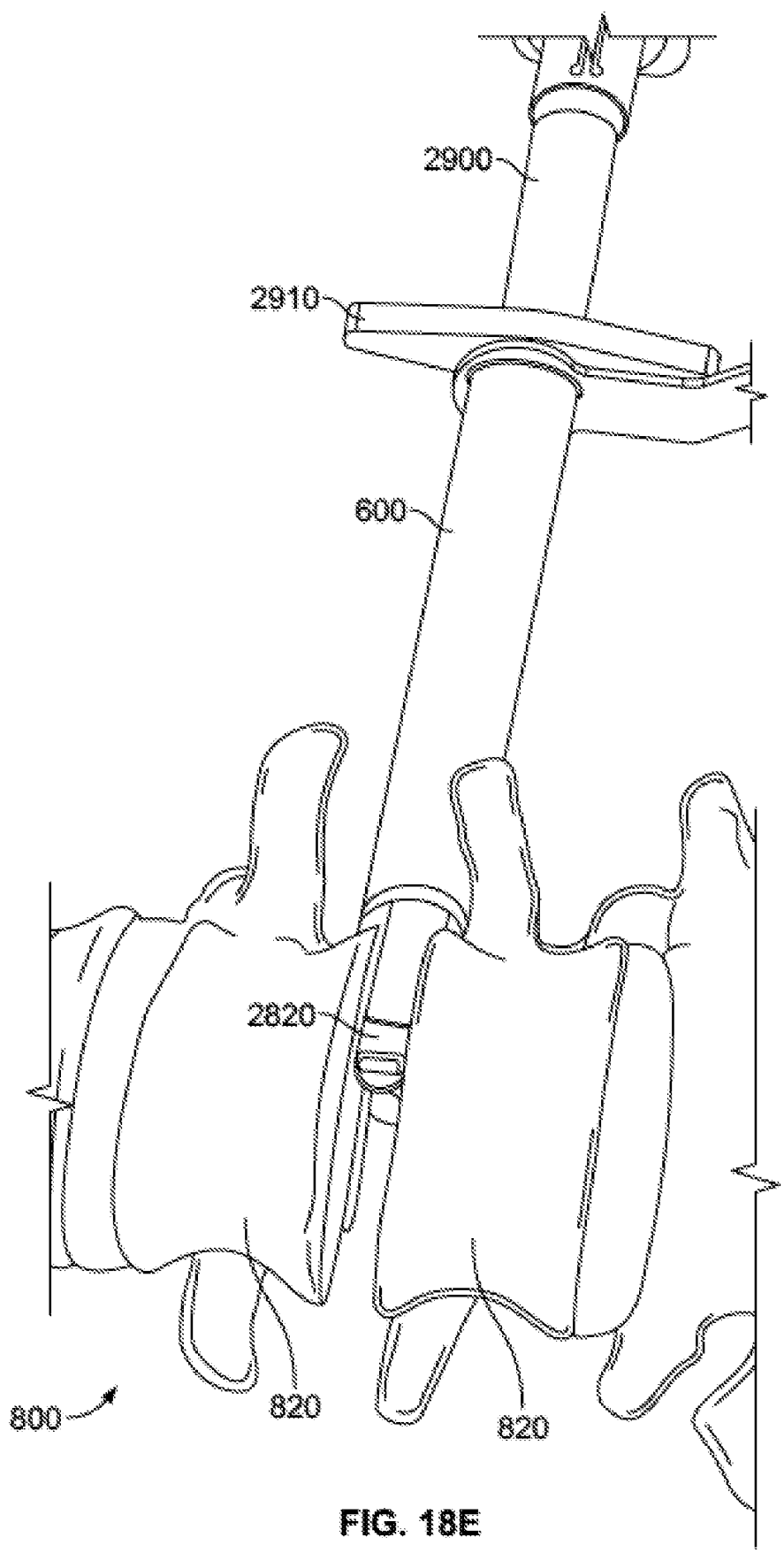
FIG. 18E is a schematic view of the injection assembly in use and the space holder of FIGS. 18A-B inserted into the intervertebral space.
Figure 18F:
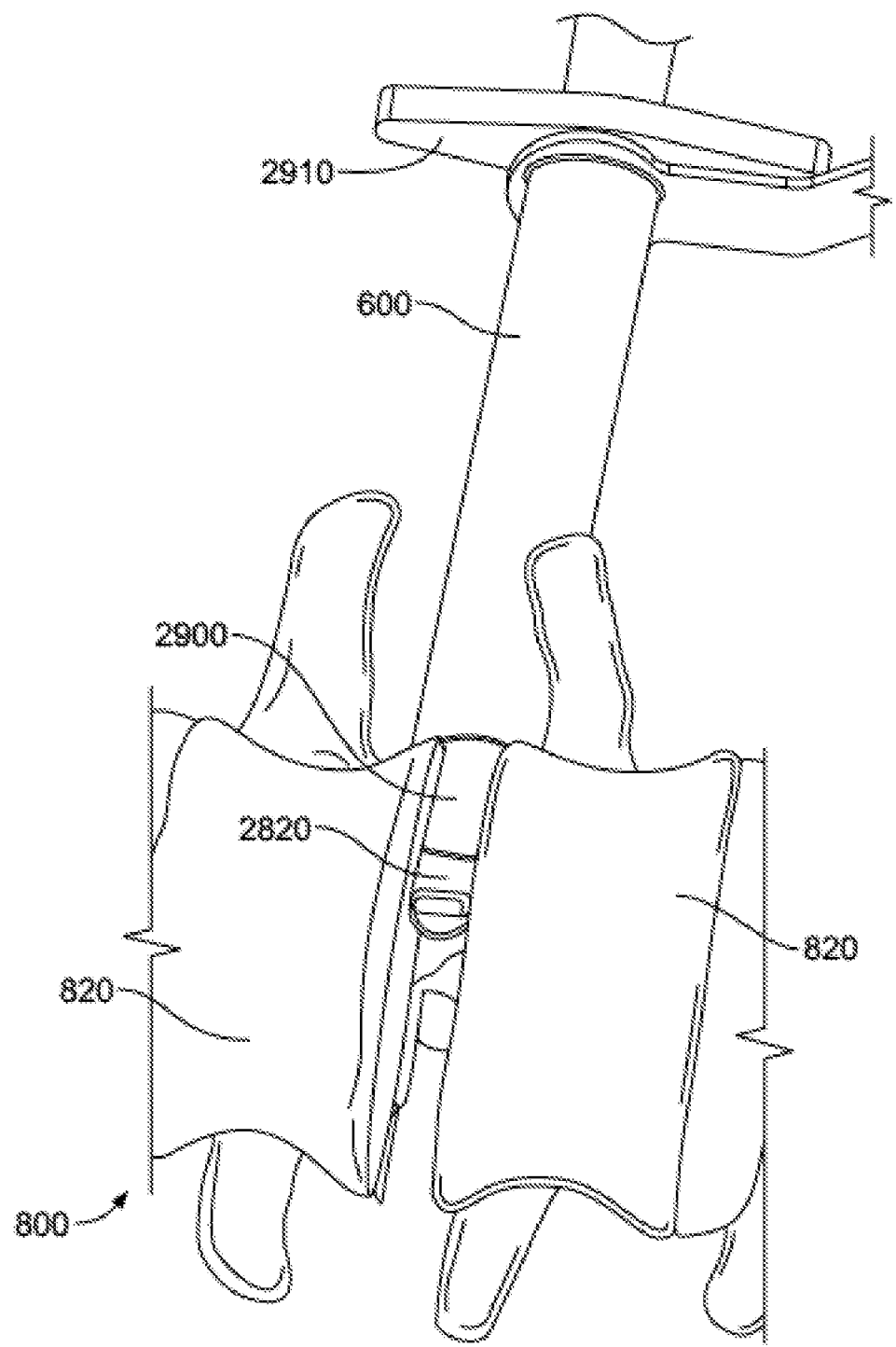
FIG. 18F is an enlarged schematic view of the space holder positioned within the intervertebral space.

As noted above, distractor 2800 and space holder 2900 may be useful when working within the intervertebral space. For example, prior to inserting bone graft or an implant into the intervertebral space, injector assembly 2100, with distractor 2800 within the cannula 2110 and space holder 2900 over the cannula 2110, may be inserted through access portal 600 and advanced to a position near the space between two adjacent vertebrae 820 of the spine 800. Preferably, the disc between the adjacent vertebrae 820 has already been removed, allowing the distractor tip 2820 to enter the intervertebral space. The distractor tip 2820 may be advanced into the intervertebral space in an orientation such that the flattened paddle shape are substantially parallel with the adjacent surfaces of the vertebrae 820. Then, the user may grip the distractor handle 2810 and rotate it approximately 90 degrees. The flattened shape of the tip 2810 will cause the adjacent vertebrae 820 to distract apart from one another once rotated, as shown in FIGS. 18C-D. The width of the distractor tip 2820 may be approximately 8 mm to allow for distraction of approximately 8 mm when rotated, although other sizes, for example between about 4 mm and about 12 mm, may be appropriate depending on the desired use, the sizes of the corresponding components, and the particular anatomy at issue.

Once the adjacent vertebrae 820 have been distracted, the user may grip the space holder 2900 via handle 2910, and slide the space holder 2900 distally so that the distal end of the space holder 2900 slides over the tip 2820 of the distractor 2800, the distal end of the space holder 2900 contacting the adjacent vertebrae 820. The space holder 2900 acts to hold the adjacent vertebrae 820 in the distracted position so that the distractor 2800 may be removed without a change in the relative position of the adjacent vertebrae 820. Preferably, when sliding the space holder 2900 distally, it is in a rotational position such that the height of the distal end of the space holder 2900 is substantially the same as the height of the tip 2820 of the distractor 2800. In this position, the space holder will not catch on the adjacent vertebrae 820 while entering the intervertebral space.

Figure 18G:
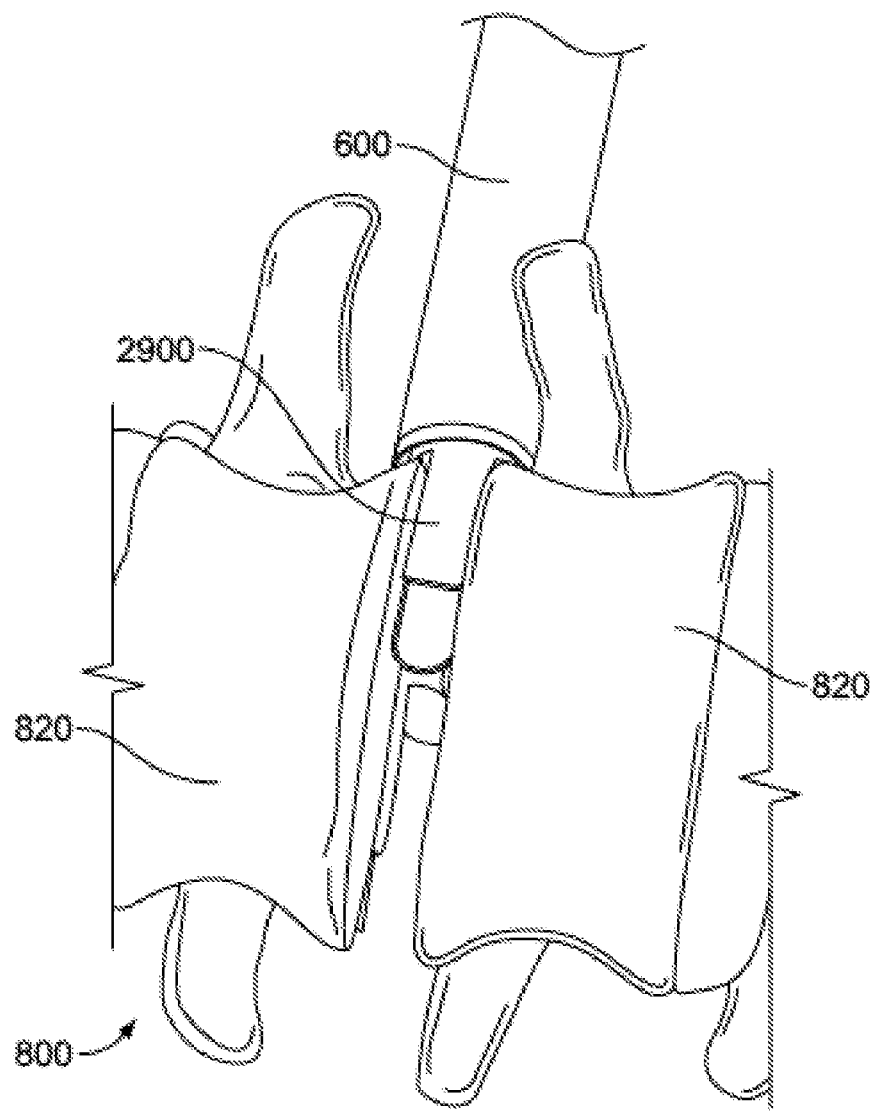
FIG. 18G is an enlarged schematic view of the space holder positioned within the intervertebral space and the distractor removed.
Figure 18H:
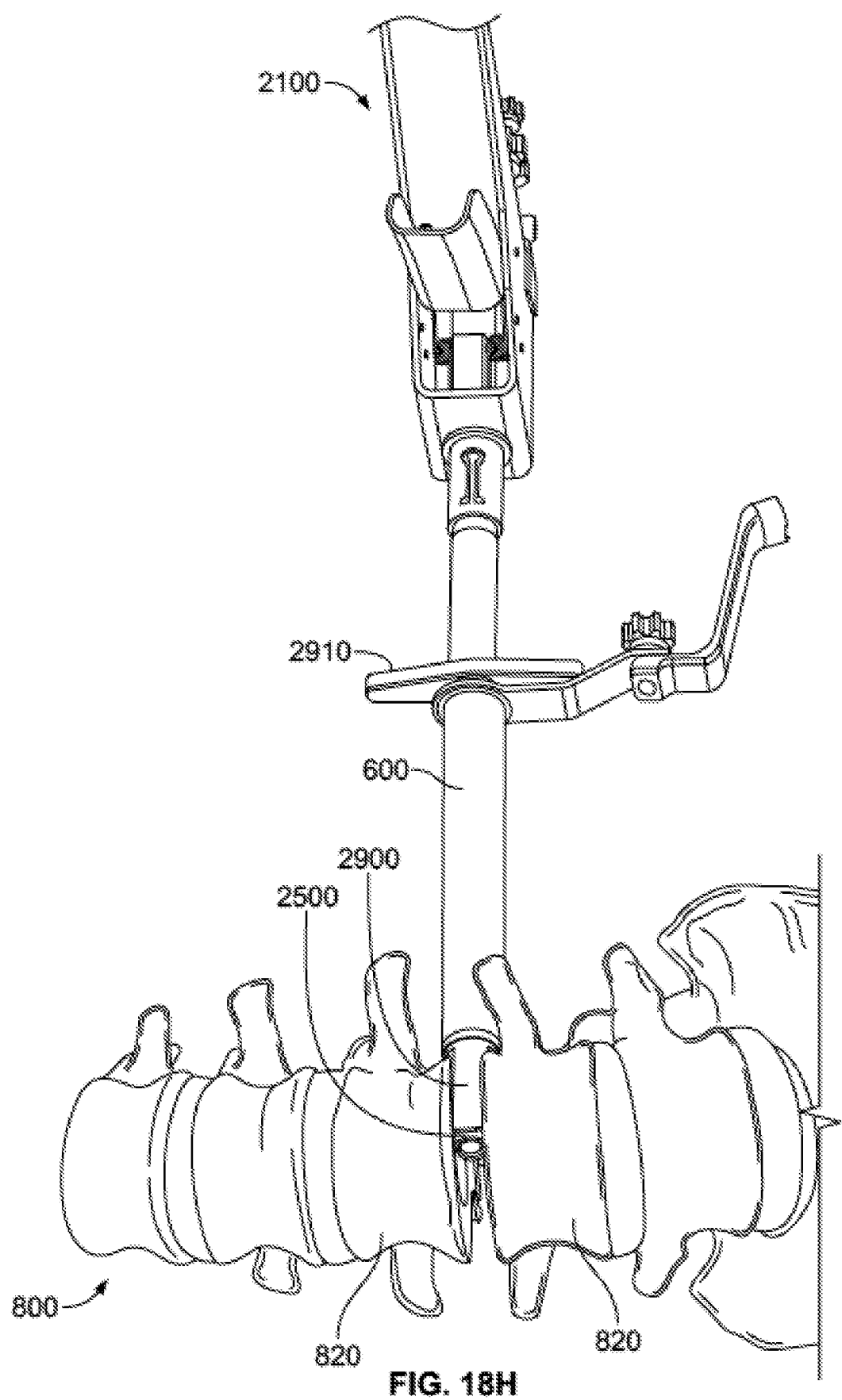
FIG. 18H is a schematic view of the injection assembly in use with a delivery tube subassembly and plunger subassembly positioned within the injection assembly.
Figure 18I:
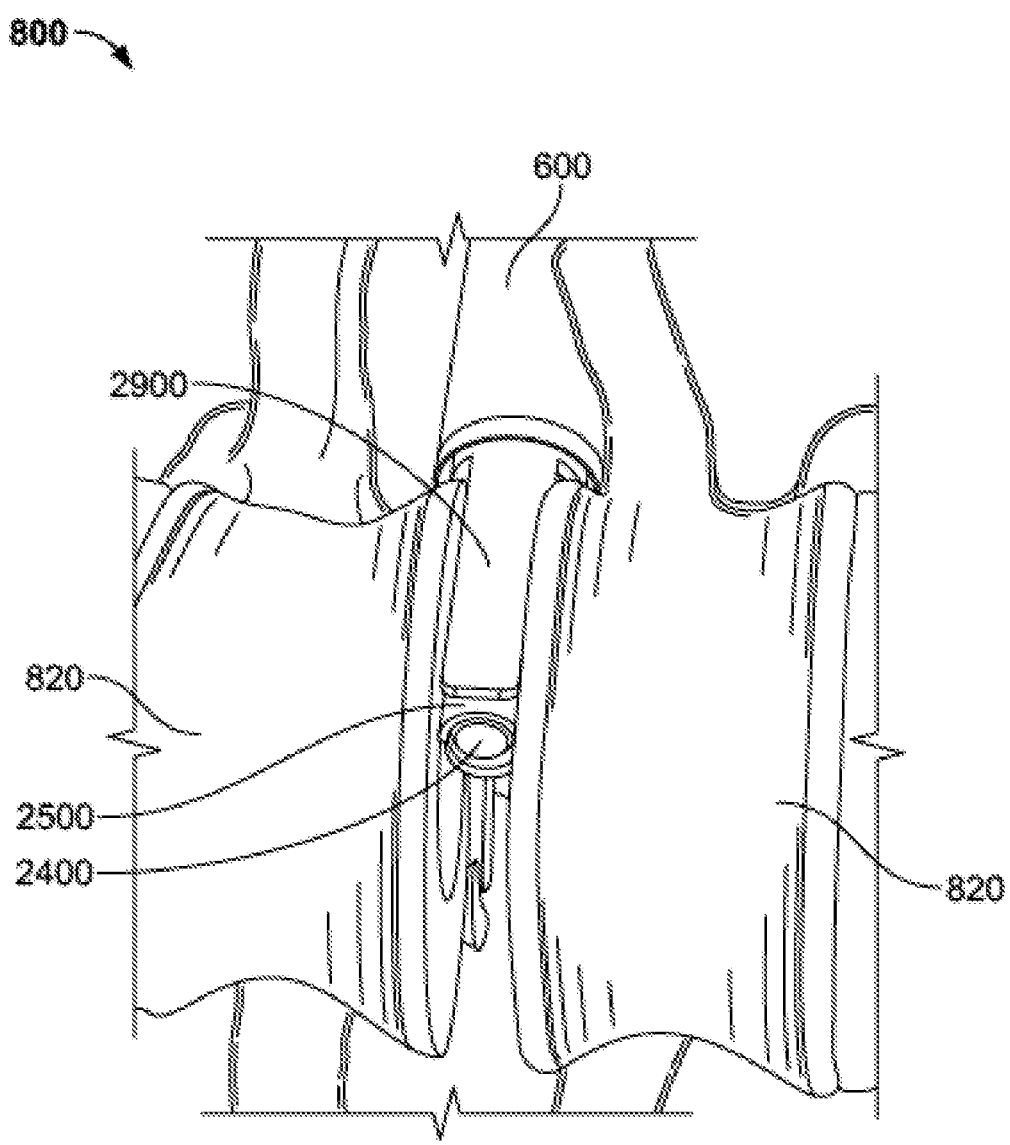
FIG. 18I is an enlarged schematic view of the delivery tube subassembly and the plunger subassembly positioned within the intervertebral space.

With the space holder 2900 in position in the intervertebral space and holding the adjacent vertebrae 820 in the distracted position, distractor 2800 may be removed from injector assembly 2100, as shown in FIG. 18G. At this point, the delivery tube subassembly 2500, already loaded with bone graft, and the plunger subassembly 2400, may be inserted into injection assembly 2100. The distal end of delivery tube subassembly 2500 may be advanced to the intervertebral space being held open by the space holder 2900, as shown in FIG. 18H. The user may then iteratively actuate handle subassembly 2100 until the desired amount of bone graft is expelled into the intervertebral space, or the plunger subassembly 2400 advances its maximum distance, as shown in FIG. 18I. Once the desired amount of bone graft has been delivered, the plunger subassembly 2400 and delivery tube subassembly 2500 may be removed from the injector assembly 2100. An implant, such as an intervertebral spacer or cage, may then be inserted into the intervertebral space through the cannula 2110 of the injector assembly 2100, or the injector assembly 2100 may be removed and the implant may then be inserted.

It should also be understood that, in some cases, cannula 2110 may be forced into the intervertebral space without a mechanism for initial distraction. Because the cannula 2110 may be rigid, the cannula 2110 may keep the adjacent vertebrae 820 distracted while bone graft is delivered, and while any other structures are inserted through cannula 2110.

In one embodiment of the invention, a bone graft delivery system, comprises:
 a bone graft injector assembly, including:
 a handle having a first arm pivotably connected to a second arm, the first arm being biased away from the second arm;
 a ratchet assembly extending from the second arm, the ratchet assembly including a pawl extending therefrom;
 a delivery tube assembly configured to mate with the first arm and configured to store a bone graft material therein;
 a plunger assembly configured to move through the delivery tube assembly, the plunger assembly including a shaft and a plunger tip at the distal end of the shaft;
 wherein at least a portion of the shaft includes a plurality of teeth, the pawl of the ratchet assembly being configured to contact one of the plurality of teeth and to drive the plunger assembly in a first direction when the ratchet assembly moves in the first direction, the pawl remaining in contact with the one tooth, the pawl further being configured to contact another one of the plurality of teeth after the ratchet assembly is moved in a second direction opposite the first direction; and
 an access portal assembly; and/or
 the delivery tube assembly comprises an outer cannula and an inner cannula; and/or
 the outer cannula has the general shape of a hollow cylinder and a distal end through which the bone graft material is configured to exit; and/or
 the distal end of the outer cannula includes an off-axis cutout formed in a portion of a circumference of the outer cannula; and/or
 the off-axis cutout is generally "U"-shaped; and/or
 at least a portion of the inner cannula is elongated and hollow and has a generally partially cylindrical shape; and/or
 at least a portion of the inner cannula is generally trough shaped;
 the access portal assembly comprises:
 a handle;
 a first arm connected to the handle;
 a second arm connected to the first arm; and
 a tube connected to and extending generally perpendicular from the second arm, wherein a distal end of the tube is beveled; and/or
 the beveled distal end of the tube is angled with respect to a wall of the tube between approximately 20 degrees and approximately 40 degrees; and/or
 the beveled distal end of the tube is angled with respect to the wall of the tube at approximately 30 degrees; and/or
 the second arm is angled with respect to the handle between approximately 10 degrees and approximately 30 degrees; and/or
 the second arm is angled with respect to the handle at approximately 20 degrees.

In another embodiment of the invention, a method of delivering a bone graft material to a patient comprises:
 providing an access tube assembly and a bone graft injector assembly comprising:
 a handle with a first arm pivotably connected to a second arm;
 a ratchet assembly extending from the second arm;
 a delivery tube assembly configured to mate with the first arm and configured to store a bone graft material therein; and
 a plunger assembly configured to move through the delivery tube assembly, the plunger assembly including a shaft configured to couple to a portion of the ratchet assembly and a plunger tip at the distal end of the shaft;
 creating an incision in the patient to access the bone;
 inserting the access tube assembly into the patient through the incision;
 loading the delivery tube assembly with the bone graft material; and
 expelling a first amount of bone graft material from the delivery tube assembly by moving the first arm toward the second arm to drive the ratchet assembly and the plunger assembly distally, the plunger tip forcing the first amount of bone graft material through the delivery tube assembly as the plunger tip moves through the delivery tube assembly; and/or
 simultaneously manipulating that access tube assembly with a first hand and the bone graft injector assembly with a second hand; and/or
 moving the first arm away from the second arm to move the ratchet assembly proximally with respect to the plunger assembly; and/or
 a biasing member biases the first arm away from the second arm and the step of moving the first arm away from the second arm is accomplished, at least in part, by the biasing member; and/or
 the biasing member is a spring; and/or
 expelling a second amount of bone graft material from the delivery tube assembly by moving the first arm toward the second arm to drive the ratchet assembly and the plunger assembly distally, the plunger tip forcing the second amount of bone graft material through the delivery tube assembly as the plunger tip moves through the delivery tube assembly; and/or
 simultaneously manipulating the access tube assembly with a first hand and the bone graft injector assembly with a second hand; and/or
 removing the bone graft injector assembly from the access tube assembly and inserting a tamping device into the access tube assembly.

According to a further embodiment of the invention, a bone graft injection system comprises:
 a body;
 a handle assembly operatively coupled to the body;
 a cannula coupled to and extending from the body;
 a tube configured to be positioned at least partially within the body and at least partially within the cannula; and
 a plunger configured to be positioned at least partially within the tube and operably coupled to the handle assembly so that actuation of the handle assembly advances the plunger within the tube; and/or
 a trocar configured to fit at least partially within the cannula; and/or
 the trocar has a handle, a shaft extending from the handle, and tip at one end of the shaft; and/or
 the tip has at least one cutting surface; and/or
 the tip has at least one non-cutting surface; and/or
 the tip is ramped such that a distalmost end of the tip has a height that is smaller than a proximalmost end of the tip; and/or a distractor configured to be positioned at least partially within the cannula; and a space holder configured to be positioned over at least a portion of the cannula; and/or the distractor has a distal tip having two opposing substantially planar surfaces; and/or the distractor has a distal tip with a height and a width, the height being smaller than the width; and/or the width of the distal tip is about 8 mm; and/or the space holder is configured to be translated along a longitudinal axis of the cannula and rotated about the longitudinal axis of the cannula; and/or the space holder has a distal tip having two prongs extending from diametrically opposed portions of the space holder.

According to yet another embodiment of the invention, a method for delivering a bone graft material to a surgical site in a patient comprises:

providing access through skin of a patient with an access portal;

inserting a trocar into a cannula extending from a bone graft injection device so that a distal tip of the trocar extends beyond a distal end of the cannula, the distal tip of the trocar having at least one cutting surface;

advancing the bone graft injection device through the access portal to the surgical site;

removing the trocar from the bone graft injection device;

inserting a delivery tube assembly loaded with the bone graft material into the cannula of the bone graft injection device; and expelling the bone graft material from the delivery tube assembly to the surgical site; and/or the step of advancing the bone graft injection device to the surgical site includes cutting tissue of the patient with the at least one cutting surface of the trocar; and/or the step of expelling the bone graft material includes iteratively actuating the bone graft injection device, such that each actuation advances at least some of the bone graft material through the delivery tube subassembly.

According to yet a further embodiment of the invention, a method for delivering a bone graft material to a space between adjacent vertebrae in a patient comprises:

providing access through skin of a patient with an access portal;

inserting a distractor into a cannula extending from a bone graft injection device so that a distal tip of the distractor extends beyond a distal end of the cannula;

positioning a space holder over the cannula so that a distal end of the space holder is positioned proximally of the distal tip of the distractor;

advancing the bone graft injection device through the access portal until the distal tip of the distractor is positioned within the intervertebral space;

rotating the distractor to distract the adjacent vertebrae;

advancing the space holder so that the distal end of the space holder is positioned within the intervertebral space;

removing the distractor from the bone graft injection device;

inserting a delivery tube assembly loaded with the bone graft material into the cannula of the bone graft injection device; and expelling the bone graft material from the delivery tube assembly to the surgical site.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. For example, one embodiment of an assembly or subassembly described above may be combined with other embodiments of assemblies or subassemblies described above.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A method for delivering a bone graft material to a surgical site in a patient comprising:

creating an incision in a skin of the patient;

inserting an access portal through the incision in the skin of the patient;

gripping a bone graft injector assembly with a first hand of a user, the bone graft injector assembly including a handle, a ratchet assembly, a delivery tube assembly configured to store the bone graft material therein, and a plunger assembly operably coupled to the handle and the ratchet assembly and configured to move through the delivery tube assembly;

after inserting the access portal, advancing the bone graft injector assembly through the access portal toward the surgical site;

after advancing the bone graft injector assembly through the access portal, positioning a distal tip of a distractor between adjacent vertebrae;

rotating the distal tip of the distractor while the distal tip is between adjacent vertebrae to increase an amount of space between the adjacent vertebrae;

after rotating the distal tip of the distractor, advancing a space holder distally over the distal tip;

after advancing the space holder distally over the distal tip, removing the distractor from the bone graft injector assembly, such that the space holder maintains the increased spacing between the adjacent vertebrae;

expelling a first amount of the bone graft material from the delivery tube assembly using the first hand gripping the bone graft injector assembly; and manipulating the access portal with a second hand of the user to change a position of the access portal while the first hand of the user is gripping the bone graft injector assembly, while the access portal is in the patient, and while the bone graft injector assembly is positioned within the access portal.

2. The method of claim 1, further comprising dilating the incision after creating the incision and before inserting the access portal through the incision.

3. The method of claim 2, wherein dilating the incision includes use of sequential dilators.

4. The method of claim 1, further comprising loading the delivery tube assembly with the bone graft material prior to creating the incision in the skin of the patient.

5. The method of claim 1, further comprising loading the delivery tube assembly with the bone graft material after creating the incision in the skin of the patient.

6. The method of claim 1, wherein expelling the first amount of the bone graft material from the delivery tube assembly using the first hand gripping the bone graft injector assembly includes moving a first arm of the handle toward a second arm of the handle while the first hand of the user grips the handle.

7. The method of claim 6, wherein moving the first arm of the handle toward the second arm of the handle drives plunger assembly distally through the delivery tube assembly.

8. The method of claim 7, wherein moving the first arm of the handle toward the second arm of the handle drives the ratchet assembly, and the driving of the ratchet assembly causes the driving of the plunger assembly distally.

9. The method of claim 7, wherein the plunger assembly includes a distal plunger tip that contacts the bone graft material as the plunger assembly is driven distally through the delivery tube assembly.

10. The method of claim 9, wherein the distal plunger tip is formed of a first material, and a shaft of the plunger assembly is formed of a second material different than the first material.

11. The method of claim 1, further comprising expelling a second amount of the bone graft material from the delivery tube assembly using the first hand gripping the bone graft injector assembly.

12. The method of claim 1, further comprising removing the bone graft injector assembly from the access portal, inserting a tamping device into the access portal, and tamping the first amount of bone graft material.

* * * * *